(12) United States Patent
Sass-Ørum et al.

(10) Patent No.: US 11,806,403 B2
(45) Date of Patent: Nov. 7, 2023

(54) THERAPEUTIC DERIVATIVES OF INTERLEUKIN-22

(71) Applicant: CytoKi Pharma ApS, Hellerup (DK)

(72) Inventors: Kristian Sass-Ørum, Bagsværd (DK); Rasmus Jørgensen, Hellerup (DK); Sebastian Beck Jørgensen, Bagsværd (DK); Henning Thøgersen, Bagsværd (DK); Thomas Hoeg-Jensen, Bagsværd (DK); Michael Paolo Bastner Sandrini, Bagsværd (DK)

(73) Assignee: CytoKi Pharma ApS, Hellerup (DK)

( * ) Notice: Subject to any disclaimer, the term of this patent is extended or adjusted under 35 U.S.C. 154(b) by 0 days.

(21) Appl. No.: 17/737,849

(22) Filed: May 5, 2022

(65) Prior Publication Data

US 2022/0347304 A1 Nov. 3, 2022

Related U.S. Application Data

(63) Continuation of application No. PCT/EP2020/081523, filed on Nov. 9, 2020.

(30) Foreign Application Priority Data

Nov. 7, 2019 (EP) .................................. 19207766

(51) Int. Cl.
| | | |
|---|---|---|
| C07K 14/54 | (2006.01) | |
| A61K 47/54 | (2017.01) | |
| A61P 1/16 | (2006.01) | |
| A61P 3/04 | (2006.01) | |
| A61P 3/10 | (2006.01) | |
| A61P 11/00 | (2006.01) | |

(52) U.S. Cl.
CPC .............. *A61K 47/542* (2017.08); *A61P 1/16* (2018.01); *A61P 3/04* (2018.01); *A61P 3/10* (2018.01); *A61P 11/00* (2018.01)

(58) Field of Classification Search
CPC .......... A61K 47/542; C07K 14/54; A61P 1/16
See application file for complete search history.

(56) References Cited

U.S. PATENT DOCUMENTS 10,160,793 B2 12/2018 Scheer et al.

FOREIGN PATENT DOCUMENTS

| | | | |
|---|---|---|---|
| JP | 2013533227 | A | 8/2013 |
| JP | 2014501262 | A | 1/2014 |
| JP | 2016522795 | A | 8/2016 |
| JP | 2016531156 | A | 10/2016 |
| JP | 2018511574 | A | 4/2018 |
| WO | WO-2011154349 | A2 | 12/2011 |
| WO | WO-2012087838 | A1 | 6/2012 |
| WO | WO-2014145016 | A2 | 9/2014 |
| WO | WO-2015038938 | A1 | 3/2015 |
| WO | WO-2016149501 | A2 | 9/2016 |
| WO | WO-2017011820 | A2 | 1/2017 |
| WO | WO-2019028419 | A1 | 2/2019 |
| WO | WO-2021089875 | A1 | 5/2021 |

OTHER PUBLICATIONS

International Search Report and Written Opinion for Application No. PCT/EP2022/062828, dated Oct. 6, 2022, 10 pages.
International Search Report and Written Opinion for Application No. PCT/EP2022/062846, dated Oct. 25, 2022, 11 pages.
Nagem et al., "Crystal structure of recombinant human interleukin-22," Structure, vol. 10, No. 8, Aug. 1, 2002, pp. 1051-1062.
Qian et al., "Long-Acting human Interleukin 2 Bioconjugate Modified with Fatty Acids by Sortase A," Bioconjugate Chemistry, vol. 32, No. 3, Mar. 2021, pp. 615-625.
Van Witteloostuijn et al., "Half-Life Extension of Biopharmaceuticals using Chemical Methods: Alternatives to PEGylation," ChemMedchem Communications, vol. 11, No. 22, Oct. 24, 2016, pp. 2474-2495.
Bech et al., "Chemical strategies for half-life extension of biopharmaceuticals: Lipidation and Its Alternatives," ACS Medicinal Chemistry Letters, vol. 9, No. 7, Jul. 12, 2018, pp. 577-580.
Extended European Search Report for Application No. EP19207766.7, dated Mar. 31, 2020, 9 pages.
International Search Report and Written Opinion for Application No. PCT/EP2020/081523, dated Nov. 30, 2020, 12 pages.
Lau et al., "Discovery of the Once-Weekly Glucagon-Like Peptide-1 (GLP-1) Analogue Semaglutide," Journal of Medicinal Chemistry, Sep. 2015, 58(18), pp. 7370-7380.
Ouyang et al., "IL-10 Family Cytokines IL-10 and IL-22: from Basic Science to Clinical Translation," Immunity., vol. 50, No. 4, Apr. 1, 2019, pp. 871-891.
Petersen et al., "Comparison of a Luminescent Oxygen Channeling Immunoassay and an ELISA for detecting Insulin Aspart in human serum," Journal of Pharmaceutical and Biomedical Analysis, Jan. 2010, vol. 51, Issue 1, pp. 217-224.
Poulsen et al., "A Luminescent Oxygen Channeling Immunoassay for the Determination of Insulin in Human Plasma," Journal of Biomolecular Screening, Mar. 2007, 12(2), pp. 240-247.
Stefanich et al., "Pre-clinical and translational pharmacology of a human interleukin-22 IgG fusion protein for potential treatment of infections or inflammatory diseases," Biochemical Pharmacology, Jun. 2018, vol. 152, pp. 224-235.

*Primary Examiner* — Gyan Chandra
(74) *Attorney, Agent, or Firm* — COOLEY LLP; Tanya Heare-Rowlands; Matthew Pavao

(57) ABSTRACT

The invention relates to novel derivatives of Interleukin-22 (IL-22), particularly those comprising a fatty acid covalently attached to an IL-22 protein, and their use in therapy.

96 Claims, 23 Drawing Sheets
Specification includes a Sequence Listing.

SEQUENCE LISTING

```
<160> NUMBER OF SEQ ID NOS: 26

<210> SEQ ID NO 1
<211> LENGTH: 146
<212> TYPE: PRT
<213> ORGANISM: Homo sapiens

<400> SEQUENCE: 1

Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
    130                 135                 140

Cys Ile
145

<210> SEQ ID NO 2
<211> LENGTH: 5
```

```
<212> TYPE: PRT
<213> ORGANISM: Artificial Sequence
<220> FEATURE:
<223> OTHER INFORMATION: n-mer that can be inserted in SEQ ID NO. 1 (to
      create an experimentally altered version of SEQ ID NO. 1)

<400> SEQUENCE: 2

Arg Val Gln Phe Gln
1               5

<210> SEQ ID NO 3
<211> LENGTH: 5
<212> TYPE: PRT
<213> ORGANISM: Artificial Sequence
<220> FEATURE:
<223> OTHER INFORMATION: n-mer that can be inserted in SEQ ID NO. 1 (to
      create an experimentally altered version of SEQ ID NO. 1

-continued

```
1               5

<210> SEQ ID NO 8
<211> LENGTH: 44
<212> TYPE: PRT
<213> ORGANISM: Artificial Sequence
<220> FEATURE:
<223> OTHER INFORMATION: n-mer that can be inserted in SEQ ID NO. 1 (to
      create an experimentally altered version of SEQ ID NO. 1)

<400> SEQUENCE: 8

Arg Ala Ala Ser Ala Gly Ser Tyr Ser Glu Trp Ser Met Thr Pro Arg
1               5                   10                  15

Phe Thr Pro Trp Trp Glu Thr Lys Ile Asp Pro Pro Val Met Asn Ile
            20                  25                  30

Thr Gln Val Asn Gly Ser Leu Leu Val Ile Leu His
        35                  40

<210> SEQ ID NO 9
<211> LENGTH: 8
<212> TYPE: PRT
<213> ORGANISM: Artificial Sequence
<220> FEATURE:
<223> OTHER INFORMATION: n-mer that can be added as an N-terminal
      peptide on SEQ ID NO. 1 (to create an experimentally altered
      version of SEQ ID NO. 1)

<400> SEQUENCE: 9

Gly Pro Ala Cys Glu Pro Glu Glu
1               5

<210> SEQ ID NO 10
<211> LENGTH: 13
<212> TYPE: PRT
<213> ORGANISM: Artificial Sequence
<220> FEATURE:
<223> OTHER INFORMATION: n-mer that can be added as an N-terminal
      peptide on SEQ ID NO. 1 (to create an experimentally altered
      version of SEQ ID NO. 1)

<400> SEQUENCE: 10

Gly Gly Ser Ser Gly Ser Gly Ser Glu Val Leu Phe Gln
1               5                   10

<210> SEQ ID NO 11
<211> LENGTH: 15
<212> TYPE: PRT
<213> ORGANISM: Artificial Sequence
<220> FEATURE:
<223> OTHER INFORMATION: n-mer that can be added as an N-terminal
      peptide on SEQ ID NO. 1 (to create an experimentally altered
      version of SEQ ID NO. 1)

<400> SEQUENCE: 11

Gly Pro Gly Ser Gly Ser Gly Ser Cys Gly Ser Gly Ser Gly Ser
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: n-mer that can be added as an N-terminal
      peptide on SEQ ID NO. 1 (to create an experimentally altered
      version of SEQ ID NO. 1)

<400> SEQUENCE: 12
```

```
Gly Gly Ser Ser Gly Ser Gly Ser Glu Val Leu Phe Gln Gly Pro Gly
1               5                   10                  15
```

<210> SEQ ID NO 13
<211> LENGTH: 21
<212> TYPE: PRT
<213> ORGANISM: Artificial Sequence
<220> FEATURE:
<223> OTHER INFORMATION: n-mer that can be added as an N-terminal
      peptide on SEQ ID NO. 1 (to create an experimentally altered
      version of SEQ ID NO. 1)

<400> SEQUENCE: 13

```
Gly Gly Ser Ser Gly Ser Gly Ser Glu Val Leu Phe Gln Gly Pro Ala
1               5                   10                  15

Cys Glu Pro Glu Glu
            20
```

<210> SEQ ID NO 14
<211> LENGTH: 28
<212> TYPE: PRT
<213> ORGANISM: Artificial Sequence
<220> FEATURE:
<223> OTHER INFORMATION: n-mer that can be added as an N-terminal
      peptide on SEQ ID NO. 1 (to create an experimentally altered
      version of SEQ ID NO. 1)

<400> SEQUENCE: 14

```
Gly Gly Ser Ser Gly Ser Gly Ser Glu Val Leu Phe Gln Gly Pro Gly
1               5                   10                  15

Ser Gly Ser Gly Ser Cys Gly Ser Gly Ser Gly Ser
            20                  25
```

<210> SEQ ID NO 15
<211> LENGTH: 7
<212> TYPE: PRT
<213> ORGANISM: Artificial Sequence
<220> FEATURE:
<223> OTHER INFORMATION: n-mer that can be added as a C-terminal peptide
      on SEQ ID NO. 1 (to create an experimentally altered version of
      SEQ ID NO. 1)

<400> SEQUENCE: 15

```
Gly Ser Gly Ser Gly Ser Cys
1               5
```

<210> SEQ ID NO 16
<211> LENGTH: 149
<212> TYPE: PRT
<213> ORGANISM: Artificial Sequence
<220> FEATURE:
<223> OTHER INFORMATION: Experimentally altered version of SEQ ID NO. 1

<400> SEQUENCE: 16

```
Gly Pro Gly Cys Pro Ile Ser Ser His Cys Arg Leu Asp Lys Ser Asn
1               5                   10                  15

Phe Gln Gln Pro Tyr Ile Thr Asn Arg Thr Phe Met Leu Ala Lys Glu
                20                  25                  30

Ala Ser Leu Ala Asp Asn Asn Thr Asp Val Arg Leu Ile Gly Glu Lys
            35                  40                  45

Leu Phe His Gly Val Ser Met Ser Glu Arg Cys Tyr Leu Met Lys Gln
        50                  55                  60

Val Leu Asn Phe Thr Leu Glu Glu Val Leu Phe Pro Gln Ser Asp Arg
65                  70                  75                  80
```

```
Phe Gln Pro Tyr Met Gln Glu Val Val Pro Phe Leu Ala Arg Leu Ser
                85                  90                  95

Asn Arg Leu Ser Thr Cys His Ile Glu Gly Asp Asp Leu His Ile Gln
            100                 105                 110

Arg Asn Val Gln Lys Leu Lys Asp Thr Val Lys Lys Leu Gly Glu Ser
        115                 120                 125

Gly Glu Ile Lys Ala Ile Gly Glu Leu Asp Leu Leu Phe Met Ser Leu
    130                 135                 140

Arg Asn Ala Cys Ile
145
```

<210> SEQ ID NO 17
<211> LENGTH: 161
<212> TYPE: PRT
<213> ORGANISM: Artificial Sequence
<220> FEATURE:
<223> OTHER INFORMATION: Experimentally altered version of SEQ ID NO. 1

<400> SEQUENCE: 17

```
Gly Pro Gly Ser Gly Ser Gly Ser Cys Gly Ser Gly Ser Gly Ser Ala
1               5                   10                  15

Pro Ile Ser Ser His Cys Arg Leu Asp Lys Ser Asn Phe Gln Gln Pro
            20                  25                  30

Tyr Ile Thr Asn Arg Thr Phe Met Leu Ala Lys Glu Ala Ser Leu Ala
        35                  40                  45

Asp Asn Asn Thr Asp Val Arg Leu Ile Gly Glu Lys Leu Phe His Gly
    50                  55                  60

Val Ser Met Ser Glu Arg Cys Tyr Leu Met Lys Gln Val Leu Asn Phe
65                  70                  75                  80

Thr Leu Glu Glu Val Leu Phe Pro Gln Ser Asp Arg Phe Gln Pro Tyr
                85                  90                  95

Met Gln Glu Val Val Pro Phe Leu Ala Arg Leu Ser Asn Arg Leu Ser
            100                 105                 110

Thr Cys His Ile Glu Gly Asp Asp Leu His Ile Gln Arg Asn Val Gln
        115                 120                 125

Lys Leu Lys Asp Thr Val Lys Lys Leu Gly Glu Ser Gly Glu Ile Lys
    130                 135                 140

Ala Ile Gly Glu Leu Asp Leu Leu Phe Met Ser Leu Arg Asn Ala Cys
145                 150                 155                 160

Ile
```

<210> SEQ ID NO 18
<211> LENGTH: 149
<212> TYPE: PRT
<213> ORGANISM: Artificial Sequence
<220> FEATURE:
<223> OTHER INFORMATION: Experimentally altered version of SEQ ID NO. 1

<400> SEQUENCE: 18

```
Gly Pro Gly Cys Pro Ile Ser Ser His Cys Arg Leu Asp Lys Ser Asn
1               5                   10                  15

Phe Gln Gln Pro Tyr Ile Thr Asn Arg Thr Phe Met Leu Ala Lys Glu
            20                  25                  30

Ala Ser Leu Ala Asp Gln Asn Thr Asp Val Arg Leu Ile Gly Glu Lys
        35                  40                  45

Leu Phe His Gly Val Ser Met Ser Glu Arg Cys Tyr Leu Met Lys Gln
    50                  55                  60
```

-continued

Val Leu Gln Phe Thr Leu Glu Glu Val Leu Phe Pro Gln Ser Asp Arg
65                  70                  75                  80

Phe Gln Pro Tyr Met Gln Glu Val Val Pro Phe Leu Ala Arg Leu Ser
                85                  90                  95

Asn Arg Leu Ser Thr Cys His Ile Glu Gly Asp Asp Leu His Ile Gln
            100                 105                 110

Arg Asn Val Gln Lys Leu Lys Asp Thr Val Lys Lys Leu Gly Glu Ser
        115                 120                 125

Gly Glu Ile Lys Ala Ile Gly Glu Leu Asp Leu Leu Phe Met Ser Leu
    130                 135                 140

Arg Asn Ala Cys Ile
145

<210> SEQ ID NO 19
<211> LENGTH: 146
<212> TYPE: PRT
<213> ORGANISM: Artificial Sequence
<220> FEATURE:
<223> OTHER INFORMATION: Experimentally altered version of SEQ ID NO. 1

<400> SEQUENCE: 19

Cys Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
                20                  25                  30

Ala Asp Gln Asn Thr Asp Val Arg Leu Ile Gly Glu Lys Leu Phe His
            35                  40                  45

Gly Val Ser Met Ser Glu Arg Cys Tyr Leu Met Lys Gln Val Leu Gln
    50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
    130                 135                 140

Cys Ile
145

<210> SEQ ID NO 20
<211> LENGTH: 147
<212> TYPE: PRT
<213> ORGANISM: Artificial Sequence
<220> FEATURE:
<223> OTHER INFORMATION: Experimentally altered version of SEQ ID NO. 1

<400> SEQUENCE: 20

Gly Ala Pro Ile Ser Ser Cys Cys Arg Leu Asp Lys Ser Asn Phe Gln
1               5                   10                  15

Gln Pro Tyr Ile Thr Asn Arg Thr Phe Met Leu Ala Lys Glu Ala Ser
                20                  25                  30

Leu Ala Asp Gln Asn Thr Asp Val Arg Leu Ile Gly Glu Lys Leu Phe
            35                  40                  45

His Gly Val Ser Met Ser Glu Arg Cys Tyr Leu Met Lys Gln Val Leu
    50                  55                  60

```
Gln Phe Thr Leu Glu Glu Val Leu Phe Pro Gln Ser Asp Arg Phe Gln
 65                  70                  75                  80

Pro Tyr Met Gln Glu Val Val Pro Phe Leu Ala Arg Leu Ser Asn Arg
                 85                  90                  95

Leu Ser Thr Cys His Ile Glu Gly Asp Asp Leu His Ile Gln Arg Asn
            100                 105                 110

Val Gln Lys Leu Lys Asp Thr Val Lys Lys Leu Gly Glu Ser Gly Glu
        115                 120                 125

Ile Lys Ala Ile Gly Glu Leu Asp Leu Leu Phe Met Ser Leu Arg Asn
    130                 135                 140

Ala Cys Ile
145

<210> SEQ ID NO 21
<211> LENGTH: 146
<212> TYPE: PRT
<213> ORGANISM: Artificial Sequence
<220> FEATURE:
<223> OTHER INFORMATION: Experimentally altered version of SEQ ID NO. 1

<400> SEQUENCE: 21

Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Cys Asp Gln Asn Thr Asp Val Arg Leu Ile Gly Glu Lys Leu Phe His
        35                  40                  45

Gly Val Ser Met Ser Glu Arg Cys Tyr Leu Met Lys Gln Val Leu Gln
    50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
    130                 135                 140

Cys Ile
145

<210> SEQ ID NO 22
<211> LENGTH: 146
<212> TYPE: PRT
<213> ORGANISM: Artificial Sequence
<220> FEATURE:
<223> OTHER INFORMATION: Experimentally altered version of SEQ ID NO. 1

<400> SEQUENCE: 22

Gly Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
```

```
                50                  55                  60

Phe Thr Leu Glu Glu Val Leu Phe Pro Gln Ser Asp Arg Phe Gln Pro
 65                  70                  75                  80

Tyr Met Gln Glu Val Val Pro Phe Leu Ala Arg Leu Ser Asn Arg Leu
                 85                  90                  95

Ser Thr Cys His Ile Glu Gly Asp Asp Leu His Ile Gln Arg Asn Val
                100                 105                 110

Gln Lys Leu Lys Asp Thr Val Lys Lys Leu Gly Glu Ser Gly Glu Ile
            115                 120                 125

Lys Ala Ile Gly Glu Leu Asp Leu Leu Phe Met Ser Leu Arg Asn Ala
        130                 135                 140

Cys Ile
145

<210> SEQ ID NO 23
<211> LENGTH: 146
<212> TYPE: PRT
<213> ORGANISM: Artificial Sequence
<220> FEATURE:
<223> OTHER INFORMATION: Experimentally altered version of SEQ ID NO. 1

<400> SEQUENCE: 23

Gly Pro Ile Ser Ser His Cys Arg Leu Asp Lys Ser Asn Phe Gln Gln
  1               5                  10                  15

Pro Tyr Ile Thr Asp Arg Thr Phe Met Leu Ala Lys Glu Ala Ser Leu
                 20                  25                  30

Ala Asp Asp Asn Thr Asp Val Arg Leu Ile Gly Glu Lys Leu Phe His
             35                  40                  45

Gly Val Ser Met Ser Glu Arg Cys Tyr Leu Met Lys Gln Val Leu Asp
         50                  55                  60

Phe Thr Leu Glu Glu Val Leu Phe Pro Gln Ser Asp Arg Phe Gln Pro
 65                  70                  75                  80

Tyr Met Gln Glu Val Val Pro Phe Leu Ala Arg Leu Ser Asn Arg Leu
                 85                  90                  95

Ser Thr Cys His Ile Glu Gly Asp Asp Leu His Ile Gln Arg Asn Val
                100                 105                 110

Gln Lys Leu Lys Asp Thr Val Lys Lys Leu Gly Glu Ser Gly Glu Ile
            115                 120                 125

Lys Ala Ile Gly Glu Leu Asp Leu Leu Phe Met Ser Leu Arg Asn Ala
        130                 135                 140

Cys Ile
145

<210> SEQ ID NO 24
<211> LENGTH: 146
<212> TYPE: PRT
<213> ORGANISM: Artificial Sequence
<220> FEATURE:
<223> OTHER INFORMATION: Experimentally altered version of SEQ ID NO. 1

<400> SEQUENCE: 24

Gly Pro Ile Ser Ser His Cys Arg Leu Asp Lys Ser Asn Phe Gln Gln
  1               5                  10                  15

Pro Tyr Ile Thr Asn Arg Thr Phe Met Leu Ala Lys Glu Ala Ser Leu
                 20                  25                  30

Ala Asp Gln Asn Thr Asp Val Arg Leu Ile Gly Glu Lys Leu Phe His
             35                  40                  45
```

```
Gly Val Ser Met Ser Glu Arg Cys Tyr Leu Met Lys Gln Val Leu Gln
    50                  55                  60

Phe Thr Leu Glu Glu Val Leu Phe Pro Gln Ser Asp Arg Phe Gln Pro
65              70                  75                  80

Tyr Met Gln Glu Val Val Pro Phe Leu Ala Arg Leu Ser Asn Arg Leu
                85              90                  95

Ser Thr Cys His Ile Glu Gly Asp Asp Leu His Ile Gln Arg Asn Val
                100             105                 110

Gln Lys Leu Lys Asp Thr Val Lys Lys Leu Gly Glu Ser Gly Glu Ile
            115             120                 125

Lys Ala Ile Gly Glu Leu Asp Leu Leu Phe Met Ser Leu Arg Asn Ala
        130             135             140

Cys Ile
145

<210> SEQ ID NO 25
<211> LENGTH: 19
<212> TYPE: PRT
<213> ORGANISM: Artificial Sequence
<220> FEATURE:
<223> OTHER INFORMATION: His-tag

<400> SEQUENCE: 25

His His His His His His Gly Gly Ser Ser Gly Ser Gly Ser Glu Val
1               5                   10                  15

Leu Phe Gln

<210> SEQ ID NO 26
<211> LENGTH: 7
<212> TYPE: PRT
<213> ORGANISM: Artificial Sequence
<220> FEATURE:
<223> OTHER INFORMATION: Consensus sequence for native cut site in
      protease-cleavable TEV linker

<400> SEQUENCE: 26

Glu Asn Leu Tyr Phe Gln Ser
1               5
```

THERAPEUTIC DERIVATIVES OF INTERLEUKIN-22

CROSS-REFERENCE TO RELATED PATENT APPLICATIONS

This application is a bypass continuation of International Application No. PCT/EP2020/081523, filed on Nov. 9, 2020, which claims priority to European Application No. 19207766.7 filed on Nov. 7, 2019. Each of these applications is incorporated herein by reference in its entirety.

REFERENCE TO THE SEQUENCE LISTING

The instant application contains a Sequence Listing, which has been submitted electronically in ASCII format via EFS-Web and is hereby incorporated by reference in its entirety. Said ASCII copy, created May 5, 2022, is named CTKI_001_C01US_Sequence_Listing.txt and is 19,607 bytes in size.

FIELD OF THE INVENTION

The present invention relates to novel derivatives of Interleukin-22 (IL-22), and in particular to derivatives comprising a fatty acid covalently attached to an IL-22 protein. The invention also encompasses methods for their production and their use in therapy, including the treatment, prevention and amelioration of metabolic, liver, pulmonary, gut, kidney and skin diseases, disorders and conditions.

BACKGROUND OF THE INVENTION

IL-22 is a 146 amino acid protein with a molecular weight of 17 KDa. It belongs to the IL-10 family of cytokines and selectively activates a heterodimeric receptor consisting of an IL-10 receptor B subunit (IL-10RA2), which is ubiquitously expressed, and an IL-22 receptor A subunit (IL-22RA1), which has an epithelial restricted expression. It is a unique cytokine in that it is released from immune cells, but selectively targets epithelial cells. Hence, the signaling pathways induced by IL-22 may have relevance in different tissues (targets include skin, intestine, lung, liver, kidney, pancreas and thymus), but IL-22 activates them in an epithelial-specific manner. A soluble binding protein, IL-22BP, neutralises IL-22 and thus regulates its effect.

IL-22 is released as a response to signals reflecting chemical or mechanical injury, e.g. aryl hydrocarbon receptor activation in response to environmental toxins or tryptophan intermediates, and the activation of pattern recognition receptors, such as toll-like receptor 4, in response to proteins, fragments and debris from dying cells or invading pathogens. IL-22 release is further stimulated by certain cytokines, in particular IL-23 and to a lesser extent IL1β. IL-22 is thus secreted as a response to cues reflecting pathogen infection and immune activation too.

The effect of IL-22 is the result of an orchestrated engagement of several activities/pathways. IL-22 acts on epithelial barrier tissues and organs upon injury to protect the cells and maintain barrier function (e.g. through activation of anti-apoptotic gene programs). It also accelerates repair (e.g. by inducing the proliferation of mature cells and activation of stem cells), prevents fibrosis (e.g. through reducing epithelial-mesenchymal transition, antagonising the NLRP3 inflammasome and inducing hepatic stellate cell senescence) and controls inflammation (e.g. by inducing anti-microbial peptides and chemotaxis signals). IL-22 has been reported as able to treat a range of medical conditions, including those often observed in diabetic or overweight mammals, such as hyperglycemia, hyperlipidemia and hyperinsulinemia.

However, IL-22 is generally cleared quickly from the body by the kidneys, which limits its use in clinical practice. Known methods for extending the half-life of circulating IL-22 therefore seek to artificially increase the size of IL-22 beyond 70 kDa, so as to avoid renal clearance. Ligating IL-22 to an Fc antibody fragment is currently the best solution to this effect; Genentech and Generon Shanghai both have long-acting IL-22-Fc fusions in clinical development. Modifying IL-22 with polyethylene glycol (PEGylation) is another known means for avoiding renal clearance.

However, these existing solutions are not without their disadvantages. The available data suggest that PEG itself is immunogenic and PEG-containing vacuoles are observed in cells with PEGylated biologicals. Decreased activity and heterogeneity are also disadvantageous aspects of PEGylation. Although Fc fusion technology is very well known, adding an Fc antibody fragment represents a major change in the structure of IL-22, which affects its properties beyond half-life extension. As Fc fusion increases the size of the protein from approximately 17 kDa to approximately 85 kDa, properties such as diffusion rate, distribution and receptor engagement kinetics may be affected. For example, some Fc fusions are slowly absorbed and/or are too large for administration via certain routes. Both Genentech and Generon also report moderate and reversible skin reactions as dose-limiting adverse effects of IL-22-Fc fusions. Furthermore, the potency may be affected through steric hindrance caused by the large fusion partner.

A need therefore remains in the art for new biocompatible modifiers of IL-22 that enhance circulating half-lives and demonstrate optimised pharmacokinetic and pharmacodynamic properties compared to the native molecule. Ideally they should maintain potency and other properties of the native molecule and also avoid toxicity, immunogenicity and any other adverse reactions demonstrated by known derivatives.

SUMMARY OF THE INVENTION

In a first aspect, there is provided a derivative of IL-22 comprising a fatty acid covalently attached to an IL-22 protein.

In embodiments of the invention, the fatty acid is covalently attached to the IL-22 protein by a linker.

The fatty acid may be of Formula I:

HOOC—(CH$_2$)$_x$—CO—*, wherein x is an integer in the range of 10-18, optionally 12-18, 14-16 or 16-18, and * designates a point of attachment to the IL-22 protein or linker. It may be a fatty diacid, such as a C12, C14, C16, C18 or C20 diacid. Advantageously, the fatty acid is a C16 or C18 diacid, and most advantageously it is a C18 diacid.

The IL-22 protein may be native mature human IL-22 (hereinafter "hIL-22") or a variant thereof. The variant may be a substituted form of hIL-22, optionally substituted at position 1, 21, 35, 64, 113 and/or 114. It may comprise a substitution of hIL-22 selected from the group consisting of A1C, A1G, A1H, N21C, N21D, N21Q, N35C, N35D, N35H, N35Q, N64C, N64D, N64Q, N64W, Q113C, Q113R, K114C and K114R. Advantageously, the variant comprises a Cys residue at position 1 of hIL-22.

The variant may be an extended form of hIL-22. It may comprise an N-terminal peptide, such as an N-terminal trimer. Advantageously, the variant comprises an N-terminal G-P-G.

The linker may comprise one or more amino acids, optionally including glutamic acid (Glu) and/or lysine (Lys). The linker may include an oxyethylene glycine unit or multiple linked oxyethylene glycine units, optionally 2-5 such units, advantageously 2 units. The linker may comprise one or more oligo(ethylene glycol) (OEG) residues. It may comprise an ethylenediamine (C2DA) group and/or an acetamide (Ac) group. Advantageously, the linker comprises all of the aforementioned elements in combination. In particular, the linker may be γGlu-OEG-OEG-C2DA-Ac, γGlu-γGlu-γGlu-γGlu-OEG-OEG-εLys-αAc or γGlu-OEG-OEG-εLys-αAc.

The linker may be a Cys-reactive linker attached to a Cys residue in the hIL-22 or variant thereof. It may be attached at position −7, −5, 1, 6, 33, 113, 114 or 153 of the hIL-22 or variant thereof (where positions −7, −5 etc. are as defined herein). As an example, the linker may be attached to a Cys residue substituted at position 1, 6, 33, 113 or 114 of hIL-22. It may be attached to a Cys residue at position −5, −7 or 153 relative to hIL-22. Advantageously, the linker is attached to a Cys residue substituted at position 1 of hIL-22.

In an embodiment, the derivative comprises a C14, C16, C18 or C20 diacid covalently attached by a linker to a variant of hIL-22, wherein the variant comprises an N-terminal G-P-G and a Cys residue at position 1 of hIL-22 and the linker is optionally attached to said Cys residue. Exemplary derivatives of the invention are those identified herein as Derivatives 1-10.

In a second aspect, there is provided a process for preparing a derivative of the first aspect comprising covalently attaching a fatty acid to an IL-22 protein.

In a third aspect, there is provided a pharmaceutical composition comprising a derivative of the first aspect, and a pharmaceutically acceptable vehicle.

In a fourth aspect, there is provided a derivative of the first aspect or a pharmaceutical composition of the third aspect, for use in therapy.

In a fifth aspect, there is provided a derivative of the first aspect or a pharmaceutical composition of the third aspect, for use in a method of treating a metabolic, liver, pulmonary, gut, kidney or skin disease, disorder or condition.

The metabolic disease, disorder or condition may be obesity, diabetes type 1, diabetes type 2, hyperlipidemia, hyperglycemia or hyperinsulinemia.

The liver disease, disorder or condition may be non-alcoholic fatty liver disease (NAFLD), non-alcoholic steatohepatitis (NASH), cirrhosis, alcoholic hepatitis, acute liver failure, chronic liver failure, acute-on-chronic liver failure (ACLF), acute liver injury, acetaminophen induced liver toxicity, sclerosing cholangitis, biliary cirrhosis or a pathological condition caused by surgery or transplantation.

The pulmonary disease, disorder or condition may be chronic obstructive pulmonary disease (COPD), cystic fibrosis, bronchiectasis, idiopathic pulmonary fibrosis, acute respiratory distress syndrome, a chemical injury, a viral infection, a bacterial infection or a fungal infection.

The gut disease, disorder or condition may be inflammatory bowel disease (IBD), ulcerative colitis, Crohn's disease, graft-versus-host-disease (GvHD), a chemical injury, a viral infection or a bacterial infection.

The kidney disease, disorder or condition may be acute kidney disease or chronic kidney disease.

The skin disease, disorder or condition may be a wound, inflammatory disease or GvHD.

DETAILED DESCRIPTION

Figure 1A:
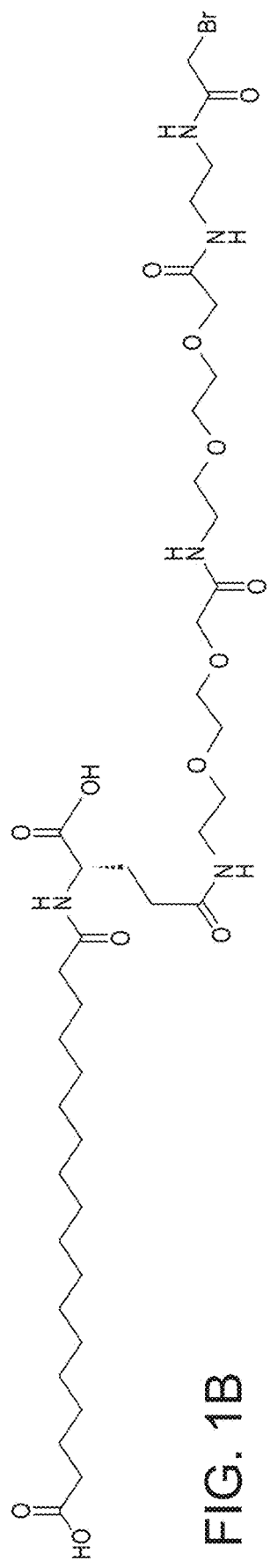
FIGS. 1A-1C illustrate a (FIG. 1A) C18 diacid, (FIG. 1B) C16 diacid, and (FIG. 1C) C14 diacid, each connected to a linker comprising a Cys-reactive unit. These combinations of fatty acids and linkers are employed in the derivatives of the invention identified herein as Derivatives 1-10.

In what follows, Greek letters are represented by their symbol rather than their written name. For example, α=alpha, ε=epsilon, γ=gamma and μ=mu. Amino acid residues may be identified by their full name, three-letter code or one-letter code, all of which are fully equivalent.

The term "derivative of IL-22", as used herein, refers to an IL-22 protein having a covalently attached fatty acid. The term encompasses both derivatives in which the fatty acid is covalently attached to the IL-22 protein directly and those in which the covalent attachment is by a linker.

The covalent attachment of fatty acids is a proven technology for half-life extension of peptides and proteins and is a way of subtending a fatty acid from the peptide or protein. It is known from marketed products for types 1 and 2 diabetes, such as insulins Levemir® (detemir) and Tresiba® (degludec), and glucagon-like peptide-1 (GLP-1) derivatives Victoza® (liraglutide) and Ozempic® (semaglutide).

Fatty acid attachment enables binding to albumin, thereby preventing renal excretion and providing some steric protection against proteolysis. Advantageously, it offers a minimal modification to IL-22 compared to Fc fusion or PEGylation. In this regard, whilst Fc fusion and PEGylation aim to increase the size of IL-22 beyond the threshold for renal clearance, derivatives comprising a fatty acid covalently attached to an IL-22 protein retain a small size similar to that of the IL-22 protein. Thus, as the fatty acid attachment is a minimal modification, the resultant derivative is believed to maintain native-like properties including distribution, diffusion rate and receptor engagement (binding, activation and trafficking) and minimise immunogenicity risk.

As above, fatty acid attachment has proven therapeutic efficacy in insulin and GLP-1 derivatives for diabetes. However, IL-22 is a very different protein in terms of its size, sequence and biological properties. It was therefore counterintuitive to the inventors that fatty acids could be covalently attached to IL-22 whilst maintaining therapeutic effect. It was particularly surprising that such a minimal modification to IL-22 could result in high potency (close to hIL-22) combined with a very long circulatory half-life.

In a first aspect, therefore, the invention relates to a derivative of IL-22 comprising a fatty acid covalently attached to an IL-22 protein. The fatty acid may be covalently attached to the IL-22 protein directly or via a linker, which itself can be devised of various subunits. The term, "IL-22 protein", as used herein, can mean a native IL-22 protein, such as hIL-22, or a variant thereof. A "variant" can be a protein having a similar amino acid sequence to that of the native protein, as further defined herein.

In nature, human IL-22 protein is synthesised with a signal peptide of 33 amino acids for secretion. The mature human IL-22 protein (i.e. hIL-22) is 146 amino acids in length and has 80.8% sequence identity with murine IL-22 (the latter being 147 amino acids in length).

The amino acid sequence of hIL-22 is identified herein as SEQ ID NO. 1. Like other IL-10 family members, the IL-22 structure contains six a-helices (referred to as helices A to F).

The derivatives of the invention may thus have the native amino acid sequence of hIL-22. Alternatively, they may have one or more amino acid sequence variations within the native sequence. They may additionally or alternatively include one or more amino acid sequence variations relative to (i.e. outside) the native sequence. Thus, in an embodiment, the derivative comprises a fatty acid covalently attached to hIL-22 or a variant thereof.

Expressions such as "within", "relative to", "corresponding to" and "equivalent to" are used herein to characterise the site of change and/or covalent attachment of a fatty acid in an IL-22 protein by reference to the sequence of the native protein, e.g. hIL-22. In SEQ ID NO. 1, the first amino acid residue of hIL-22 (alanine (Ala)) is assigned position 1.

Thus, a variation within the sequence of hIL-22 is a variation to any of residue numbers 1-146 in SEQ ID NO. 1. For example, a Glu substitution for the native Asp at residue 10 in hIL-22 is represented herein as "D10E". If the derivative also has a fatty acid covalently attached at position 10, it is herein referred to as attachment at residue "10E".

A variation relative to the sequence of hIL-22, however, is a variation external to residue numbers 1-146 in SEQ ID NO. 1. For example, Derivative 2 as defined herein includes an N-terminal peptide of 15 amino acids in length. The residues in the N-terminal peptide are numbered negatively, starting from the residue attached to residue 1 in hIL-22, i.e. the first residue in the N-terminal peptide that is attached to residue 1 in hIL-22 is denoted "−1". Thus, as Derivative 2 has a fatty acid covalently attached at the 7$^{th}$ residue in the N-terminal peptide starting from position −1 and this is Cys, the covalent attachment site for Derivative 2 is herein referred to as "−7C". Naturally, however, the numbering used in the sequence listing for Derivative 2 starts from 1, in accordance with WIPO Standard ST.25; as such, position 1 in the sequence listing for Derivative 2 is actually residue −7 as referred to herein.

Two, three, four, five or more variations may be made within the native sequence to form the derivatives of the invention. For example, more than 10, 15, 20, 25, 50, 75, 100 or even more than 125 variations may be made in this regard. Any of residues 1-146 in the native sequence may be varied. Exemplary residues for variation are residues 1, 2, 3, 4, 5, 6, 7, 8, 9, 10, 11, 12, 13, 14, 15, 16, 17, 18, 19, 20, 21, 22, 24, 25, 26, 27, 29, 30, 32, 33, 34, 35, 36, 37, 38, 39, 40, 41, 42, 44, 45, 47, 48, 49, 50, 51, 52, 53, 54, 55, 56, 58, 59, 61, 62, 63, 64, 65, 67, 68, 69, 70, 71, 72, 73, 74, 75, 77, 78, 79, 82, 83, 84, 86, 88, 90, 91, 92, 93, 94, 95, 96, 97, 98, 99, 100, 102, 103, 104, 105, 106, 107, 108, 109, 110, 111, 112, 113, 114, 115, 116, 117, 118, 119, 120, 121, 122, 123, 124, 126, 127, 128, 129, 130, 132, 133, 134, 135, 137, 138, 139, 141, 143, 144, 145 and/or 146 in hIL-22. Variation at residues 1, 21, 35, 64, 113 and/or 114 is particularly advantageous.

The variations within the native sequence are typically amino acid substitutions. The term "substitution", as used herein, can mean the replacement of an amino acid in the native protein with another. They may be conservative or non-conservative substitutions.

Exemplary substitutions are A1C, A1G, A1H, P2C, P2H, I3C, I3H, I3V, S4H, 54N, S5H, S5T, H6C, H6R, C7G, R8G, R8K, L9S, D10E, D10S, K11C, K11G, K11V, S12C, N13C, N13G, F145, Q15C, Q15E, Q16V, P17L, Y18F, 119Q, T20V, N21C, N21D, N21Q, R22S, F24H, M25E, M25L, L26S, A27L, E29P, A30Q, L32C, L32R, A33C, A33N, D34F, N35C, N35D, N35H, N35Q, N36Q, T37C, T37I, D38L, V39Q, R40W, L41Q, I42P, E44R, K45A, F47T, H48G, H48R, G49N, V505, S51C, M52A, M52C, M52L, M52V, S53C, S53K, S53Y, E54D, E54F, R55Q, R55V, C56Q, L58K, M59I, Q61E, V62D, L63C, N64C, N64D, N64Q, N64W, F65G, L67Q, E69D, E69L, V705, L71C, F72D, F72L, P73C, P73L, Q74T, R77I, F78Q, Q79E, M82Y, Q83G, E84R, V86A, F88N, A90P, A90T, R91C, R91K, R91Y, L92R, S93Y, N94C, N94Q, R95K, R95Q, L96E, S97K, T98C, T98N, T98S, C99V, H100S, E102S, G103D, D104Y, D105Y, L106E, L106Q, H107L, H107N, I108L, Q109Y, R110C, R110K, N111K, V112E, Q113C, Q113R, K114C, K114R, L115V, K116Y, D117E, T118G, V119A, K120H, K121R, L122A, G123V, G126Y, E127C, I128V, K129V, G132Y, E133Q, L134P, D135M, L137D, F138R, M139L, M139R, L141Q, N143S, A144E, C145E, I146R and/or I146V. Advantageously, the substitution may be selected from the group consisting of A1C, A1G, A1H, N21C, N21D, N21Q, N35C, N35D, N35H, N35Q, N64C, N64D, N64Q, N64W, Q113C, Q113R, K114C and K114R. Surprisingly, substitutions as employed in the invention do not adversely affect IL-22 activity.

Particular combinations of substitutions include (i) A1G, N21D, N35D and N64D; (ii) A1G, I3V, 54N, 55T, H6R, R8K, D10E, K11V, T20V, H48R, M52A, S53K, E54D, R55Q, E69D, F72L, A90T, R91K, R95Q, T98S, E102S, L106Q, H107N, R110K, Q113R, K114R, D117E and I146V; (iii) A1G, I3V, 54N, 55T, H6R, R8K, D10E, K11V, T20V, H48R, M52A, S53K, E54D, R55Q, E69D, F72L, A90T, R91K, R95Q, T98S, E102S, L106Q, H107N, R110K, Q113R, K114R, D117E and I146V; (iv) A1G, N35Q and N64Q; (v) A1G and N64C; (vi) A1G and Q113C; (vii) A1G and K114C; (viii) A1G and M25L; (ix) A1G and M52L; (x) A1G and M139L; (xi) A1G and N36Q; (xii) A1G and D117E; (xiii) A1G and N21Q; (xiv) A1G and N35Q; (xv) A1G and N64Q; (xvi) A1G, N21Q and N35Q; (xvii) A1G, N21Q and N64Q; (xviii) A1G, N21Q, N35Q and N64Q; (xix) A1G and K11C; (xx) A1G and N13C; (xxi) N35Q and N64Q; (xxii) A1C, N35Q and N64Q; (xxiii) H6C, N35Q and N64Q; (xxiv) I3C, N35Q and N64Q; (xxv) P2C, N35Q and N64Q; (xxvi) L32C, N35Q and N64Q; (xxvii) N35Q, M52C and N64Q; (xxviii) N13C, N35Q and N64Q; (xxix) N21C, N35Q and N64Q; (xxx) N35Q, N64Q and N94C; (xxxi) N35Q, N64Q and P73C; (xxxii) N35Q, N64Q and Q113C; (xxxiii) N35Q, N64Q and R91C; (xxxiv) N35Q, N64Q and R110C; (xxxv) S12C, N35Q and N64Q; (xxxvi) N35Q, S51C and N64Q; (xxxvii) N35Q, S53C and N64Q; (xxxviii) N35Q, T37C and N64Q; (xxxix) N35Q, N64Q and T98C; (xxxx) Q15C, N35Q and N64Q; (xxxxi) N35C and N64Q; (xxxxii) H6C, N35Q and N64Q; (xxxxiii) A33C, N35Q and N64Q; and (xxxxiv) A1H, P2H, I3H, S4H, S5H, C7G, R8G, L9S, D10S, K11G, N13G, F145, Q15E, Q16V, P17L, 18F, Y19Q, N21Q, R22S, F24H, M25E, L26S, A27L, E29P, A30Q, L32R, A33N, D34F, N35H, T37I, D38L, V39Q, R40W, L41Q, I42P, E44R, K45A, F47T, H48G, G49N, V505, M52V, S53Y, E54F, R55V, C56Q, L58K, M59I, Q61E, V62D, L63C, N64W, F65G, L67Q, E69L, V705, L71C, F72D, P73L, Q74T, R77I, F78Q, Q79E, M82Y, Q83G, E84R, V86A, F88N, A90P, R91Y, L92R, S93Y, N94Q, R95K, L96E, S97K, T98N, C99V, H100S, G103D, D104Y, D105Y, L106E, H107L, I108L, Q109Y, R111K, V112E, L115V, K116Y, D117E, T118G, V119A, K120H, K121R, L122A, G123V, G126Y, E127C, I128V, K129V, G132Y, E133Q, L134P, D135M, L137D, F138R, M139R, L141Q, N143S, A144E, C145E and I146R. Any and all combinations of substitutions are envisaged and form part of the invention.

A derivative of the first aspect may typically comprise an amino acid substitution whereby Cys is substituted for a native residue, optionally in any of the positions identified above, such as position 1, 2, 3, 6, 11, 12, 13, 15, 21, 32, 33, 35, 37, 51, 52, 53, 63, 64, 71, 73, 91, 94, 98, 110, 113, 114 and/or 127. Advantageously, the IL-22 protein included in a derivative of the first aspect comprises a Cys residue at position 1 of hIL-22. An A1C substitution combined with substitutions in two glycosylation sites at positions 35 and 64 is particularly advantageous, as it leads to faster uptake without adversely affecting potency or half-life (see Derivatives 6 and 10 in Examples 1 and 2).

Alternatively, or in addition, the variations within the native sequence may be amino acid insertions. Up to five, 10, 15, 20, 25, 30, 35, 40, 45 or even up to 50 amino acids may be inserted within the native sequence. Trimers, pentamers, septamers, octamers, nonamers and 44-mers are particularly advantageous in this regard. Exemplary sequences are shown in Table 1. Insertions can be made at any location in the native sequence, but those in helix A (for example, at residue 30), loop CD (for example, at residue 75), helix D (for example, at residue 85) and/or helix F (for example, at residue 124) are preferred.

TABLE 1

Sequence of exemplary amino acid insertions

| n-mer | Exemplary amino acid sequence | SEQ ID NO. |
|---|---|---|
| Trimer | E-T-S | n/a |
| Pentamer | R-V-Q-F-Q or C-V-E-I-P | 2, 3 |
| Septamer | G-S-G-S-G-S-C | 4 |
| Octamer | I-E-A-L-T-P-H-S or Y-G-Q-R-Q-W-K-N | 5, 6 |
| Nonamer | V-F-I-I-N-N-S-L-E | 7 |
| 44-mer | R-A-A-S-A-G-S-Y-S-E-W-S-M-T-P-R-F-T-P-W-W-E-T-K-I-D-P-P-V-M-N-I-T-Q-V-N-G-S-L-L-V-I-L-H | 8 |

Sequence variations relative to the amino acid sequence of hIL-22, if present, typically include an extension, such as the addition of a peptide at the N-terminal end. The peptide may consist of up to five, 10, 15, 20, 25, 30, 35, 40, 45 or even up to 50 amino acids. Monomers, trimers, octamers, 13-mers, 15-mers, 16-mers, 21-mers, 28-mers are particularly advantageous in this regard. Exemplary sequences are shown in Table 2. Suitably, the IL-22 protein included in a derivative of the first aspect comprises an N-terminal G-P-G. In a particularly preferred example, the derivative of the first aspect comprises both a Cys residue at position 1 of hIL-22 (SEQ ID NO. 1) and an N-terminal G-P-G. This has been found to create a derivative with a very good half-life and potency (see Derivatives 1, 3 and 5 in Examples 1 and 2).

TABLE 2

Sequence of exemplary N-terminal peptides

| n-mer | Exemplary amino acid sequence | SEQ ID NO. |
|---|---|---|
| Monomer | C, G or M | n/a |
| Trimer | G-P-G | n/a |
| Octamer | G-P-A-C-E-P-E-E | 9 |
| 13-mer | G-G-S-S-G-S-G-S-E-V-L-F-Q | 10 |
| 15-mer | G-P-G-S-G-S-G-S-C-G-S-G-S-G-S | 11 |

TABLE 2-continued Sequence of exemplary N-terminal peptides

| n-mer | Exemplary amino acid sequence | SEQ ID NO. |
|---|---|---|
| 16-mer | G-G-S-S-G-S-G-S-E-V-L-F-Q-G-P-G | 12 |
| 21-mer | G-G-S-S-G-S-G-S-E-V-L-F-Q-G-P-A-C-E-P-E-E | 13 |
| 28-mer | G-G-S-S-G-S-G-S-E-V-L-F-Q-G-P-G-S-G-S-G-S-C-G-S-G-S-G-S | 14 |

Sequence variations relative to the amino acid sequence of hIL-22, if present, may include the addition of a peptide at the C-terminal end. The peptide may consist of up to five, 10, 15, 20, 25, 30, 35, 40, 45 or even up to 50 amino acids. A septamer is particularly advantageous in this regard, optionally having the amino acid sequence, G-S-G-S-G-S-C (SEQ ID NO. 15).

The derivatives of the invention may include both an N-terminal and a C-terminal peptide in addition to the native or variant hIL-22 amino acid sequence as herein described. Any combination of the N- and C-terminal peptides described herein is envisaged and expressly included in the invention.

It will be appreciated that the invention extends to any derivative of IL-22, which comprises a fatty acid covalently attached to hIL-22 or a variant thereof. The "variant" can be a protein having at least 10% sequence identity with hIL-22. In an embodiment, the variant has at least 20%, or even at least 30%, sequence identity with hIL-22. The variant may have "substantially the amino acid sequence" of hIL-22, which can mean a sequence that has at least 40% sequence identity with the amino acid sequence of hIL-22. Accordingly, in an embodiment, a derivative of the first aspect has at least 50%, at least 60%, at least 70%, at least 80%, at least 90%, at least 95% or 100% amino acid sequence identity with hIL-22. Exemplary IL-22 protein variants, which are incorporated in the particular derivatives of the invention disclosed in the experimental section, are set forth in SEQ ID NOs. 16-21.

The skilled technician will appreciate how to calculate the percentage identity between two amino acid sequences. An alignment of the two sequences must first be prepared, followed by calculation of the sequence identity value. The percentage identity for two sequences may take different values depending on: (i) the method used to align the sequences, for example, ClustalW, BLAST, FASTA, Smith-Waterman (implemented in different programs), or structural alignment from 3D comparison; and (ii) the parameters used by the alignment method, for example, local versus global alignment, the pair-score matrix used (for example, BLOSUM62, PAM250, Gonnet etc.) and gap-penalty, for example, functional form and constants.

Having made the alignment, there are many different ways of calculating percentage identity between the two sequences. For example, one may divide the number of identities by: (i) the length of shortest sequence; (ii) the length of alignment; (iii) the mean length of sequence; (iv) the number of non-gap positions; or (iv) the number of equivalenced positions excluding overhangs. Furthermore, it will be appreciated that percentage identity is also strongly length-dependent. Therefore, the shorter a pair of sequences is, the higher the sequence identity one may expect to occur by chance.

Hence, it will be appreciated that the accurate alignment of amino acid sequences is a complex process. The popular multiple alignment program ClustalW [48,49] is a preferred way for generating multiple alignments of proteins in accordance with the invention. Suitable parameters for ClustalW may be as follows: For protein alignments: Gap Open Penalty=10.0, Gap Extension Penalty=0.2, and Matrix=Gonnet. For DNA and Protein alignments: END-GAP=−1, and GAPDIST=4. Those skilled in the art will be aware that it may be necessary to vary these and other parameters for optimal sequence alignment.

Preferably, calculation of percentage identities between two amino acid sequences may then be calculated from such an alignment as (N/T)*100, where N is the number of positions at which the sequences share an identical residue, and T is the total number of positions compared including gaps but excluding overhangs. Hence, a most preferred method for calculating percentage identity between two sequences comprises (i) preparing a sequence alignment using the ClustalW program using a suitable set of parameters, for example, as set out above; and (ii) inserting the values of N and T into the following formula: Sequence Identity=(N/T)*100.

Alternative methods for identifying similar sequences will be known to those skilled in the art.

Suitably, a derivative of the first aspect comprises 200 amino acids or less. For example, the derivative comprises less than 190, less than 180, less than 170, less than 160 or even less than 150 amino acids. Suitably, the derivative will comprise at least 146 amino acids, however, this being the number of amino acids in hIL-22. It may comprise at least 150 amino acids, at least 160 amino acids, at least 170 amino acids or even at least 180 amino acids.

The derivatives of the invention can comprise proteins of any length within the above ranges, but they will typically be 146-180 amino acids in length.

The derivatives of the invention, whether having the native or a variant amino acid sequence, include a fatty acid covalently attached to the IL-22 protein. The fatty acid is typically covalently attached to the IL-22 protein by a linker. The fatty acid and linker are suitably connected to each other via an amide bond, and the linker is covalently attached to the IL-22 protein. The fatty acid and linker may thus be present as a side chain on the IL-22 protein. It was surprising to the inventors that a covalently attached fatty acid does not adversely affect IL-22 activity. It was particularly surprising that fatty acid attachment is associated with additional advantages, such as prolongation of half-life.

The fatty acid may be any suitable fatty acid. In particular, the fatty acid may be of Formula I:

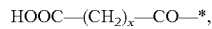

HOOC—$(CH_2)_x$—CO—*, wherein x is an integer in the range of 10-18, optionally 12-18, 14-16 or 16-18, and * designates a point of attachment to the IL-22 protein or linker. It may be a fatty diacid, such as a C12, C14, C16, C18 or C20 diacid. Advantageously, the fatty acid is a C16 or C18 diacid, and most advantageously it is a C18 diacid.

For example, —$(CH_2)_x$— in Formula I may be a straight alkylene in which x is 10. This fatty acid may be conveniently referred to as C12 diacid, i.e. a fatty di-carboxylic acid with 12 carbon atoms. Alternatively, —$(CH_2)_x$— in Formula I may be a straight alkylene in which x is 12. This fatty acid may be conveniently referred to as C14 diacid, i.e.

a fatty di-carboxylic acid with 14 carbon atoms. In a similar fashion, —(CH$_2$)$_x$— in Formula I may be a straight alkylene in which x is 14 (C16 diacid), 16 (C18 diacid) or 18 (C20 diacid). Suitably, a derivative of the first aspect includes a C14, C16, C18 or C20 diacid; more suitably, a C16 or C18 diacid, and even more suitably a C18 diacid.

The diacid may be capable of forming non-covalent associations with albumin, thereby promoting circulation of the derivative in the blood stream. The shorter diacids (e.g. C16 diacid) have lower albumin affinity and thus a shorter half-life than the longer diacids (e.g. C18 diacid). However, they are still long acting derivatives with an expected half-life in man of over one day.

Fatty acid attachment will, in itself, also stabilise the IL-22 protein against proteolytic degradation. The resulting half-life is typically similar to that of IL-22-Fc fusions (i.e. greatly improved compared to hIL-22).

The derivatives of the first aspect may comprise particular combinations of a fatty acid and IL-22 protein. For example, a C14, C16, C18 or C20 diacid may be attached to an IL-22 protein comprising a Cys residue at position 1 of hIL-22 and/or an N-terminal G-P-G. In one example, a derivative of the first aspect comprises a C18 diacid and the IL-22 protein comprises both a Cys residue at position 1 of hIL-22 and an N-terminal G-P-G.

As above, the fatty acid is suitably connected to a linker, which is attached to the IL-22 protein. The linker may comprise several linker elements, including one or more amino acids such as one or more Glu and/or Lys residues. The linker may include an oxyethylene glycine unit or multiple linked oxyethylene glycine units, optionally 2-5 such units, advantageously 2 units. One or more OEG residues, C2DA and/or Ac groups may alternatively or additionally be included. The linker may comprise a Cys-reactive unit. A "Cys-reactive unit", as used herein, can mean a functional unit that is able to react with the sulphur atom of a Cys to create a carbon-sulphur covalent bond. The Cys-reactive unit can have any of several forms, but suitably includes a carbon atom attached to a leaving group, which leaving group becomes displaced by the sulphur atom of the Cys during formation of the carbon-sulphur bond. The leaving group may be a halogen, optionally a bromine atom. This bromide leaving group can be alpha to an actamide functional group; advantageously it is a bromo-acetamide functional group. The leaving group may alternatively be a functionalised hydroxyl group of the form mesylate or tosylate, or an unfunctionalised hydroxyl group. Further, the leaving group can be a maleimide or other functional group. Exemplary linkers include γGlu-OEG- OEG-C$_2$DA-Ac, γGlu-γGlu-γGlu-γGlu-OEG- OEG-εLys-αAc and γGlu-OEG-OEG-εLys-αAc, but any suitable linker may be employed.

The fatty acid, or linker, may be attached to any amino acid residue in the IL-22 protein. Exemplary in this regard are residues −7, −5, 1, 6, 33, 113, 114 and 153 in or relative to the hIL-22 amino acid sequence. The native residue is typically substituted with Cys or Lys to enable attachment of the fatty acid or linker. Alternatively the fatty acid or linker can be attached at a native Cys or Lys residue. Suitably, the fatty acid or linker is attached to a Cys residue substituted at position 1, 6, 33, 113 or 114 of hIL-22 or to a Cys residue at position −5, −7 or 153 relative to hIL-22. In particular, the fatty acid or linker may be attached to a Cys residue substituted at position 1 of hIL-22.

The attachment of the fatty acid or linker to the IL-22 protein is a covalent attachment. For example, a Cys-reactive fatty acid or linker may be used to attach the fatty acid or linker to a Cys residue in the IL-22 protein. The fatty acid or linker may be covalently attached to the sulphur atom of the Cys residue via a thioether bond. Alternatively, a Lys-reactive fatty acid or linker may be used to attach the fatty acid or linker to a Lys residue in the IL-22 protein. The fatty acid or linker may alternatively be covalently attached to the free amine (—NH$_2$) group in the N-terminus of the IL-22 protein (irrespective of the amino acid in position 1). Attachment can proceed as with Cys attachment, albeit with sub-stoichiometric amounts of fatty acid or linker containing a suitable N-reactive species. The fatty acid or linker may be presented in the form of an aldehyde (the N-reactive species) and be covalently attached to the free amine employing a classically known reductive amination.

A derivative of the first aspect thus suitably comprises a C14, C16, C18 or C20 diacid attached by a linker to a variant of hIL-22, wherein the variant comprises an N-terminal G-P-G and a Cys residue at position 1 of hIL-22 and the linker is optionally attached to the Cys residue.

Exemplary derivatives of the first aspect comprise an IL-22 protein as set forth in any of SEQ ID NOs. 16-21. Particularly advantageous derivatives are shown in Table 3, illustrated in FIGS. 1-4 and exemplified herein.

TABLE 3

Exemplary derivatives of IL-22

| ID | Sequence variations | SEQ ID NO. | Covalent attachment site | Linker | Fatty acid |
|---|---|---|---|---|---|
| Derivative 1 | A1C substitution & G-P-G N-terminal peptide | 16 | 1C | γGlu-OEG-OEG-C$_2$DA-Ac | C18 diacid |
| Derivative 2 | G-P-G-S-G-S-G-S-C-G-S-G-S-G-S N-terminal peptide | 17 | −7C | γGlu-OEG-OEG-C$_2$DA-Ac | C18 diacid |
| Derivative 3 | A1C substitution & G-P-G N-terminal peptide | 16 | 1C | γGlu-OEG-OEG-C$_2$DA-Ac | C16 diacid |
| Derivative 4 | G-P-G-S-G-S-G-S-C-G-S-G-S-G-S N-terminal peptide | 17 | −7C | γGlu-OEG-OEG-C$_2$DA-Ac | C16 diacid |

TABLE 3-continued

Exemplary derivatives of IL-22

| ID | Sequence variations | SEQ ID NO. | Covalent attachment site | Linker | Fatty acid |
|---|---|---|---|---|---|
| Derivative 5 | A1C substitution & G-P-G N-terminal peptide | 16 | 1C | γGlu-γGlu-γGlu-γGlu-OEG-OEG-εLys-αAc | C14 diacid |
| Derivative 6 | A1C, N35Q, N64Q substitutions & G-P-G N-terminal peptide | 18 | 1C | γGlu-OEG-OEG-C$_2$DA-Ac | C18 diacid |
| Derivative 7 | A1C, N35Q, N64Q substitutions | 19 | 1C | γGlu-OEG-OEG-C$_2$DA-Ac | C18 diacid |
| Derivative 8 | H6C, N35Q, N64Q substitutions & G N-terminal peptide | 20 | 6C | γGlu-OEG-OEG-C$_2$DA-Ac | C18 diacid |
| Derivative 9 | A33C, N35Q, N64Q substitutions | 21 | 33C | γGlu-OEG-OEG-C$_2$DA-Ac | C18 diacid |
| Derivative 10 | A1C, N35Q, N64Q substitutions & G-P-G N-terminal peptide | 18 | 1C | γGlu-OEG-OEG-C$_2$DA-Ac | C16 diacid |

Figure 1B:
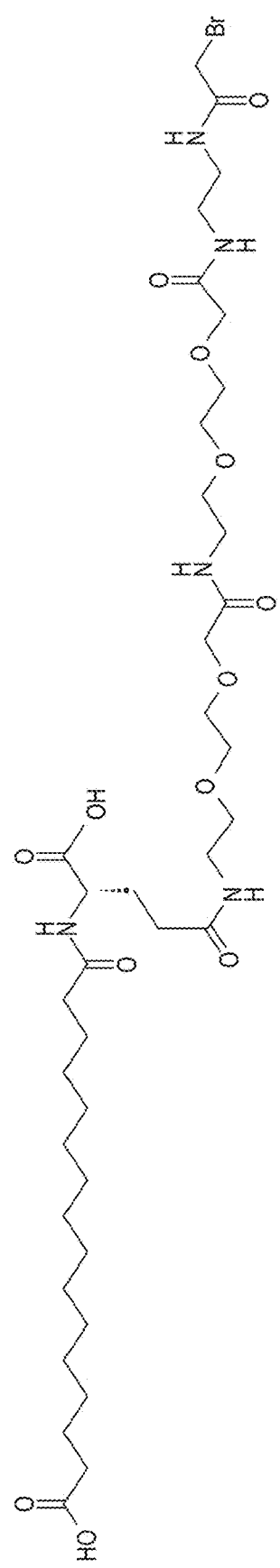
Figure 1C:
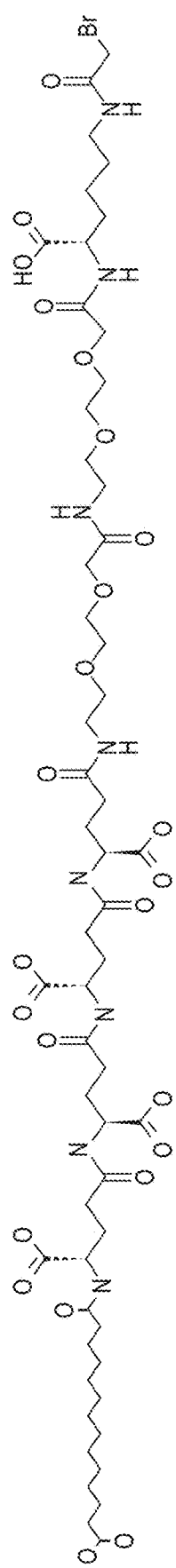

FIG. 1A illustrates a C18 diacid connected to a linker comprising a Cys-reactive unit. This is the fatty acid and linker (side chain) used in Derivatives 1, 2 and 6-9. FIG. 1B illustrates a C16 diacid connected to a linker comprising a Cys-reactive unit. This is the fatty acid and linker (side chain) used in Derivatives 3, 4 and 10. FIG. 1C illustrates a C14 diacid connected to a linker comprising a Cys-reactive unit. This is the fatty acid and linker (side chain) used in Derivative 5.

Figure 2:
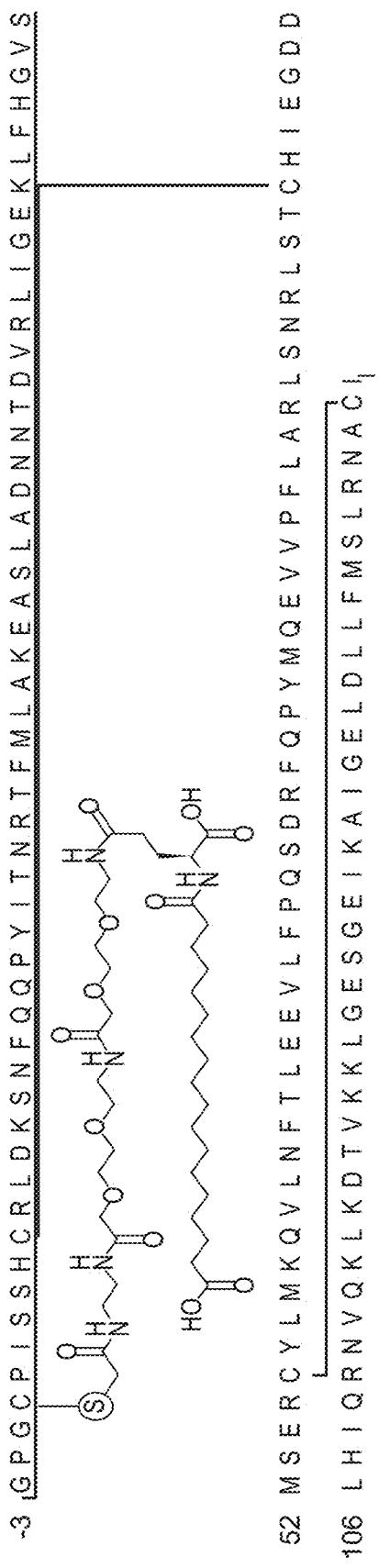
FIG. 2 illustrates the structure of a derivative of the invention identified herein as Derivative 1.
Figure 3:
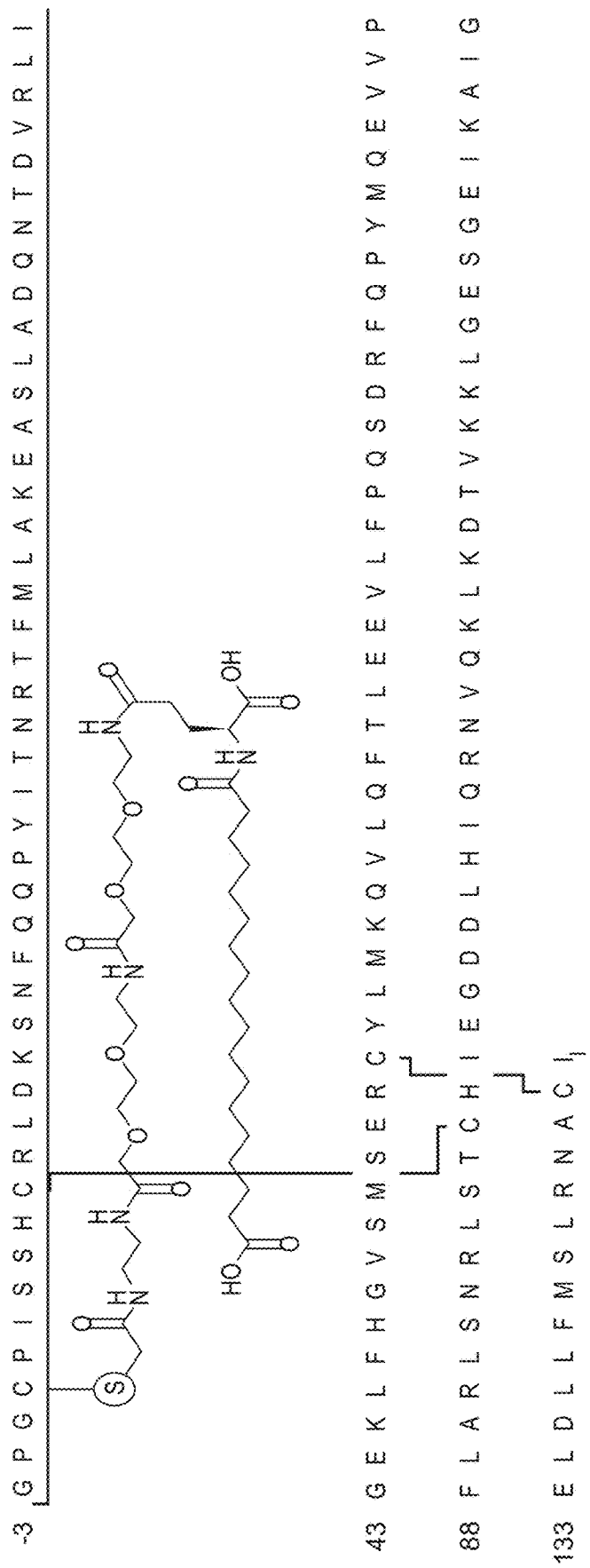
FIG. 3 illustrates the structure of a derivative of the invention identified herein as Derivative 6.
Figure 4:
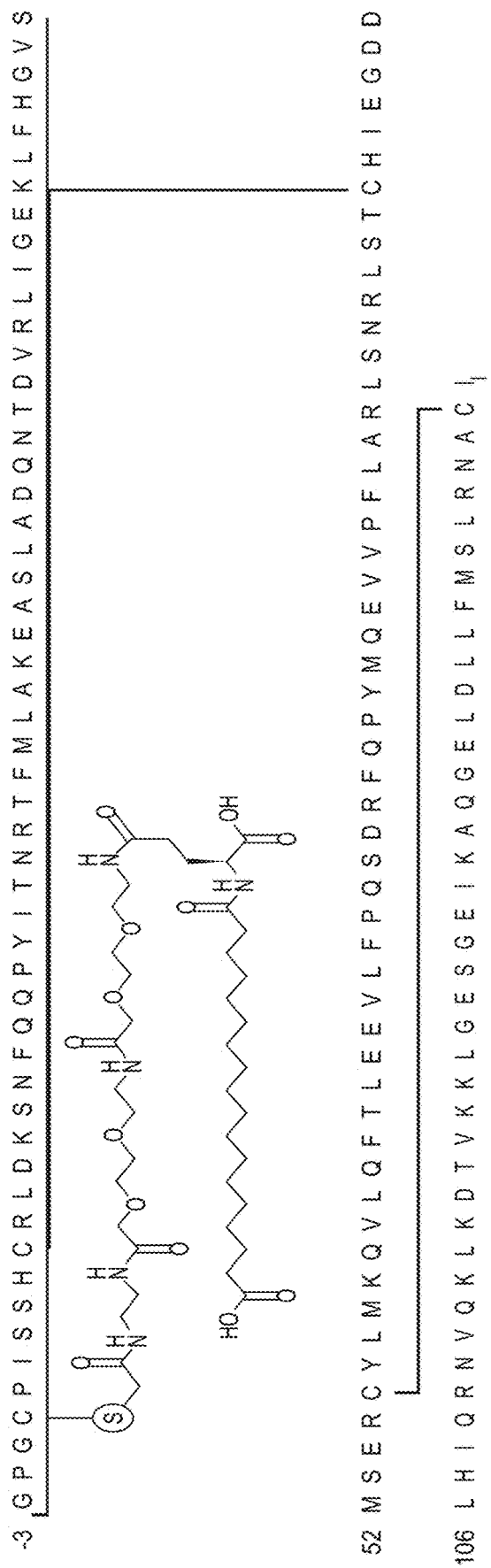
FIG. 4 illustrates the structure of a derivative of the invention identified herein as Derivative 10.

Derivatives 1, 6 and 10 are illustrated in FIGS. 2-4, respectively.

The derivatives of the invention may exist in different stereoisomeric forms and the invention relates to all of these.

According to a second aspect of the invention, there is provided a process for preparing a derivative of the first aspect comprising covalently attaching a fatty acid to an IL-22 protein.

The process may be used to produce any of the different derivatives of IL-22 described or envisaged herein, but it is particularly advantageous when a fatty acid is covalently attached to a variant IL-22 protein. Thus, in an embodiment, the IL-22 protein employed in the second aspect is a substituted form of hIL-22, optionally substituted at position 1, 21, 35, 64, 113 and/or 114. Exemplary substitutions include A1C, A1G, A1H, N21C, N21D, N21Q, N35C, N35D, N35H, N35Q, N64C, N64D, N64Q, N64W, Q113C, Q113R, K114C and/or K114R. Preferably, the IL-22 protein is substituted with a Cys residue at position 1.

The fatty acid can be obtained by any means known in the art, including recombinant means. Suitable fatty acids are commercially available or readily derived from available starting materials using standard chemical synthesis.

The IL-22 protein can be obtained by any means known in the art, including recombinant means. The production of recombinant hIL-22 has been previously described and is well-known in the art. Desired variant IL-22 proteins can be produced in a similar manner. An experienced investigator in the field would be readily able to identify suitable nucleic acid sequences that encode the desired variant IL-22 proteins. The skilled person would hence be readily able to execute this part of the invention, based upon the existing knowledge in the art. Suitably, the IL-22 proteins are produced in mammalian systems, such as in Chinese hamster ovary (CHO) cells, using standard techniques. A polyhistidine tag (His-tag) may be employed to aid affinity purification of the recombinant proteins.

In this regard, IL-22 proteins as used in the invention can be prepared using a post expression cleavable His-tag- an N- or C-terminal addition of less than 10, preferably six, histidine residues that can be purified by affinity to a nickel column. The His-tag is linked to the N- or C-terminal of the protein via a linker that can be digested by a known protease to leave the free IL-22 protein. The cleavable His-tag can have the amino acid sequence, HHHHHHGGSSGSG-SEVLFQ (SEQ ID NO. 25), and the protease-cleavable linker can be a tobacco etch virus (TEV) linker, whose consensus sequence for the native cut sites is ENLYFQ\S (SEQ ID NO. 26), where '\' denotes the cleaved peptide bond or a human rhinovirus-14 3C (HRV14-3C) protease cleavable linker with EVLFQ consensus cleavage site. Cleavage may be achieved by incubating approximately 10 μg protease with 2.5 protein and 10 mM 2-mercaptoethanol at room temperature for 4 h.

To further illustrate the invention, a representative process for protein preparation is provided as follows. The process involves preparing a plasmid DNA that encodes the desired amino acid sequence of the IL-22 protein. This plasmid can be transiently transfected into a cell line, for example CHO-K1, which is allowed to grow in a relevant medium before growth is increased by the addition of a known enhancer. The secreted IL-22 protein can then be harvested through known methods of centrifugation and sterile filtration before the protein is purified on a nickel column. Following concentration and buffer exchange the His-tag is removed using a HRV14-3C protease before alkylation with a fatty acid (described further below) and final purification and buffer exchange. Analysis of the final product using SDS-PAGE, size exclusion chromatography or liquid chromatography with tandem mass spectrometry (LC-MS-MS) with, or without, deglycosylation can be used to ensure the quality of the final product.

The fatty acid can be covalently attached to the IL-22 protein either directly or using a linker as described for the first aspect. The linker can be obtained by any means known in the art. A representative method for preparing the fatty acid and linker, if employed, is as follows (exemplified by the C16 diacid used in Derivative 10, but any derivative could be made using a similar method).

A solution of N-(benzyloxycarbonyloxy) succinimide (100 g, 401 mmol) in dichloromethane (500 ml) is added to a solution of ethylene diamine (189 ml, 2.81 mol) in dichloromethane (750 ml). After 30 minutes the suspension is filtered, washed and concentrated in vacuo. The residue is diluted with toluene (750 ml), washed and extracted with dichloromethane (4×200 ml), dried over anhydrous sodium sulphate, filtered, concentrated in vacuo and diluted with hexanes (200 ml). A 4 M solution of hydrogen chloride in ether (100 ml, 400 mmol) is added to the solution, the resulting suspension concentrated in vacuo and diluted with hexanes (1 1). The precipitated solid is filtered, washed with hexanes and dried in vacuo to give (2-aminoethyl) carbamic acid benzyl ester hydrochloride as a white powder.

2-Chlorotrityl resin 100-200 is loaded with {2-[2-(9H-fluoren-9-ylmethoxycarbonylamino)-ethoxy]-ethoxy}-acetic acid (Fmoc-Ado-OH, 17.5 g, 45.4 mmol) The Fmoc group is removed and a solution of 0-6-chloro-benzotriazol-1-yl)-N,N,N',N'-tetramethyluronium tetrafluoroborate (TCTU, 24.2 g, 68.1 mmol) and N,N-diisopropylethylamine (21.4 ml, 123 mmol) in N,N dimethylformamide (140 ml) is added to the resin and the mixture shaken for one hour. The resin is filtered and washed. The Fmoc group is removed by treatment with 20% piperidine as before. The resin is washed as before.

A solution of (S)-2-(fluoren-9-ylmethoxycarbonylamino)-pentanedioic acid 1-tert-butyl ester (Fmoc-Glu-OtBu, 29.0 g, 68.1 mmol), TCTU (24.2 g, 68.1 mmol) and N,N-diisopropylethylamine (21.4 ml, 123 mmol) in N,N dimethylformamide (140 ml) is added to the resin and the mixture shaken for one hour. The resin is filtered and washed as before. The Fmoc group is removed by treatment with 20% piperidine as before. The resin is washed as before.

A solution of 16-tert-butoxy)-16-oxohexadecanoic acid (23.3 g, 68.1 mmol), TCTU (24.2 g, 68.1 mmol) and N,N diisopropylethylamine (21.4 ml, 123 mmol) in N,N-dimethylformamide/dichloromethane mixture (4:1, 200 ml) is added to the resin. The resin is shaken for one hour, filtered and washed with N,N-dimethylformamide (3×250 ml), dichloromethane (2×250 ml), methanol (2×250 ml) and dichloromethane (6×250 ml). The product is cleaved from the resin by treatment with 2,2,2-trifluoroethanol (250 ml) for 18 hours. The resin is filtered off and washed with dichloromethane (2×250 ml), 2-propanol/dichloromethane mixture (1:1, 2×250 ml), 2-propanol (250 ml) and dichloromethane (3×250 ml).

The solutions are combined, the solvent is evaporated and crude product purified by flash column chromatography. Pure (S)-22-(tert-butoxycarbonyl)-41,41-dimethyl-10,19,24,39-tetraoxo-3,6,12,15,40-pentaoxa-9,18,23-triazadotetracontanoic acid is dried in vacuo and obtained as a pale yellow thick oil.

2-(7-Aza-1H-benzotriazole-1-yl)-1,1,3,3-tetramethyluronium hexafluorophosphate (HATU, 11.4 g, 30.1 mmol) and triethylamine (8.77 ml, 62.9 mmol) are subsequently added to a solution of (S)-22-(tert-butoxycarbonyl)-41,41-dimethyl-10,19,24,39-tetraoxo-3,6,12,15,40-pentaoxa-9,18,23-triazadotetracontanoic acid (22.4 g, 27.4 mmol) in dry dichloromethane (110 ml). Triethylamine (72 ml, 41.0 mmol) is added to a suspension of (2-amino-ethyl)-carbamic acid benzyl ester hydrochloride (6.94 g, 30.1 mmol) in dry dichloromethane (165 ml) and the resulting mixture is added to the above solution. The mixture is stirred at room temperature overnight and then evaporated to dryness. The residue is re-dissolved and washed; dried over anhydrous sodium sulphate and evaporated column chromatography (Silicagel 60, 0.040-0.060 mm; eluent: dichloromethane/methanol 95:5) to afford 15-[(S)3-(2-{2-[(2-{2-[(2-benzyloxycarbonylamino-ethylcarbamoyl)-methoxy]-ethoxy}ethyl-carbamoyl)methoxy]ethoxy)-ethylcarbamoyl)-1-tert-butoxycarbonylpropylcarbamoyl]-pentadecanoic acid tert-butyl ester as a pale yellow thick oil.

Palladium on carbon (10%, 1.27 g, 1.20 mmol) is added to a solution of the above compound (23.8 g, 24.0 mmol) in methanol (350 ml) and the resulting mixture hydrogenated at normal pressure for four hours. The catalyst is filtered off and the filtrate evaporated to dryness. The residue is evaporated several times from dichloromethane in order to remove residues of methanol and dried in vacuo to yield tert-butyl (S)-1-amino-25-tert-butoxycarbonyl)-4,13,22,27-tetraoxo-6,9,15,18-tetraoxa-3,12,21,26-tetraazadotetracontan-42-oate as a thick colourless oil.

N,N-Diisopropylethylamine (4.98 ml, 28.6 mmol) is added to a solution of the above amine (20.5 g, 23.8 mmol) in dry dichloromethane (290 ml) at −30° C. under argon. Bromoacetyl bromide (2.48 ml, 28.6 mmol) is added dropwise and the resulting solution is stirred at −30° C. for an additional three hours. The cooling bath is removed, the mixture is stirred at room temperature for one hour, and the solvent is removed in vacuo. The residue is re-dissolved in ethyl acetate (450 ml) and washed with 5% aqueous solution of citric acid (300 ml). The phases are separated within one hour. The organic layer is left to separate overnight to give three phases. The clear aqueous layer is removed and the residual two phases shaken with a saturated aqueous solution of potassium bromide (100 ml). The phases are left to separate overnight, the aqueous phase removed and the organic phase dried over anhydrous sodium sulphate. The solvent is removed in vacuo and the residue purified by flash column chromatography:dichloromethane/methanol 95:5) to afford tertbutyl(S)-1-bromo-28-tert-butoxycarbonyl)-2,7,16,25,30-pentaoxo-9,12,18,21-tetraoxa-3,6,15,24,29-pentaazapenta-tetracontan-45-oate as a colourless solid.

The above compound (19.5 g, 19.8 mmol) is dissolved in trifluoroacetic acid (120 ml) and the resulting solution is stirred at room temperature for 1.5 hours. Trifluoroacetic acid is removed in vacuo and the residue is evaporated from dichloromethane (6×200 ml). Diethyl ether (200 ml) is added to the oily residue and the mixture stirred overnight to give a suspension. The solid product is filtered, washed with diethyl ether and hexanes and dried in vacuo to afford the desired product 15-{(S)-1-carboxy3-[2-(2-{[2-(2-{[2-(2-Bromoacetylamino)ethylcarbamoyl]methoxy}-ethoxyethyl-carbamoyl]methoxy}ethoxyl-ethylcarbamoyl]propylcarbamoyl}pentadecanoic acid as a white powder.

Covalent attachment of the fatty acid or linker to the IL-22 protein may be carried out using standard procedures in the art. The linker, if employed, thus enables covalent attachment of the IL-22 protein to the fatty acid. By way of a non-limiting example, a Cys-reactive fatty acid or linker may be reacted with the sulphur atom of a Cys residue in the IL-22 protein, so forming a thioether bond. Suitable conditions for the covalent attachment step may be exemplified as follows: Tris in water is added to IL-22 protein (70 mg) in Tris and NaCl-buffer (1.35 mg/ml), to adjust to pH 8. Bis(p-sulfonatophenyl)-phenylphosphine dihydrate dipotassium (BSPP) salt (12 mg), dissolved in water, is added and stirred gently for four hours at room temperature. 15-{(S)-1-Carboxy-3-[2-(2-{[2-{[2-(2-bromoacetylamino)-ethylcarbamoyl]ethoxy}ethoxy)ethylcarbamoyl]methoxy}ethoxy) ethylcarbamoyl]propyl-carbamoyl}pentadecanoic acid (19 mg, 0.022 mmol) in ethanol (0.5 ml) is added and the mixture stirred gently overnight. MiliQ water (150 ml) is added to lower the conductivity to 2.5 mS/cm. The mixture is then purified using anion exchange on a MonoQ 10/100 GL column using binding buffer (20 mM Tris, pH 8.0), elution buffer (20 mM Tris, 500 mM NaCl, pH 8.0), flow 6 ml and a gradient of 0-80% elution buffer over 60 column volumes.

The derivatives of the invention may be purified using any suitable procedure known in the art, such as chromatography, electrophoresis, differential solubility or extraction.

As described herein, the inventors were surprised to find that fatty acids could be covalently attached to an IL-22 protein whilst maintaining biological activity. It was particularly surprising that such a minimal modification to IL-22 could result in high potency (close to hIL-22) combined with a very long circulatory half-life. This particular combination of properties may be highly desirable.

The potency of the derivatives may be determined in an in vitro assay with whole cells expressing human IL-22 receptors. For example, the response of the human IL-22 receptors may be measured using baby hamster kidney (BHK) cells overexpressing IL-22R1, IL-10R2 and a phospho-STAT3 (pSTAT3) responsive reporter gene. Alternatively, HepG2 cells endogenously expressing the IL-22 receptor may be used. Activation of the receptors leads to activation of the STAT3 signaling pathway, which can be measured using a luciferase reporter gene with a STAT3-induced promoter or by assaying pSTAT3, for example. Non-limiting examples of such assays are described in Example 2. In vivo potency may be determined in animal models or in clinical trials, as is known in the art.

The half maximal effective concentration ($EC_{50}$) value is often used as a measure of the potency of a drug. As this represents the concentration of drug required to produce 50% of the maximal effect, the lower the $EC_{50}$ value, the better the potency. The derivatives of the invention suitably have a potency ($EC_{50}$ value) measured using IL-22 receptor-mediated STAT3 activation in cells of below 1.5 nM, below 1.25 nM, below 1 nM, below 0.75 nM, below 0.5 nM, below 0.25 nM or even below 0.1 nM (e.g. determined as described in Example 2). The derivatives of the invention suitably have a potency ($EC_{50}$ value) measured by assaying pSTAT3 in cells of below 15 nM, below 12 nM, below 10 nM, below 7 nM or even below 5 nM (e.g. determined as described in Example 2).

Advantageously, the potency of the derivatives of IL-22 may be higher than that of IL-22-Fc fusions. For example, Genentech has reported a 34-fold reduction in in vitro potency for its IL-22-Fc fusion, UTTR1147A, compared to hIL-22 (Stefanich et al., *Biochem Pharmacol*, 2018, 152: 224-235). By contrast, covalent attachment of a fatty acid to hIL-22 has been shown to cause only a seven-fold reduction in potency (see Derivative 1 in the Examples).

Whilst both IL-22-Fc fusions and the derivatives of the present invention may be comparable in terms of their improved half-life over hIL-22 and biological function in at least some settings, the derivatives of the invention may have the additional advantage of minimal loss of potency.

The circulatory elimination half-life ($T_{1/2}$) of the derivatives may be determined in vivo by administering the derivatives subcutaneously or intravenously in a suitable animal model, such as a mouse, rat or minipig. Suitable methods are described in Example 1. By way of a non-limiting example, the derivatives of the first aspect have a circulatory half-life after subcutaneous or intravenous administration to mice of at least one hour, at least three hours, at least five hours or even at least eight hours. The derivatives may have a circulatory half-life after subcutaneous or intravenous administration to rats of at least three hours, at least five hours, at least eight hours, at least 10 hours or even at least 13 hours. The derivatives may have a circulatory half-life after subcutaneous or intravenous administration to minipigs of at least 25 hours, at least 40 hours, at least 70 hours or even at least 100 hours (all determined, e.g. as described in Example 1).

As exemplified herein, the inventors have also found that the derivatives of the invention are absorbed rapidly in vivo. Advantageously, absorption of the derivatives may occur faster than that of IL-22-Fc fusions. Mean absorption time is an accurate parameter for measuring uptake because it is independent of dose and maximum plasma concentration following drug administration. It can be calculated based upon mean residence time, i.e. the time that a drug spends in the body prior to elimination once absorption has been completed. The derivatives of the invention suitably have a mean absorption time of below 100 h, below 90 h, below 80 h, below 70 h or even below 60 h (e.g. determined as described in Example 1).

The derivatives of the invention also have good biophysical properties, such as high physical stability and/or solubility, which may be measured using standard methods in the art.

Therefore, according to a third aspect of the invention, there is provided a pharmaceutical composition comprising a derivative of the first aspect and a pharmaceutically acceptable vehicle.

A pharmaceutical composition of the third aspect may comprise any of the different derivatives of IL-22 described or envisaged herein. Suitably, it comprises one of the derivatives of IL-22 identified herein as Derivative 1-10.

A derivative of the first aspect, or a pharmaceutical composition of the third aspect, will suitably demonstrate increased circulatory elimination half-life compared to hIL-22. Advantageously it will demonstrate increased circulatory elimination half-life compared to hIL-22 by at least 50%, at least 75%, at least 100% or more.

The pharmaceutical compositions of the third aspect may be prepared by combining a therapeutically effective amount of a derivative of the first aspect with a pharmaceutically acceptable vehicle. The formulation of pharmaceutically active ingredients with various excipients is known in the art.

A "therapeutically effective amount" of a derivative of the first aspect is any amount which, when administered to a subject, is the amount of derivative that is needed to treat the disease, disorder or condition or produce the desired effect.

For example, the therapeutically effective amount of derivative used may be from about 0.001 mg to about 1000 mg, and preferably from about 0.01 mg to about 500 mg. It is preferred that the amount of derivative is an amount from about 0.1 mg to about 100 mg, and most preferably from about 0.5 mg to about 50 mg. As a guide, the dose of derivative used in the mice in Example 3 described herein was 0.5 mg/kg (administered subcutaneously).

A "pharmaceutically acceptable vehicle" as referred to herein, is any known compound or combination of known compounds that are known to those skilled in the art to be useful in formulating pharmaceutical compositions.

In one embodiment, the pharmaceutically acceptable vehicle may be a solid; optionally the composition may be in the form of a powder for resuspension. A solid pharmaceutically acceptable vehicle may include one or more substances which may also act as flavouring agents, lubricants, solubilisers, suspending agents, dyes, fillers, glidants, inert binders, preservatives or dyes. The vehicle may also be an encapsulating material. In powders, the vehicle is a finely divided solid that is in admixture with the finely divided derivatives according to the invention. The powders preferably contain up to 99% derivative. Suitable solid vehicles include, for example calcium phosphate, magnesium stearate, talc, sugars, lactose, dextrin, starch, gelatin, cellulose and ion exchange resins.

In another embodiment, the pharmaceutical vehicle may be a gel and the composition may be in the form of a cream or the like.

However, the pharmaceutical vehicle may be a liquid; optionally the pharmaceutical composition is in the form of a solution. Liquid vehicles are used in preparing solutions, suspensions, emulsions, syrups, elixirs and pressurised compositions. The derivative according to the invention may be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilisers or osmo-regulators. Suitable examples of liquid vehicles for parenteral administration include water (partially containing additives as above, for example, cellulose derivatives, preferably sodium carboxymethyl cellulose solution), alcohols (including monohydric alcohols and polyhydric alcohols, for example, glycols) and their derivatives, and oils (for example, fractionated coconut oil and arachis oil). For parenteral administration, the vehicle can also be an oily ester such as ethyl oleate and isopropyl myristate. Sterile liquid vehicles are useful in sterile liquid form compositions for parenteral administration. The liquid vehicle for pressurised compositions can be a halogenated hydrocarbon or other pharmaceutically acceptable propellant.

The process for preparing a pharmaceutical composition of the invention may thus comprise the usual steps that are standard in the art.

According to a fourth aspect of the invention, therefore, there is provided a derivative of the first aspect, or a pharmaceutical composition of the third aspect, for use in therapy. A method of treating a subject with a derivative of the invention, or a pharmaceutical composition comprising the same, is also provided. Any of the different derivatives of IL-22 described or envisaged herein are expressly included in these aspects of the invention.

Terms such as "treating" and "therapy", as used herein, expressly include the treatment, amelioration or prevention of a disease, disorder or condition.

The derivative of IL-22 or pharmaceutical composition comprising the same may be administered directly into a subject to be treated. The derivative or pharmaceutical composition may be administered by any means, including by inhalation, by injection, topically or ocularly. When administered by inhalation, it may be via the nose or the mouth. Preferably, the derivative or pharmaceutical composition is administered by injection, typically subcutaneously or intravenously. The derivatives therefore have a clear advantage over Fc fusions in their flexibility of administration (e.g. by injection, by inhalation, topical application or ocular delivery) because of their smaller size and higher potency. It will be appreciated that administration, into a subject to be treated, of a derivative of the invention will result in the increased circulation time compared to hIL-22, and that this will aide in treating a disease, disorder or condition. As above, 'treating' also includes ameliorating and preventing a disease, disorder or condition.

Liquid pharmaceutical compositions, which are sterile solutions or suspensions, can be utilised by, for example, intramuscular, intrathecal, epidural, intraperitoneal and particularly subcutaneous or intravenous injection. The derivative may be prepared as a sterile solid composition that may be dissolved or suspended at the time of administration using sterile water, saline or other appropriate sterile injectable medium.

Forms useful for inhalation include sterile solutions, emulsions and suspensions. Alternatively the derivatives may be administered in the form of a fine powder or aerosol via a Dischaler® or Turbohaler®. Nasal inhalations may suitably be in the form of a fine powder or aerosol nasal spray or modified Dischaler® or Turbohaler®.

Topical formulations include solutions, creams, foams, gels, lotions, ointments, pastes, tinctures and powders. They may be epicutaneous, i.e. applied directly to the skin, or applied to mucous membranes.

Formulations for ocular administration are typically solutions, suspensions and ointments for topical application, e.g. in the form of eye drops. Alternatively sterile solutions or suspensions can be utilised by intraocular injection. The derivative may be prepared as a sterile solid composition that may be dissolved or suspended at the time of administration using sterile water, saline or other appropriate sterile injectable medium. The formulation may be for subconjunctival, intravitreal, retrobulbar or intracameral injection.

A derivative or pharmaceutical composition of the invention may be administered to any subject in need thereof. A "subject", as used herein, may be a vertebrate, mammal or domestic animal. Hence, derivatives and compositions according to the invention may be used to treat any mammal, for example livestock (for example, a horse), pets, or may be used in other veterinary applications. Most preferably, the subject is a human being. The derivatives and compositions need not only be administered to those already showing signs of a disease, disorder or condition. Rather, they can be administered to apparently healthy subjects as a purely preventative measure against the possibility of such a disease, disorder or condition in future.

It will be appreciated that derivatives of IL-22 and compositions according to the invention may be used in a monotherapy (i.e. the sole use of that derivative or composition), for treating a disease, disorder or condition. Alternatively, derivatives and compositions according to the invention may be used as an adjunct to, or in combination with, known therapies for treating a disease, disorder or condition.

It will be appreciated that the amount of the derivative of IL-22 that is required is determined by its biological activity, half-life and bioavailability, which in turn depends on the mode of administration, the physiochemical properties of the derivative and composition, and whether it is being used as a monotherapy or in a combined therapy. The frequency of administration will also be influenced by the half-life of the derivative within the subject being treated.

Optimal dosages to be administered may be determined by those skilled in the art, and will vary with the particular derivative in use, the strength of the pharmaceutical composition, the mode of administration, and the advancement of the disease, disorder or condition. Additional factors depending on the particular subject being treated will result in a need to adjust dosages, including subject age, weight, gender, diet and time of administration.

Generally, a daily dose of between 0.001 µg/kg of body weight and 10 mg/kg of body weight of derivative of IL-22 according to the invention may be used for treating a disease, disorder or condition, depending upon which derivative or composition is used. More preferably, the daily dose is between 0.01 µg/kg of body weight and 1 mg/kg of body weight, more preferably between 0.1 µg/kg and 500 µg/kg body weight, and most preferably between approximately 0.1 µg/kg and 100 µg/kg body weight.

The derivative of IL-22 or composition may be administered before, during or after onset of the disease, disorder or condition. Daily doses may be given as a single administration (for example, a single daily injection). Alternatively, the derivative or composition may require administration twice or more times during a day. As an example, derivatives may be administered as two (or more depending upon the severity of the disease, disorder or condition being treated) daily doses of between 0.07 µg and 700 mg (i.e. assuming a body weight of 70 kg). A patient receiving treatment may take a first dose upon waking and then a second dose in the evening (if on a two-dose regime) or at 3- or 4-hourly intervals thereafter. Doses may alternatively be given once a week, every fortnight or once a month, or more frequently, for example, two or three times weekly. Known procedures, such as those conventionally employed by the pharmaceutical industry (for example, in vivo experimentation, clinical trials, etc.), may be used to form specific formulations of the derivatives and compositions according to the invention and precise therapeutic regimes (such as daily doses of the agents and the frequency of administration).

Many studies have demonstrated key effects of IL-22 in multiple epithelial injury models in especially lung, liver, intestine, kidney, skin, pancreas and thymus. Mechanistically, several pathways within e.g. anti-apoptosis, proliferation, innate immunity, anti-oxidative stress, anti-fibrosis, and stem cell/progenitor cell recruitment have been well documented to meditate IL-22 effects in studies by multiple investigators. Key mechanistic findings have been further confirmed in vitro using human cell lines or in human ex vivo models (e.g. primary human intestinal organoids). The strong role of IL-22 in preventing cell death, securing regeneration, and controlling inflammation in epithelial injury is therefore well established.

Many studies are performed by analysing genetic models (IL-22 knock-out or transgenic overexpression) subjected to injury. In these studies, the lack of IL-22 or overexpression of IL-22 will be there at the time of injury. In other studies, IL-22 is neutralised with antibodies at the time of injury and, in some cases, IL-22 is neutralised beyond the acute injury phase (e.g. sub-acutely or well into a regeneration phase). Other studies move closer to a treatment scenario by looking at effects of exogenously administered IL-22. Important to note, when looking holistically at the available literature, is that the different models, whether knock-out, overexpression, IL-22 neutralisation before or after injury or exogenous protein dosing, paint the same picture of IL-22 protecting the injured organs and driving regeneration. This indicates a broad application and a broad time window for IL-22 treatment potential, and also shows why a longer-acting IL-22 protein than hIL-22 is required.

Thus, according to a fifth aspect of the invention, there is provided a derivative of the first aspect, or a pharmaceutical composition of the third aspect, for use in a method of treating a metabolic, liver, pulmonary, gut, kidney or skin disease, disorder or condition. Any of the different derivatives of IL-22 described or envisaged herein are expressly included in this aspect of the invention.

The metabolic disease, disorder or condition may be obesity, diabetes type 1, diabetes type 2, hyperlipidemia, hyperglycemia or hyperinsulinemia.

The liver disease, disorder or condition may be NAFLD, NASH, cirrhosis, alcoholic hepatitis, acute liver failure, chronic liver failure, ACLF, acetaminophen induced liver toxicity, acute liver injury, sclerosing cholangitis, biliary cirrhosis or a pathological condition caused by surgery or transplantation.

The pulmonary disease, disorder or condition may be COPD, cystic fibrosis, bronchiectasis, idiopathic pulmonary fibrosis, acute respiratory distress syndrome, a chemical injury, a viral infection, a bacterial infection or a fungal infection.

The gut disease, disorder or condition may be IBD, ulcerative colitis, Crohn's disease, GvHD, a chemical injury, a viral infection or a bacterial infection.

The kidney disease, disorder or condition may be acute kidney disease or chronic kidney disease.

The skin disease, disorder or condition may be a wound, inflammatory disease or GvHD.

A method of treating a subject having a condition responsive to IL-22 treatment, such as one or more of the above diseases, disorders or conditions, with a derivative of IL-22, or a pharmaceutical composition comprising the same, is also provided.

The derivative of IL-22 has all of the features specified for the first aspect of the invention. The pharmaceutical composition has all of the features specified for the third aspect of the invention. The method of treating a subject having a condition responsive to IL-22 treatment, such as one or more of the above diseases, disorders or conditions, has all of the features specified for the fourth aspect of the invention.

There is no restriction on which derivative of IL-22 or composition as described herein should be administered to which patient. Rather, it is intended that any of the derivatives and compositions described herein can be administered to any patient as described herein.

All of the features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made to the Examples, which are not intended to limit the invention in any way.

EXAMPLES

The materials and methods employed in the studies described in the Examples were as follows, unless where otherwise indicated.

Derivatives

Table 4 provides an overview of the derivatives of IL-22 and comparators represented in the data sets.

The derivatives of IL-22 had various backbones, types of fatty acid and sites of covalent attachment and were thus representative of the diversity of the derivatives encompassed by the invention. The linker used in all cases was γGlu-OEG- OEG-C₂DA-Ac. In all cases the linker was attached to residue 1C, except for Derivatives 2 (-7C), 4 (-7C), 8 (6C) and 9 (33 C). Whilst Derivative 7 exemplifies covalent attachment at 1C, it lacks the G-P-G N-terminal peptide present in all of the other derivatives that have a fatty acid covalently attached at 1 C.

The comparators were hIL-22, hFc-hIL-22 (a recombinant fusion protein) and hIL-22 variants (i.e. hIL-22 having one or more backbone variations only).

TABLE 4

Overview of key derivatives and comparators represented in data sets

| ID | SEQ ID NO. (for IL-22 protein) | Backbone variation | Fatty acid or other protractor |
|---|---|---|---|
| hIL-22 | SEQ ID NO. 1 | None | None |
| hFc-hIL-22 | SEQ ID NO. 1 | None | Fc |
| Comparator 1 | SEQ ID NO. 22 | A1G | None |
| Comparator 2 | SEQ ID NO. 23 | A1G, N21D, N35D, N64D | None |
| Comparator 3 | SEQ ID NO. 24 | A1G, N35Q, N64Q | None |
| Comparator 4 | SEQ ID NO. 16 | G-P-G N-terminal peptide, A1C | None |
| Comparator 5 | SEQ ID NO. 18 | G-P-G N-terminal peptide, A1C, N35Q, N64Q | None |
| Derivative 1 | SEQ ID NO. 16 | G-P-G N-terminal peptide, A1C | C18 diacid |
| Derivative 2 | SEQ ID NO. 17 | G-P-G-S-G-S-G-S-C-G-S-G-S-G-S N-terminal peptide | C18 diacid |
| Derivative 3 | SEQ ID NO. 16 | G-P-G N-terminal peptide, A1C | C16 diacid |
| Derivative 4 | SEQ ID NO. 17 | G-P-G-S-G-S-G-S-C-G-S-G-S-G-S N-terminal peptide | C16 diacid |
| Derivative 6 | SEQ ID NO. 18 | G-P-G N-terminal peptide, A1C, N35Q, N64Q | C18 diacid |
| Derivative 7 | SEQ ID NO. 19 | A1C, N35Q, N64Q | C18 diacid |
| Derivative 8 | SEQ ID NO. 20 | G N-terminal peptide, H6C, N35Q, N64Q | C18 diacid |
| Derivative 9 | SEQ ID NO. 21 | A33C, N35Q, N64Q | C18 diacid |
| Derivative 10 | SEQ ID NO. 18 | G-P-G N-terminal peptide, A1C, N35Q, N64Q | C16 diacid |

A quality control analysis of the derivatives produced for the examples was carried out as follows.

Intact mass of proteins was determined in a post-deglycosylated sample by adding 20 μl of a 1 mg/ml sample to 2 μl N-Glycosidase F at room temperature for 48 h. The samples were then diluted to 0.2 mg/ml with PBS at pH 7.4, and analysed using a Synapt G2 connected to Waters Synapt G2, with Waters MassLynx 4.1. A 10-90 Column Acquity UPLC Protein BEH C4 1.7 μm 1×100 mm was used with the following mobile phase(s): A: 0.1% formic acid in water; and B: acetonitrile, 0.09% formic acid. Flow was at 120 μl/min, UV 214 nm (20 pts/s) and the gradient was as shown in Table 5.

TABLE 5

Gradient (% and min) employed for quality control of derivatives of IL-22

| Time (min) | Flow (ml/min) | % A |
|---|---|---|
| Initial | 0.12 | 90 |
| 1 | 0.12 | 90 |
| 17 | 0.12 | 10 |
| 18 | 0.12 | 0 |
| 19 | 0.12 | 0 |
| 20 | 0.12 | 90 |
| 25 | 0.12 | 90 |

The results are shown in Table 6.

TABLE 6

Mass and retention time observed for key derivatives of IL-22

| ID | Deglycosylated theoretical mass (Da) | Observed deglycosylated mass (Da) | Retention time (min) |
|---|---|---|---|
| Derivative 1 | 17807.6 | 17807.0 | 13.81 |
| Derivative 3 | 17779.6 | 17778.5 | 11.68 |
| Derivative 4 | 18658.4 | 18657.5 | 7.11 |
| Derivative 5 | 18225.0 | 18224.0 | 7.28 |
| Derivative 6 | 17832.7 | 17832.0 | 7.40 |

The quality control data thus verified that the intended derivatives had indeed been produced.

The following are exemplified protocols, merely intended to illustrate the claimed invention. The exact number of animals and time courses employed in the studies can be varied, as would be known to a person skilled in the art.

Example 1

Pharmacokinetic Study

Methods

Pharmacokinetic studies were carried out on selected derivatives in mice (n=27), rats (n=4-8) and minipigs (n=2-5). The derivatives of IL-22 were tested alongside hIL-22, hFc-hIL-22 and/or hIL-22 variants as comparators.

(i) Mice & Rats 30 8-week old C57Bl/6 male mice and five Sprague Dawley male rats were obtained from Taconic Biosciences. The mice were housed in groups of 10. Animals were acclimatised for one week prior to the experiments. Body weight was measured prior to dosing, which is important for pharmacokinetic calculations. The animals were awake throughout the experiment, with access to food and water.

All derivatives and comparators were prepared as 0.3 mg/ml solutions in PBS, pH 7.4, for use in mice and 0.5 mg/ml solutions for use in rats. A dose of 2.0 mg/kg was tested in mice. A dose of 1 mg/kg was tested in rats.

The derivatives and comparators were administered to the animals subcutaneously. Blood samples were taken at specific time points after dosing.

Sparse sampling was used in mice; thus, 27 mice were dosed with a derivative of IL-22 or comparator and blood samples were taken from three different mice at each of the following time points: 5 min, 15 min, 30 min, 45 min, 60 min, 75 min, 90 min, 105 min, 120 min, 150 min, 3 h, 4 h, 6 h, 8 h, 16 h, 24 h, 32 h and 48 h. Each mouse therefore had just two samples taken during the course of the study. After the last sample was taken, the mice were euthanised by cervical dislocation.

Five rats were dosed with a derivative of IL-22 or comparator and three blood samples were taken at each of the following time points: 5 min, 15 min, 30 min, 45 min, 60 min, 75 min, 90 min, 105 min, 120 min, 150 min, 3 h, 4 h, 6 h, 8 h and 24 h. Each rat had 17 samples taken during the course of the study. After the last sample was taken, the rats were euthanised by carbon dioxide.

Blood samples (100 μl) were taken from mice and rats by tongue blood and transferred to EDTA tubes (Microvette® VetMed 200 K3E, Sarstedt nr 09.1293.100). The blood was centrifuged for five minutes at 8000 G, 4° C. within 20 minutes of being drawn. The plasma samples (40-50 μl) were transferred to half micronic tubes.

(ii) Minipigs 9-month old female Gottingen minipigs having a body weight of approximately 15 kg were obtained from Ellegaard Gottingen Minipigs A/S. An acclimatisation period of approximately 18 days was allowed before surgery (insertion of catheters), during which time the minipigs were socialised and trained for subcutaneous dosing and blood sampling from the catheter. Three to five days before surgery the minipigs were single-housed. Six days before dosing all minipigs had two central venous catheters (Cook Medical, C-TPNS-6.5-90-REDO, silicon, size 6.5 french, 106 cm long type TPN) inserted, which allowed a recovery time after surgery of at least five days before study start (dosing).

All derivatives and comparators were prepared as solutions in PBS, pH 7.4. The doses used were 0.1 mg/kg (administered intravenously) or 0.2 mg/kg (administered subcutaneously).

Minipigs were lightly anaesthetized with Propofol during the dosing. Intravenous injections were administered to minipigs through the long central catheter. After administration, the catheter was flushed with 10 ml sterile saline. Subcutaneous injection was given in 5 mm depth using a 25 G needle. The needle was kept in the skin for 10 s after injection to avoid back flow.

Blood samples were taken from the minipigs at the following time points after intravenous dosing: 1.5 h, 2 h, 3 h, 4 h, 6 h, 8 h, 10 h, 12 h, 24 h, 28 h, 48 h, 72 h, 96 h, 144 h, 168 h, 192 h, 216 h, 240 h, 264 h, 312 h, 336 h, 360 h, 384 h, 408 h, 432 h and 480 h. Blood samples were taken at the following time points after subcutaneous dosing: 1.5 h, 2 h, 3 h, 4 h, 5 h, 6 h, 8 h, 10 h, 12 h, 14 h, 16 h, 18 h, 20 h, 22 h, 24 h, 26 h, 28 h, 46 h, 52 h, 72 h, 96 h, 144 h, 168 h, 192 h, 216 h, 240 h, 264 h, 312 h, 336 h, 360 h, 384 h, 408 h, 432 h and 480 h.

Blood samples (1 ml) were collected from minipigs in EDTA tubes (1.3 ml tube containing K3EDTA to yield 1.6 mg K3EDTA/ml blood (Sarstedt, Germany)). Samples were kept on wet ice for a maximum of 30 min until centrifugation (10 min, 4° C., 2000 G). 200 μl plasma was transferred into Micronic tubes for measurement of the derivatives of IL-22 or comparators and stored at −20° C. until analysis.

(iii) Sample Processing

Plasma levels of derivatives of IL-22 or comparators were measured using in-house developed luminescent oxygen channeling (LOCI®) assays as previously described (Poulsen et al. *J Biomol Screen*, 2007, 12(2):240-7). During the assays, a concentration-dependent bead-analyte-immune complex was created, resulting in light output, which was measured on a Perkin Elmer Envision reader. Coupling of antibodies to beads, biotinylation of antibodies and LOCI assay procedure were performed as previously described (Petersen et al., *J Pharmaceut Biomed*, 2010, 51(1):217-24). Calibrators and quality control (QC) samples were produced in the same matrix as the study samples. Assay precision (% CV) was assessed and shown to be lower than 20% for all the tested samples.

The assay used anti-human IL-22 monoclonal antibody (R&D Systems MAB7822)-conjugated acceptor beads together with biotinylated monoclonal antibody (R&D Systems BAM7821; raised against human IL-22) and generic streptavidin-coated donor beads. The lower limit of quantification (LLOQ) for human IL-22 in rat plasma was 4 pM. Each derivative or comparator was, however, measured against a calibrator row of the same derivative. The cross-reactivity of each derivative or comparator against hIL-22 was measured and used to adjust the assay sensitivity.

Plasma concentration-time profiles were measured for minipigs using a non-compartmental analysis (NCA) in Phoenix WinNonlin Professional 6.4 (Pharsight Inc). Calculations were performed using individual concentrations, weighting by 1/(Y*Y), and using linear log trapezoidal. Intravenous dosing was used because circulatory elimination half-life ($T_{1/2}$) was the primary screening parameter. Clearance and volume of distribution were secondary parameters of interest, hence the reason for frequent blood samples during day 1 of the study.

The sole parameter measured to assess pharmacokinetics in mice and rats was circulatory elimination half-life ($T_{1/2}$). In minipigs, the additional parameters measured were maximum (peak) plasma concentration following drug administration ($C_{max}$), time to reach $C_{max}$ ($T_{max}$), area under the plasma drug concentration-time curve (AUC; which reflects the actual body exposure to drug after administration of a dose of the drug) normalised for drug dose (AUC/D), mean residence time (MRT; i.e. the time that the drug spends in the body prior to elimination once absorption has been completed), mean absorption time (MAT) and systemic availability of the administered dose (i.e. bioavailability; F). MAT is calculated as MRT following subcutaneous administration ($MRT_{SC}$) minus MRT following intravenous administration ($MRT_{IV}$).

Results

Table 7 shows the results obtained in mice, Table 8 shows the results obtained in rats and Tables 9 and 10 show the results obtained in minipigs. ND=not determined. IV=intravenous administration. SC=subcutaneous administration.

TABLE 7

Pharmacokinetic data obtained in mice

| ID | Route of Administration | $T_{1/2}$ (h) |
| --- | --- | --- |
| hFC-hIL-22 | IV | ND |
|  | SC | 30.0 |
| Comparator 1 | IV | 0.4 |
|  | SC | 1.4 |
| Comparator 3 | IV | 0.4 |
|  | SC | 0.7 |
| Derivative 1 | IV | 6.0 |
|  | SC | 8.3 |
| Derivative 6 | IV | 6.6 |
|  | SC | 9.1 |

As shown in Table 7, hIL-22 variants having backbone variations only (Comparators 1 and 3) had a short circulatory half-life, regardless of the route of administration. Protraction with Fc fusion (hFc-hIL-22) considerably increased half-life. Covalent attachment of fatty acid (C18 diacid; Derivatives 1 and 6) resulted in an intermediary circulatory half-life in mice. The derivatives of IL-22 circulated for longer in mice when administered subcutaneously compared to intravenously.

TABLE 8

Pharmacokinetic data obtained in rats

| ID | Route of Administration | $T_{1/2}$ (h) |
|---|---|---|
| Comparator 1 | IV | 0.2 |
|  | SC | ND |
| Derivative 1 | IV | 11.1 |
|  | SC | 10.9 |
| Derivative 3 | IV | 4.3 |
|  | SC | 9.7 |
| Derivative 6 | IV | 10.8 |
|  | SC | 12.3 |

As shown in Table 8, the hIL-22 variant having a backbone variation only (Comparator 1) had a short circulatory half-life. Covalent attachment of fatty acid (Derivatives 1, 3 and 6) resulted in an increased circulatory half-life in rats, regardless of the fatty acid (C16 vs C18 diacid) employed and route of administration. The derivatives of IL-22 typically circulated for longer when administered subcutaneously compared to intravenously.

TABLE 9

Pharmacokinetic data obtained in minipigs

| ID | Administration route | $T_{1/2}$ (h) |
|---|---|---|
| hIL-22 | IV | 4.6 |
|  | SC | 6.6 |
| hFc-hIL-22 | IV | 65.4 |
|  | SC | 141.0 |
| Comparator 1 | IV | 3.9 |
|  | SC | 8.7 |
| Comparator 2 | IV | 3.5 |
|  | SC | 3.7 |
| Derivative 1 | IV | 53.9 |
|  | SC | ND |
| Derivative 6 | IV | 66.5 |
|  | SC | 106.0 |
| Derivative 10 | IV | ND |
|  | SC | 40.0 |

As shown in Table 9, the hIL-22 variants having backbone variations only (Comparators 1 and 2) had a short circulatory half-life, comparable with hIL-22. The comparator Fc fusion (hFc-hIL-22) and all of the derivatives of IL-22 (Derivatives 1, 6 and 10) had a significantly increased circulating half-life. The derivatives of IL-22 had a circulating half-life of over 50 hours in minipig when administered intravenously, which was on par with the comparator IL-22-Fc fusion.

TABLE 10

Pharmacokinetic data obtained in minipigs

| ID | Administration route | Cmax (nmol/l) | Tmax (h) | AUC/D (h*kg*pmol/ 1/pmol) | MRT (h) | MAT (h) | F (%) |
|---|---|---|---|---|---|---|---|
| hFc-hIL-22 | IV | 56.0 | 0.05 | 407 | 91.7 | ND | ND |
|  | SC | 14.8 | 5.00 | 365 | 192.0 | 100 | 89.7 |
| Derivative 6 | IV | 98.9 | 0.05 | 551 | 85.6 | ND | ND |
|  | SC | 37.6 | 8.00 | 399 | 146 | 60.3 | 72.4 |

As shown in Table 10, a faster MAT was demonstrated for the derivative of IL-22 (Derivative 6) compared to the comparator Fc fusion (hFc-IL-22). MAT is a more precise measure of drug uptake than simply comparing $T_{max}$, as it also takes into consideration differences in $C_{max}$ ($T_{max}$ is influenced by both dose and $C_{max}$). Minipigs were used for this study, rather than mice or rats, because of their similarity to humans.

Conclusion

The known fatty acid alkylated GLP-1 derivative, semaglutide, has a half-life of 46 hours in minipig (Lau et al., *J Med Chem*, 2015, 58(18):7370-80) and a half-life of 160 hours in man, corresponding to a once-weekly dosing profile with a peak to trough ratio of 2. The half-life of the Fc-fusion GLP-1 derivative, dulaglutide, is similar.

The half-life demonstrated by the derivatives of IL-22 in minipig, of at least 40 hours when administered subcutaneously and over 50 hours when administered intravenously, is therefore assumed to correspond to a once-weekly dosing profile in man with a peak to trough ratio of 2.

The data hence show that the derivatives of the invention enhanced circulating half-lives of IL-22 and demonstrated optimised pharmacokinetic and pharmacodynamic properties, so offering a new and improved treatment for a diverse range of indications, including metabolic, liver, pulmonary, gut, kidney, eye, thymus, pancreas, and skin diseases, disorders and conditions.

Example 2

In Vitro Potency Study

Methods

Two in vitro assays were employed to study potency.

The first was a reporter gene assay in BHK cells, which had been triple transfected with IL-22Ra, IL-10Rb and a luciferase with STAT3-induced promoter. This is a highly sensitive, high-throughput assay, which measured IL-22 receptor-mediated STAT3 activation.

A stable reporter BHK cell line was generated using the following plasmids: (i) hIL-10Rb in pcDNA3, 1 hygro(+), (ii) IL22R in pcDNA3,1(Zeocin) and (iii) 2×KZdel2 in pGL4.20. The cell line hence expressed the human IL-10Rb, human IL-22Ra and luciferase reporter under control of a pSTAT3 driven promoter.

On Day 0 of the assay protocol, the cells were seeded in basal media (for 500 ml: DMEM+Glutamax (Gibco, cat. no.: 31966-021), 10% (w/v) fetal calf serum (FCS; contains albumin) (50 ml) and 1% (w/v) penicillin-streptomycin (P/S) (5 ml)) at 15,000-20,000 cells/well in a 96-well plate (Corning #3842, black, clear bottom). On Day 1, the media was removed by inverting the plate. Fresh basal media was added, at 50 µl per well, and the cells were incubated for 60 minutes.

The derivatives of IL-22 were tested alongside hIL-22 and hIL-22 variants having backbone variations only as comparators. The 'n' number of animals used to test each derivative or comparator ranged from 1-36.

Thus, 50 µl of a diluted derivative or comparator (diluted in basal media) was added to each well and the plate left for four hours. The derivatives and comparators were therefore 2× diluted, as they were diluted into the 50 µl media already in the wells. The stimulation was ended after four hours by adding 100 µl Steadylite plus reagent (Perkin Elmer cat no. 6066759). The plate was sealed with TopSeal A, shaken at 450 rpm for 15 minutes, then read using Mithras or a similar system no later than after 12 hours.

Data analysis was performed using Graphpad Prism. The half maximal effective concentration ($EC_{50}$) of each derivative or comparator was assessed as a measure of its potency. $EC_{50}$ was determined using Log(compound) vs response-variable slope (4p). Hill slope was constrained to 1 as standard.

The second in vitro potency assay measured pSTAT3 in HepG2 cells—a human liver-derived cell line endogenously expressing IL-22Ra and IL-10Rb.

On Day 1, HepG2 Cells were plated at 25,000-30,000 cells/well in a 96-well plate (Biocoat #35-4407 Becton Dickinson). The cell media used for plating and passaging was DMEM(1×)+25 mM (4.5 g/l) glucose, -pyruvate (Gibco, cat. no. 61965-026)+10% (w/v) FCS+1% (w/v) P/S. On Day 2, the cells were ready for assay. The cells were starved with 0.1% (w/v) FCS (i.e. a very low albumin concentration) in DMEM (Gibco, cat. no. 61965-026)—50 µl was added to each well and left for 60 minutes.

Tests were performed in seven concentrations of each derivative or comparator as standard (0.001, 0.01, 0.1, 1, 10, 100, 1000 nM) using technical duplicates. Thus, 50 µl of a diluted derivative or comparator (diluted in 0.1% (w/v) FCS in DMEM) was added to each well and the plate left for 15 minutes. The derivatives and comparators were therefore 2× diluted, as they were diluted into the 50 µl media already in the wells. To lyse the cells, media was removed from the cells and 50 µl of freshly prepared 1×lysis buffer (SureFire lysis buffer from kit) was added to each well. The plate was agitated at 350 rpm for 10 minutes at room temperature.

The AlphaScreen® SureFire® STAT3 (p-Tyr705) assay protocol (Perkin Elmer cat. no. TGRS3S (500-10K-50K)) was followed to measure IL-22 induced phosphorylation of STAT3. In this regard, 4 µl of lysate was transferred to a 384-well proxiplate for assay (adding 4 µl of positive and negative control). Immediately prior to use, Acceptor mix was prepared (by diluting Activation buffer 5-fold in reaction buffer and diluting Acceptor beads 50-fold in the diluted buffer). 5 µl of Acceptor mix was added to each well, the plate sealed with Topseal A adhesive film and incubated for two hours at room temperature. Immediately prior to use, Donor mix was prepared (by diluting Donor beads 20-fold in Dilution buffer). 2 µl of donor mix was added to the wells under subdued light. The plate was again sealed with Topseal A adhesive film and incubated for two hours at room temperature. The plate was read on an Alpha Technology-compatible plate reader.

Data analysis was performed using Graphpad Prism. First, a non-linear regression was conducted using Log(compound) vs. response-variable slope (4p) analysis in Prism. Hill slope was constrained to 1. The Y=top from the control compound (either His tagged hIL-22 or hIL-22) was then used for a normalisation in Prism. 0% was set to the smallest value in each data set and 100% to Y=top from the above non-linear regression (for the control). A non-linear regression was repeated as above and % activity/wt and $EC_{50}$ of the tested derivatives read in the results under top and $EC_{50}$ respectively.

Results

Table 11 shows the $EC_{50}$ of key derivatives and comparators measured in the BHK cell reporter gene assay for IL-22 receptor mediated STAT3 activation.

TABLE 11

$EC_{50}$ values for key derivatives and comparators in BHK cell assay

| ID | $EC_{50}$ (nM) |
|---|---|
| hIL-22 | 0.07 |
| Comparator 1 | 0.06 |
| Comparator 5 | 0.19 |
| Comparator 14 | 0.09 |
| Derivative 1 | 0.48 |
| Derivative 3 | 0.30 |
| Derivative 4 | 0.18 |
| Derivative 6 | 0.61 |
| Derivative 7 | 0.09 |
| Derivative 8 | 1.24 |
| Derivative 9 | 0.28 |
| Derivative 10 | 0.37 |

As the BHK cell assay contained high amounts of albumin, the measured $EC_{50}$ incorporated the effect of albumin binding when testing the derivatives.

Comparator 4, an IL-22 variant having backbone variations only, was shown to be equipotent to hIL-22. Derivative 3, having the same backbone as Comparator 4, but covalently attached to a medium affinity albumin binder (C16 diacid), exhibited a four-fold reduction in potency compared to hIL-22. Derivative 1, again having the same backbone, but covalently attached to a high affinity albumin binder (C18 diacid), exhibited only a seven-fold reduction in potency compared to hIL-22.

A scan of alkylation positions and backbone variations has been performed with off-set in a 35Q, 64Q background (i.e. two of the three IL-22 glycosylation sites mutated) by comparing the results for Derivatives 6-9. The covalent attachment sites in these derivatives had been chosen based on an analysis of the IL-22 structure identifying positions that are expected to be surface exposed and not involved in receptor binding. The results obtained with these derivatives demonstrate that Cys substitution and fatty acid covalent attachment may be tolerated in several (select) positions, which was surprising to the inventors.

Table 12 shows the $EC_{50}$ of key derivatives and comparators measured in the HepG2 cell assay for pSTAT3.

TABLE 12

$EC_{50}$ values for key derivatives and comparators in HepG2 cell assays

| ID | $EC_{50}$ (nM) |
|---|---|
| hIL-22 | 3.88 |
| Comparator 1 | 4.73 |
| Comparator 4 | 12.11 |
| Derivative 1 | 10.13 |
| Derivative 2 | 6.98 |
| Derivative 6 | 14.86 |

In the HepG2 cell assay with endogenous expression level of receptors, little signal amplification and no albumin, Derivative 1 had a 2.5-fold reduced potency compared to hIL-22 (similar to Comparator 4, an hIL-22 variant having the same backbone as Derivative 1, but no fatty acid).

Table 13 collates the results from both the BHK and HepG2 cell assays to assess fatty acid covalent attachment in N-terminal extension and mutation of glycosylation sites. ND=not determined.

TABLE 13

EC$_{50}$ values for key derivatives and
hIL-22 in BHK and HepG2 cell assays

| ID | BHK cells EC$_{50}$ (nM) | HepG2 cells EC$_{50}$ (nM) |
|---|---|---|
| hIL-22 | 0.07 | 3.88 |
| Derivative 1 | 0.48 | 10.13 |
| Derivative 2 | ND | 6.98 |
| Derivative 4 | 0.18 | ND |
| Derivative 6 | 0.61 | 14.86 |

Derivative 6 differs from Derivative 1 by the additional N35Q and N64Q substitutions (two out of three glycosylation sites mutated), yet they are equipotent (with a tendency to slightly lower potency for Derivative 6).

Whilst Derivatives 2 and 4 have a 15-mer N-terminal extension, with the Cys residue for fatty acid attachment in the extension (−7C), this is surprisingly shown to be well-tolerated.

Conclusion

The potency reduction observed with fatty acid covalent attachment in the tested derivatives of the invention was primarily driven by albumin binding, with backbone substitutions having little contribution. This was demonstrated by the surprising equipotency of Comparator 4 and hIL-22. In comparison, and as aforementioned, Genentech reports a 34-fold reduction in in vitro potency for its Fc fusion of IL-22.

In the HepG2 cell assay with very low albumin levels, Derivative 1 (the derivative of IL-22 that showed a sevenfold potency reduction in the BHK assay (with albumin binding)) showed only a 2.5-fold reduction in potency compared to hIL-22.

The equipotency of Derivatives 1 and 6 (Table 13) showed that the 35Q and 64Q mutations are surprisingly tolerated without effect on potency.

Thus, derivatives of IL-22 maintain high potency in the presence of albumin and are near equipotent with hIL-22 in the absence of albumin. Cys substitution and fatty acid covalent attachment are tolerated in several positions.

The data hence show that the derivatives of the invention demonstrate good bioavailability and potency, so offering a new and improved treatment for a diverse range of indications, including metabolic, liver, pulmonary, gut, kidney and skin diseases, disorders and conditions.

Example 3

In Vivo Efficacy Study in Diabetes

This study was designed to investigate the effect of once-daily dosing with a derivative of the invention for 8-16 days in a diabetes mouse model. The study was done in treatment (not preventive) mode, meaning that diabetes pathology was developed before dosing was initiated. As the mouse model has a fatty liver (leptin receptor knockout), it also functions as a metabolic model of liver disease.

Methods 7-8 week old male C57BKS db/db mice were obtained from Charles River Laboratories (Day −10) and acclimatised for at least one week prior to the start of experiments. One week after arrival (Day −3), the mice were randomised and housed in groups of 10 (or singly for the food intake study). On Day −3, and on each of Days 1-16 of the study, blood glucose and food intake were measured.

A derivative of IL-22 (Derivative 1) was tested alongside an Fc fusion of IL-22 (hFc-hIL-22) as a comparator and vehicle only as a negative control. Each agent was administered subcutaneously in a once-daily dose of 0.1, 0.25, 0.5 or 1.0 mg/kg on each of Days 1-16 days in the diabetic db/db mice (n=6-10 in each group). Food intake was reduced following derivative/comparator/control dosing.

Blood glucose was measured daily over the study duration. Eye blood samples were taken at termination in anaesthetised mice. 500 µl blood was collected into EDTA tubes. The samples were kept on ice and centrifuged for five minutes at 6000 G at 4° C. within 20 minutes. Plasma was separated into 0.75 ml micronic tubes and immediately frozen for later measurement of component concentrations.

As well as measuring derivative or comparator concentration, the plasma levels of target engagement biomarkers (the liver-derived acute phase proteins, haptoglobin and Serum Amyloid P component (SAP), and the gut-derived Peptide YY (PYY)) were measured at study end. Haptoglobin was measured on a COBAS instrument (Roche Diagnostics) with commercial kit according to the manufacturer's instructions. PYY was measured with a commercial ELISA assay (ALPCO) recognising mouse and rat PYY according to manufacturer's instructions. SAP was measured with a commercial ELISA assay (R&D Systems) recognising mouse Pentraxin 2/SAP according to manufacturer's instructions.

Results

Figure 5:
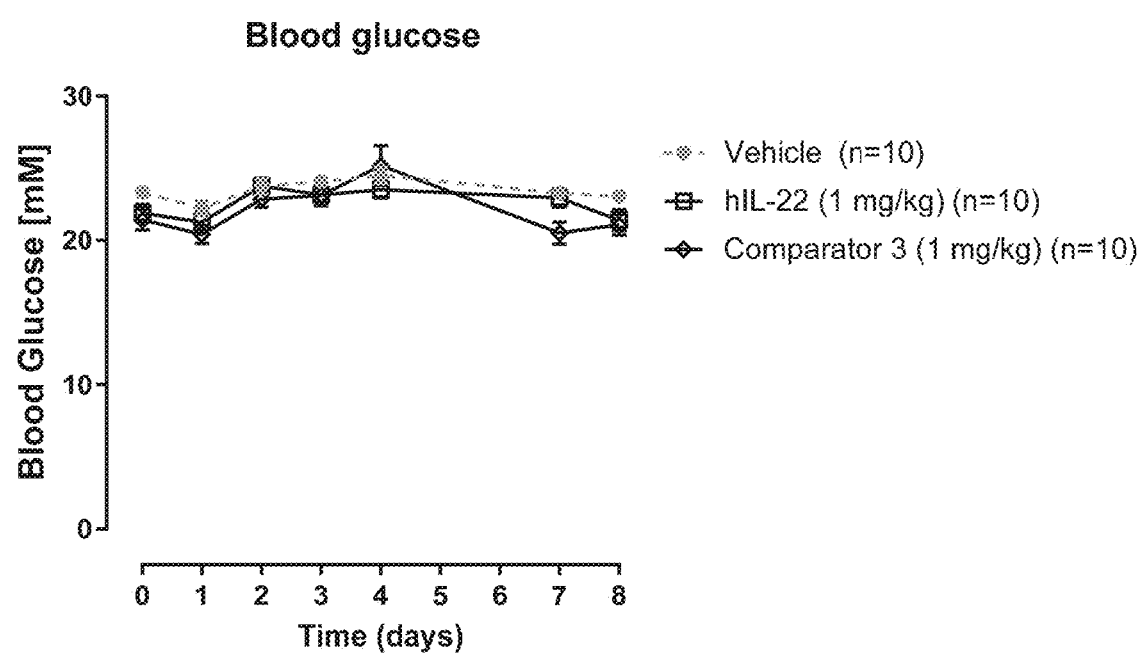
FIG. 5 illustrates the effect of daily dosing of hIL-22 and a comparative IL-22 variant having backbone variations only (identified herein as Comparator 3) on blood glucose in an 8-day study in a diabetes mouse model (mean±SEM).
Figure 6A:
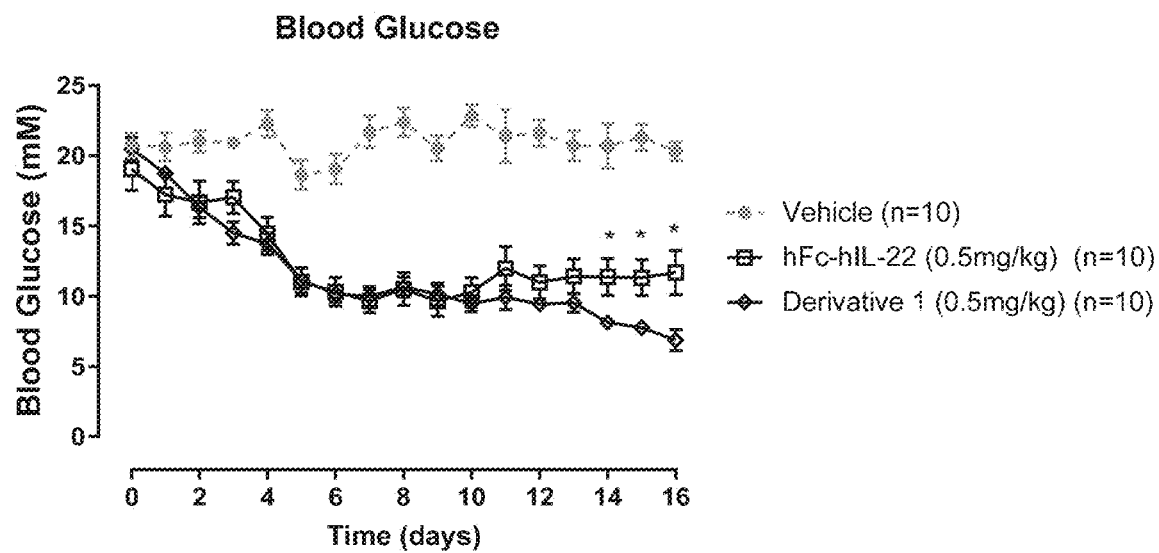
FIGS. 6A-6B illustrate the effect of daily dosing of a derivative of the invention (herein identified as Derivative 1) compared to an IL-22-Fc fusion (specifically a human Fc N-terminally fused to hIL-22; hereinafter "hFc-hIL-22") on (FIG. 6A) blood glucose, and (FIG. 6B) food intake, in a 16-day study in a diabetes mouse model (mean±SEM; * means $p<0.05$ using an unpaired t-test).

Blood glucose levels over the duration study are shown in FIGS. 5 and 6A.

As can be seen from FIG. 5, hIL-22 and an hIL-22 variant having backbone variations only (Comparator 3) failed to reduce blood glucose over the course of the study compared to the vehicle control.

Figure 6B:
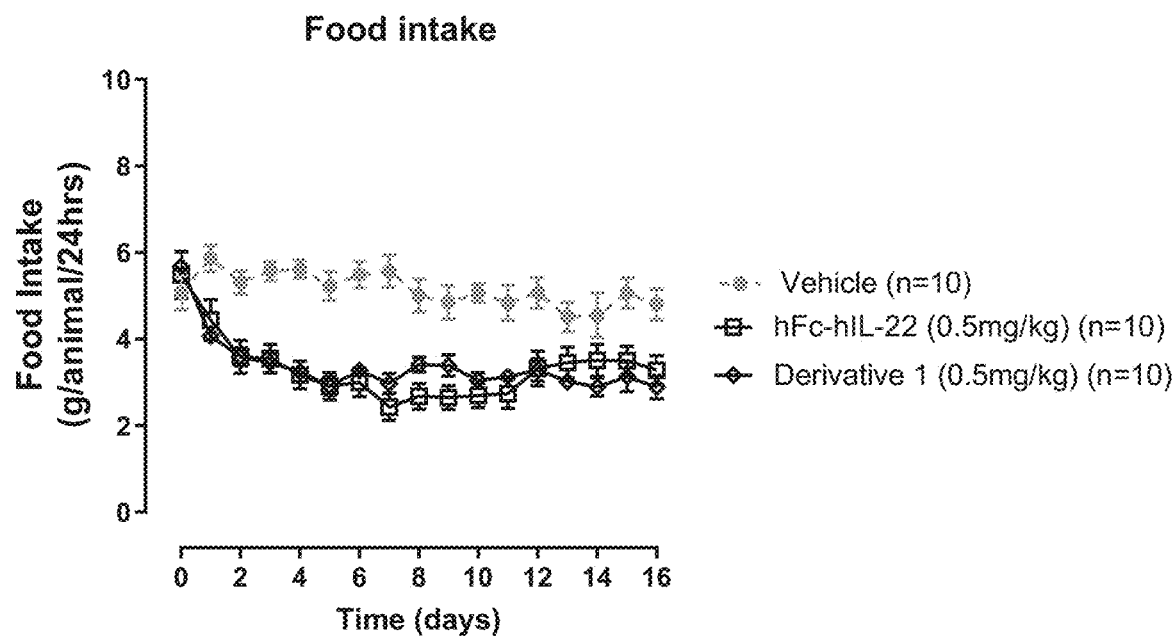

As can be seen from FIG. 6A, Derivative 1 and hFc-hIL-22 both reduced blood glucose in a comparable manner toward normal levels with a slightly higher efficacy of Derivative 1 in the last days of the study, despite higher target engagement of hFc-hIL-22 reflecting a higher steady state exposure level in the specific study. A reduction in food intake was observed in the treated animals compared to the vehicle control (see FIG. 6B). The tested derivative thus normalised blood glucose in the db/db model in a similar manner to hFc-hIL-22; as above, no such effect was observed with hIL-22 or Comparator 3.

Figure 7A:
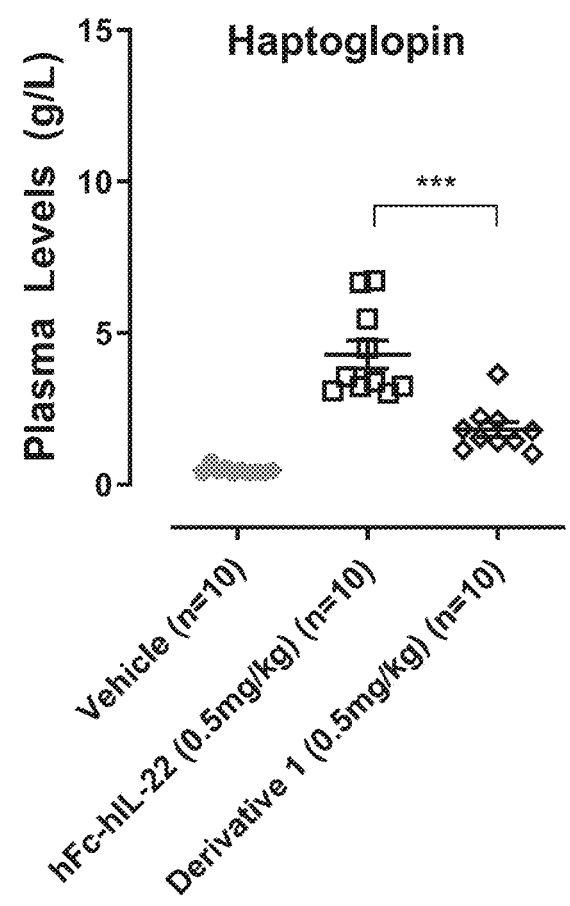
FIGS. 7A-7C illustrate the effect of daily dosing of Derivative 1 and hFc-hIL-22 on three different target engagement biomarkers, in a 16-day study in a diabetes mouse model (mean±SEM; *** means (A) $p<0.0002$, (B) $p<0.0003$ or (C) $p<0.0026$ using an unpaired t-test).
Figure 7B:
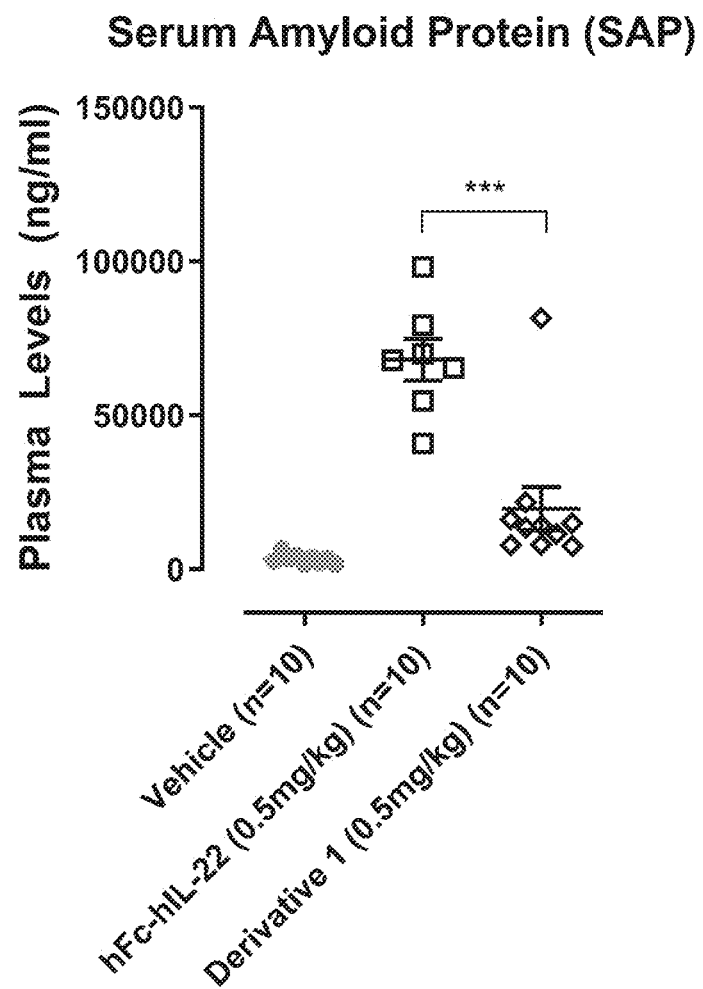
Figure 7C:
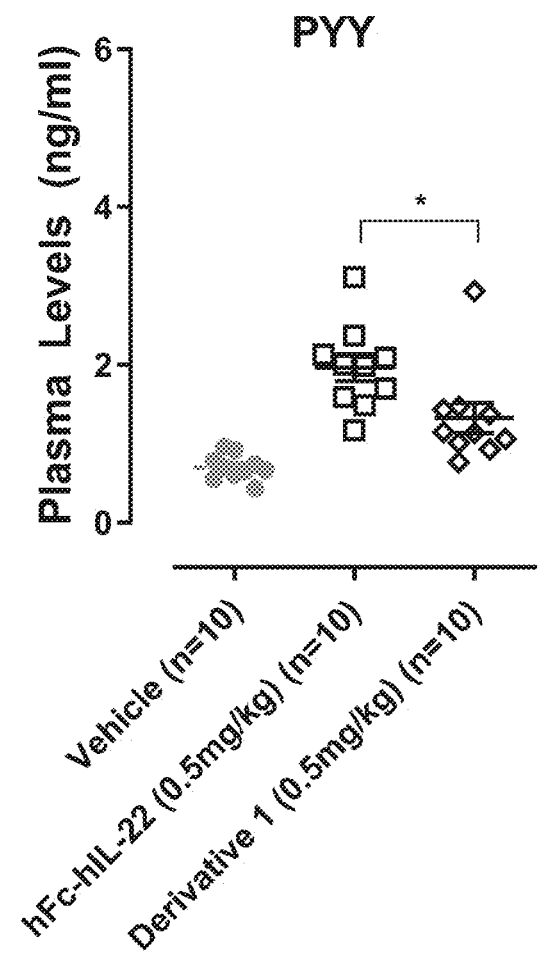

The level of the target engagement biomarkers, haptoglobin, SAP and PYY, as measured at the study end, are shown in FIG. 7A-C, respectively. As can be seen in the graphs, all three target engagement biomarkers were upregulated by the tested derivative and hFc-hIL-22, moreso by hFc-hIL-22 than Derivative 1.

Figure 8:
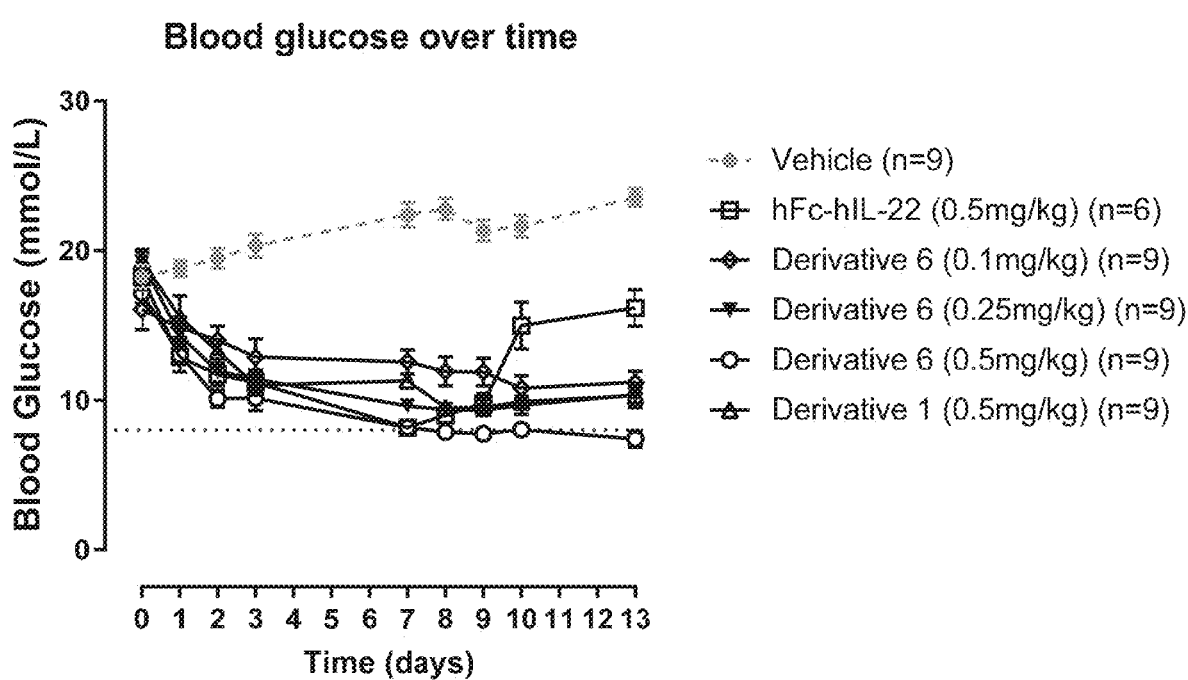
FIG. 8 illustrates a dose-response curve for daily dosing of a derivative of the invention (herein identified as Derivative 6) (three different doses) compared to Derivative 1 and hFc-hIL-22 on blood glucose in a 13-day study in a diabetes mouse model (mean±SEM).

FIG. 8 shows dose-response data for Derivative 6 (another derivative of the invention, it being the same as Derivative 1 but for additional substitutions in two glycosylation sites). All three doses tested (0.1, 0.25 and 0.5 m/kg) were effective at reducing blood glucose over time, and progressively moreso with increasing concentration.

Conclusion

Both of the tested derivatives and hFc-hIL-22 normalised blood glucose in the db/db model, thereby demonstrating an in vivo therapeutic effect. Importantly, no such effect was seen with dosing of hIL-22, demonstrating that the chronic exposure obtained with the long-acting derivatives and Fc fusion is necessary for the therapeutic effect. Whilst the mode of action for the anti-diabetic effect is not yet fully elucidated, it is believed that IL-22 effects on the liver (hepatic gluconeogenesis and lipogenesis) are a major contributor.

Food intake was also shown to be reduced by treatment with a derivative of the invention, thus demonstrating efficacy as an obesity treatment.

Target engagement biomarkers were also observed to be upregulated by the derivatives and hFc-hIL-22. The particular biomarkers measured in the db/db mice are known to translate to man.

It is important to note that the circulating half-life ($T_{1/2}$) of subcutaneously administered hFc-hIL-22 is higher than for Derivative 1, specifically in mice ($T_{1/2}$ of 20 and 8 hours, respectively; see Table 7). Therefore, the exposure of hFc-hIL-22 is higher at steady state.

This is further corroborated by the observation that the target engagement biomarkers (haptoglobin, SAP and PYY) were higher in the hFc-hIL-22 group than the Derivative 1 group (FIG. 7) demonstrating higher target engagement per se in the shown experiment. Thus, despite higher exposure and target engagement, the efficacy of the Fc fusion (hFc-hIL-22) was inferior, compared to the derivative of the invention (Derivative 1), in the last three days of a 16-day dosing study.

The data hence show that the derivatives of the invention demonstrate good therapeutic efficacy in a mouse model of diabetes and liver disease. As the particular biomarkers measured in the db/db mice are known to translate to man, it is reasonable to predict that such therapeutic efficacy translates too.

Example 4

In Vivo Efficacy Study in Liver Injury (i)

This study was designed to investigate the effect of dosing with derivatives of the invention in a liver injury mouse model. The study was done in preventive mode, meaning that liver injury was only induced after dosing had been initiated.

Methods 10 week-old C57Bl/6Rj mice were obtained and acclimatised for one week before study start. Liver injury was induced with a single intraperitoneal dose (300 mg/kg, 20 ml/kg) of APAP. Test derivatives of IL-22 (Derivatives 1 and 6) were dosed at 1.5 mg/kg subcutaneously two hours prior to APAP dosing, alongside vehicle controls (n=5-10). The study was terminated 24 hours after APAP dosing. A terminal bleed was secured for measurement of plasma alanine transaminase (ALT) and aspartate transaminase (AST).

Blood samples were collected in heparinised tubes and plasma was separated and stored at −80° C. until analysis. ALT and AST were measured using commercial kits (Roche Diagnostics) on the COBAS c501 autoanalyser according to the manufacturer's instructions.

Livers were subjected to formalin fixation and paraffin embedding for histological analysis. Proliferation was measured via ki67 immunohistochemistry (IHC) staining. IHC-positive staining was quantified by image analysis using VIS software (Visiopharm, Denmark).

Apoptosis was measured in a terminal deoxynucleotidyl transferase dUTP nick end labeling (TUNEL) assay. In brief, slides with paraffin-embedded sections were de-paraffinated in xylene and rehydrated in series of graded ethanol. The slides were pretreated with proteinase K and endogenous peroxidase activity was blocked with hydrogen peroxide. The TUNEL mixture (In Situ Cell Death Detection Kit, POD, Roche) was added to the slides, followed by amplification with horseradish peroxidase (HRP) and visualization by diaminobenzidine (DAB) (Chromogen). Finally, the slides were counterstained in hematoxylin and cover-slipped.

Results

Figure 9A:
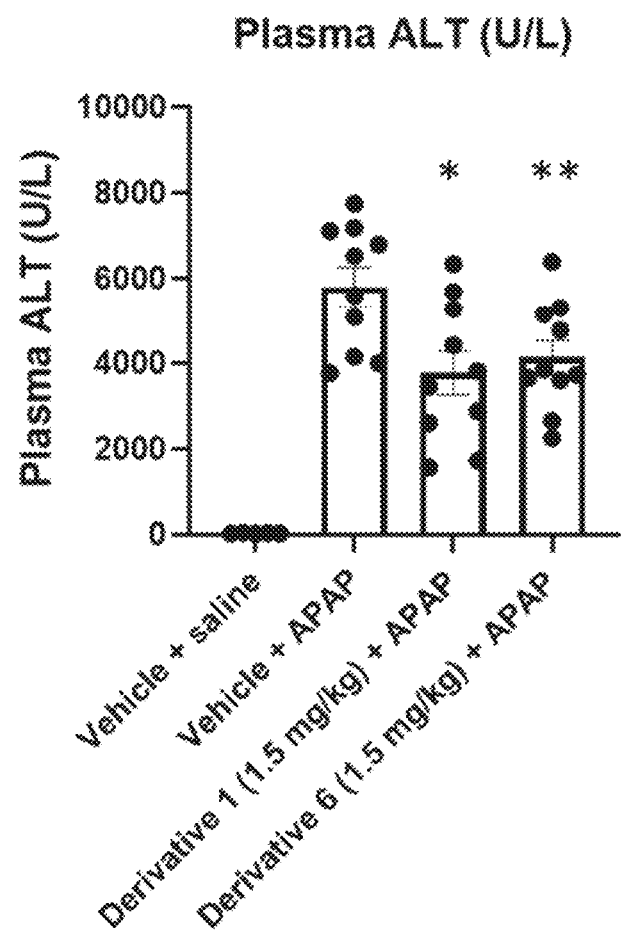
FIGS. 9A-9B illustrate the effect of Derivatives 1 and 6 in preventing liver injury in an acetaminophen (APAP)-induced liver injury mouse model, as evidenced by plasma levels of two different liver enzymes. Using Dunnett's test one-factor linear model, * means $p<0.05$ and ** means $p<0.01$ compared to vehicle +APAP.
Figure 9B:
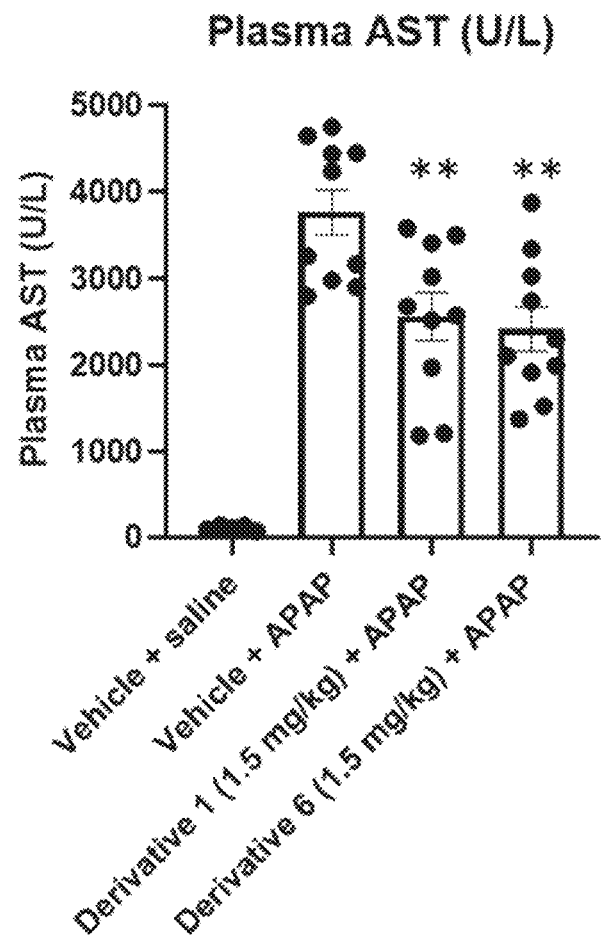

Plasma levels of ALT and AST at the termination of the study are shown in FIGS. 9A and 9B, respectively. The amount of ALT and AST was shown to be significantly reduced in mice treated with Derivative 1 or 6 prior to liver injury compared to the vehicle/APAP control.

Figure 10A:
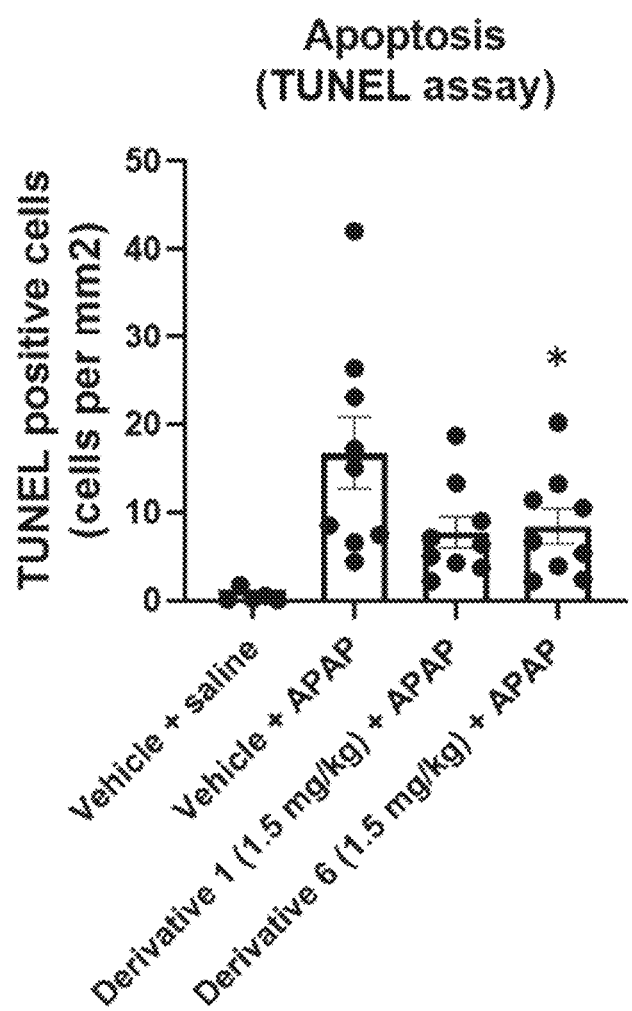
FIGS. 10A-10B illustrate the effect of Derivatives 1 and 6, (FIG. 10A) in preventing apoptosis and (FIG. 10B) on cellular proliferation, in an APAP-induced liver injury mouse model. NS means non-significant.
Figure 10B:
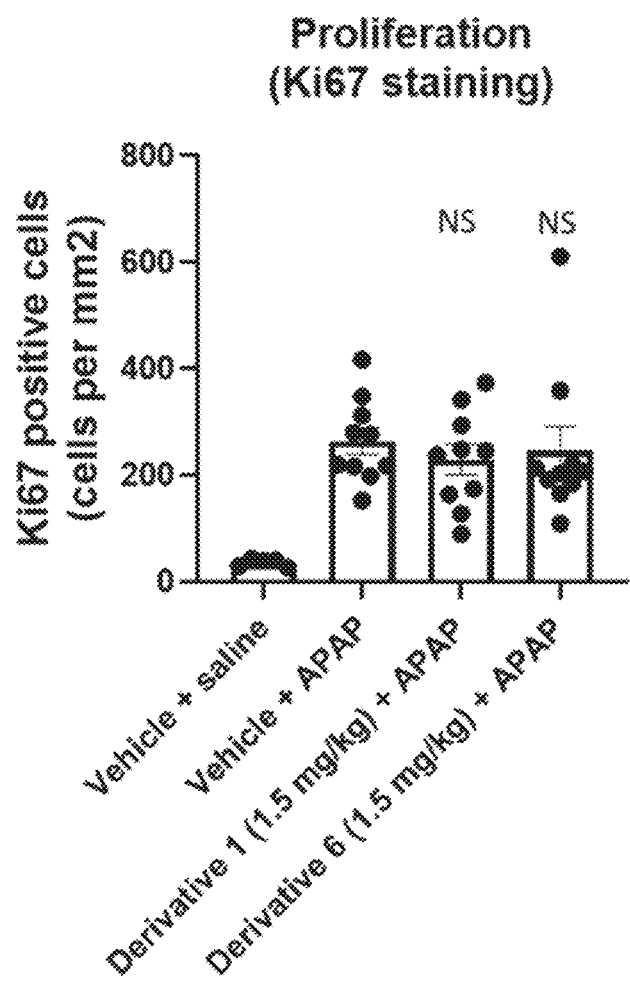

The number of TUNEL- and ki67-positive cells at the termination of the study are shown in FIGS. 10A and 10B, respectively. The amount of TUNEL-positive cells was (significantly) reduced in mice treated with Derivative 1 or 6 prior to liver injury compared to the vehicle/APAP control. The amount of ki67-positive cells was comparable across the APAP-treated groups.

Conclusion

ALT and AST are liver enzymes used as indicators of liver damage. Derivatives 1 and 6 were hence shown to protect the liver against injury induced by APAP.

The results of the TUNEL assay showed that Derivatives 1 and 6 protected against apoptosis caused by liver injury compared to the vehicle/APAP control. Cellular proliferation, however, was unaffected by these derivatives of IL-22. As proliferation is upregulated physiologically as a response to injury (as seen in control), the results demonstrate the proliferative action of Derivatives 1 and 6 as reduced injury is not followed by reduced proliferation (the ratio of proliferation over injury is increased).

The data hence show that the derivatives of the invention demonstrate good efficacy in protecting against liver injury in a mouse model. The particular biomarkers measured in the mice are known to translate to man, hence it is reasonable to predict that the observed protection would translate too.

Example 5

In Vivo Efficacy Study in Lung Injury

This study was designed to investigate the effect of dosing with a derivative of the invention in a lung injury rat model. The study was done in both preventive and treatment mode, meaning that dosing was initiated before the lung injury was induced and continued thereafter.

Methods

To induce lung injury, 100 μl of bleomycin was administered to the lungs of male Sprague Dawley rats by oropharyngeal aspiration as a single dose on Day 1 (Groups 2 to 6). Saline was administered as a negative control (Group 1).

Animals in Groups 3, 4 and 5 were dosed (by subcutaneous injection) once daily with Derivative 6 at 0.5, 1.5 or 4.5 mg/kg respectively, from Day −1 to Day 3. Animals in Group 6 were dosed (by oral gavage) once daily with prednisolone at 10 mg/kg from Day −1 to Day 3.

In order to measure soluble collagen in bronchoalveolar lavage fluid (BALF) from the rats, lungs were lavaged (3×4 ml) with sterile PBS (without calcium and magnesium) including added protease inhibitor cocktail, and the lavages per animal placed into one tube. Soluble collagen was measured in BALF supernatant using Soluble Collagen Assay Sircol S1000 (Biocolor) (Charles River Laboratories).

All animals were submitted for necropsy on Day 4 (terminal euthanasia). The right lung was collected for histopathological examination from all animals and inflation-fixed with 10% neutral buffered formalin (NBF) before being immersion-fixed in NBF. Three parallel longitudinal sections were trimmed from the right caudal lung lobe and mounted in cassette 01. The right cranial, middle and accessory lung lobes were also sectioned longitudinally and mounted in cassette 02.

Two slides were made from each cassette; one slide was stained with haematoxylin and eosin (H&E), while the other was stained with haematoxylin and picrosirius red (H&PSR).

Each slide was then assigned a random number using a random number generator. The identification key was recorded in a Microsoft Excel spreadsheet and a copy was provided to the study pathologist following slide evaluation. The six sections per lung were therefore read blind.

A veterinary pathologist then scored each section on each H&E-stained slide for severity of inflammation (where 0=absent, 1=minimal, 2=mild, 3=moderate and 4=severe). The mean and median score per Group was calculated. The pathologist also scored each section on each H&PSR-stained slide for severity of fibrosis (using a modified Ashcroft score from 0=low to 8=high). The mean and median score per Group was calculated and subjected to non-parametric ANOVA, Kruskal-Wallis post-test analysis.

Results

A summary of the microscopic findings is shown in Table 14, which reveals the mean and median scores for inflammation and fibrosis for each Group.

Figure 11A:
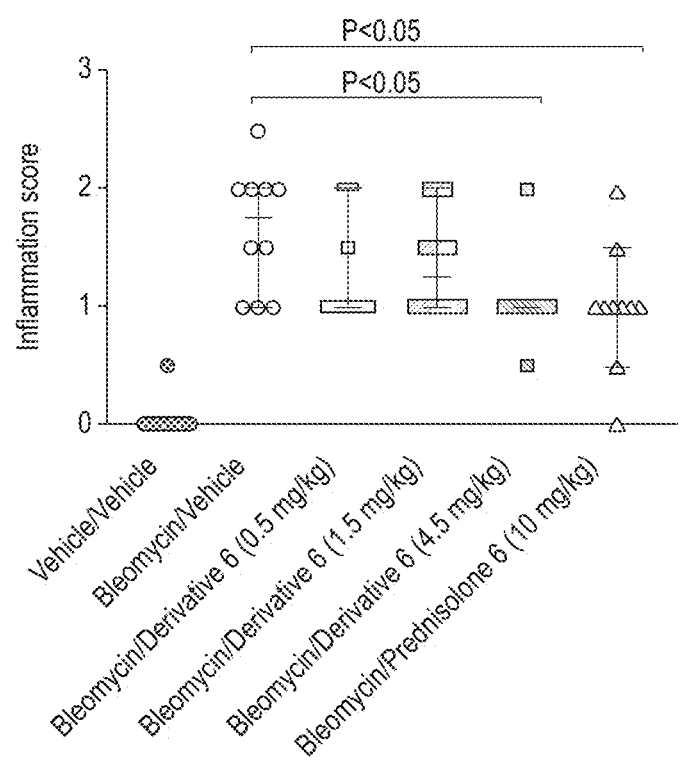
FIGS. 11A-11C illustrate the effect of Derivative 6 in preventing and/or reducing (FIG. 11A) lung inflammation, and (FIG. 11B) and (FIG. 11C) lung fibrosis, in a bleomycin-induced lung injury rat model, compared to prednisolone.
Figure 11B:
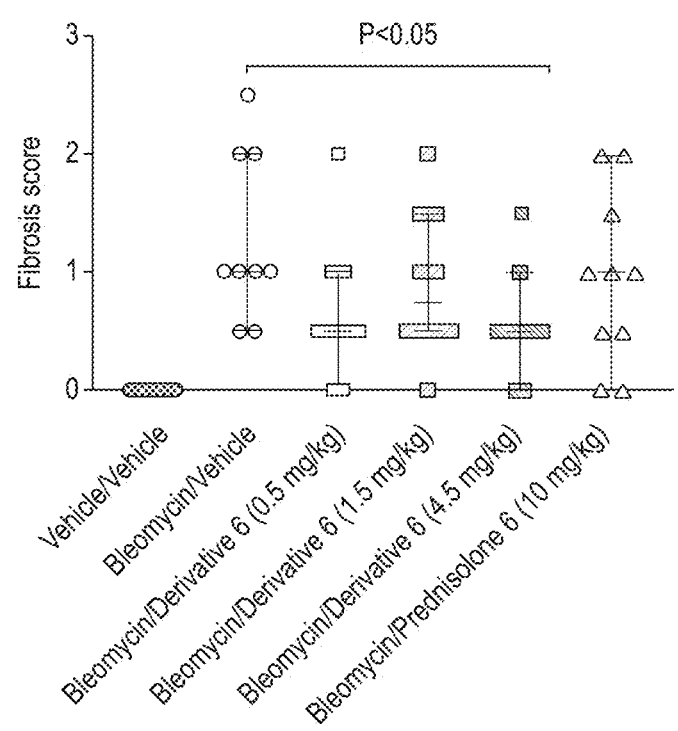

As illustrated in FIG. 11B, the Group median fibrosis score was increased in the bleomycin/vehicle controls (Group 2) compared with negative controls (Group 1). However, Group median fibrosis scores were decreased in rats treated with Derivative 6 (and significantly decreased in high dose Group 5) compared with bleomycin/vehicle controls but not with the control prednisolone.

Figure 11C:
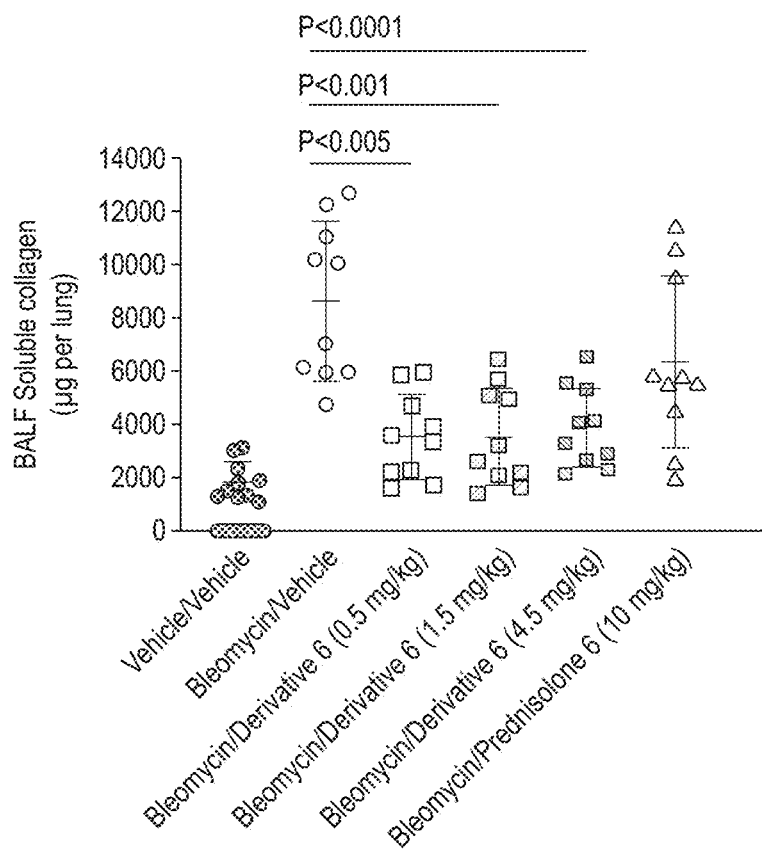

As illustrated in FIG. 11C, the amount of soluble collagen in BALF after bleomycin-induced lung injury was increased in the bleomycin/vehicle controls (Group 2) compared with negative controls (Group 1), and this was not reduced by treatment with prednisolone (Group 6). However, a significantly reduced amount of soluble collagen was observed in BALF from rats treated with Derivative 6 (across all doses tested) compared with bleomycin/vehicle controls. As soluble collagen in BALF is a read-out for fibrosis, these results confirm the histology data reported immediately above.

Conclusion

The results of the microscopic studies showed that the derivatives of the invention are able to prevent and/or reduce bleomycin-induced lung inflammation and fibrosis in a rat model. The effects seen with respect to inflammation were comparable to those observed with prednisolone, a corticosteroid known for treating lung inflammation. However, the derivatives of the invention had a unique action on fibrosis, not seen with prednisolone.

TABLE 14

Summary of Microscopic Findings in a Lung Injury Rat Model

| | 1 saline/ vehicle | 2 Bleo/ vehicle | 3 Bleo/ Derivative 6 0.5 mg/kg | 4 Bleo/ Derivative 6 1.5 mg/kg | 5 Bleo/ Derivative 6 4.5 mg/kg | 6 Bleo/ Pred |
|---|---|---|---|---|---|---|
| Fibrosis induced | Saline | Bleomycin | | | | |
| No. Animals Examined | 10 | 10 | 10 | 10 | 10 | 10 |
| Inflammation | | | | | | |
| Group Mean | 0.1 | 1.6 | 1.3 | 1.3 | 1.0 | 1.1 |
| Group Median | 0.0 | 2.0 | 1.0 | 1.0 | 1.0 | 1.0 |
| Fibrosis | | | | | | |
| Group Mean | 0.0 | 1.2 | 0.8 | 0.9 | 0.7 | 0.9 |
| Group Median | 0.0 | 1.0 | 1.0 | 1.0 | 0.0 | 1.0 |

As evidenced by comparing Groups 1 and 2 in Table 14, bleomycin induced both lung inflammation and fibrosis in the rat model. The mean and median scores were lower in Groups 3-5, i.e. rats treated with Derivative 6, a derivative of the invention. These lower scores were comparable with those seen in rats treated with prednisolone (Group 6).

Median inflammation and fibrosis scores for each animal in the study are also shown in FIGS. 11A and 11B, respectively.

As illustrated in FIG. 11A, the Group median inflammation score was increased in the bleomycin/vehicle controls (Group 2) compared with negative controls (Group 1). The Group median inflammation scores were decreased in rats treated with Derivative 6 (and significantly decreased in high dose Group 5) and prednisolone (Group 6) compared with bleomycin/vehicle controls.

Example 6

In Vivo Efficacy Study in Colitis

This study was designed to investigate the effect of dosing with a derivative of the invention in a colitis mouse model. The study was done in both preventive and treatment mode, meaning that dosing was initiated on the same day as the colon inflammation was induced and continued thereafter.

Methods

Chow-fed female C57Bl/6JRj mice were randomised to five groups (n=8 per group) based on body weight. DSS was used to induce colitis in four of the five groups. These mice received DSS in their drinking water for seven days from study day 0 to 6. In the fifth group, animals received water without DSS and hence served as healthy controls. From study day 0, DSS mice were treated with vehicle, a test derivative of IL-22 (Derivative 6; at 0.35 mg/kg or 1 mg/kg dosed intraperitoneally) or an IL-22-Fc fusion as comparator (hFc-hIL-22; at 0.5 mg/kg dosed intraperitoneally) once daily for 10 days. Body weight, food and water intake were monitored daily.

On study day 10, blood samples were collected from the mice in EDTA tubes and the plasma was separated and stored at −80° C. until analysis. Regenerating Islet Derived Protein 3 Gamma (Reg3g) was measured in duplicates using an ELISA kit (Cloud-Clone Corp), according to the manufacturer's instructions. Reg3g is a target engagement marker of IL-22.

At termination, the intestines were removed for stereological analysis. Accordingly, the gut was flushed with ice cold saline and its content gently removed before sampling. The intestine was infiltrated in formalin overnight (Tissue-Tek VIP) and subsequently embedded in blocks of paraffin. The formalin-fixed intestine was then sampled from the proximal to the distal direction using systematic uniform random sampling (SURS) principles, resulting in a total of four slabs and placed in a multi-cassette. All tissue slabs were placed in such a way that identification of individual slabs was possible at a later stage. The paraffin blocks were trimmed and 5 μm top sections were cut and mounted on Superfrost+ object glasses. For the large intestine, another section was cut with a 500 μm distance to the top section, thus giving rise to a total of eight colon sections from each animal.

Colon inflammation volume was measured stereologically, i.e. using a three-dimensional interpretation of two-dimensional cross sections of the colon. The stereological volume estimation was performed using the newCAST system (Visiopharm) on scanned H&E-stained slides. Total gut volume, volume of mucosa, volume of submucosa and muscularis and volume of inflamed tissue were estimated by point counting using a grid system of appropriate size, where all points hitting the structure of interest were counted. The number of points hitting the structure of interest were converted into volume according to the following mathematical relationship:

$$Vol_{ref} = \Sigma p \cdot A(p) \cdot t$$

where A(p) is the area per point, p is the total number of points hitting the structure of interest and t is the distance between sections. The mean inflammation volume per group was calculated and subjected to statistical analysis.

Colon morphology was also assessed at termination by viewing the H&E-stained slides.

Results

Figure 12:
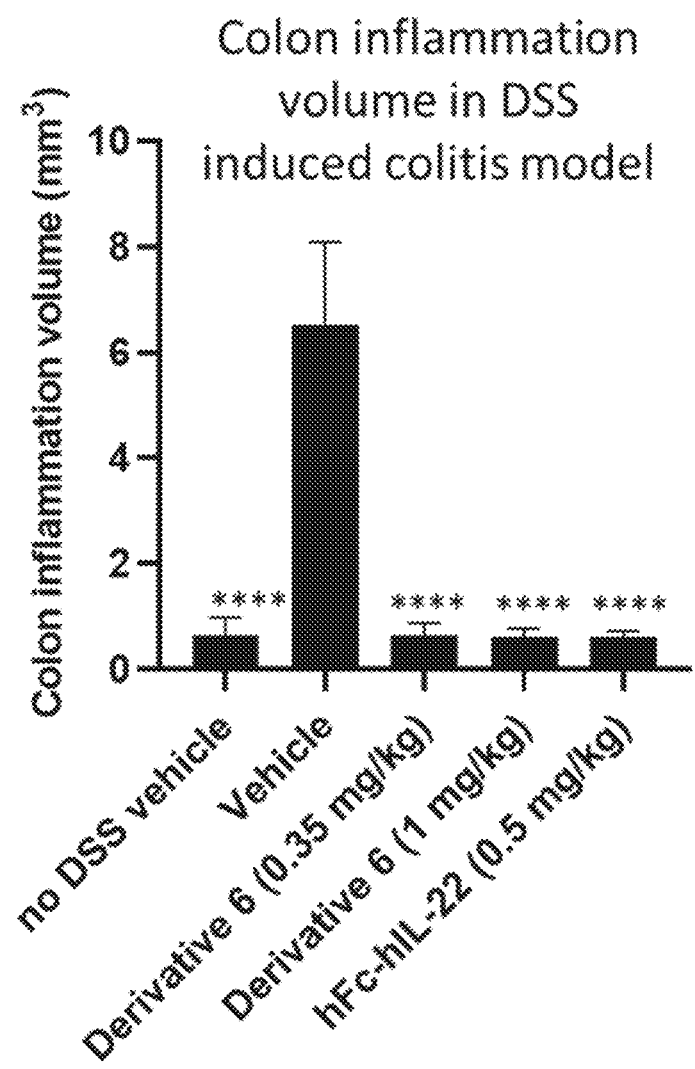
FIG. 12 illustrates the effect of Derivative 6 in preventing colon inflammation in a dextran sulfate sodium (DSS)-induced colitis mouse model. **** means $p<0.0001$ compared to vehicle (containing DSS).

Colon inflammation volume is shown in FIG. 12. Inflammation was shown to be prevented in mice treated with Derivative 6, at either dose, compared to the vehicle control (also containing DSS). Notably, inflammation remained at normal levels in the groups treated with Derivative 6, as evidenced by the colon inflammation volume being the same for the treated groups as the healthy controls (vehicle with no DSS). The same was true for the group treated with hFc-hIL-22.

Figure 13:
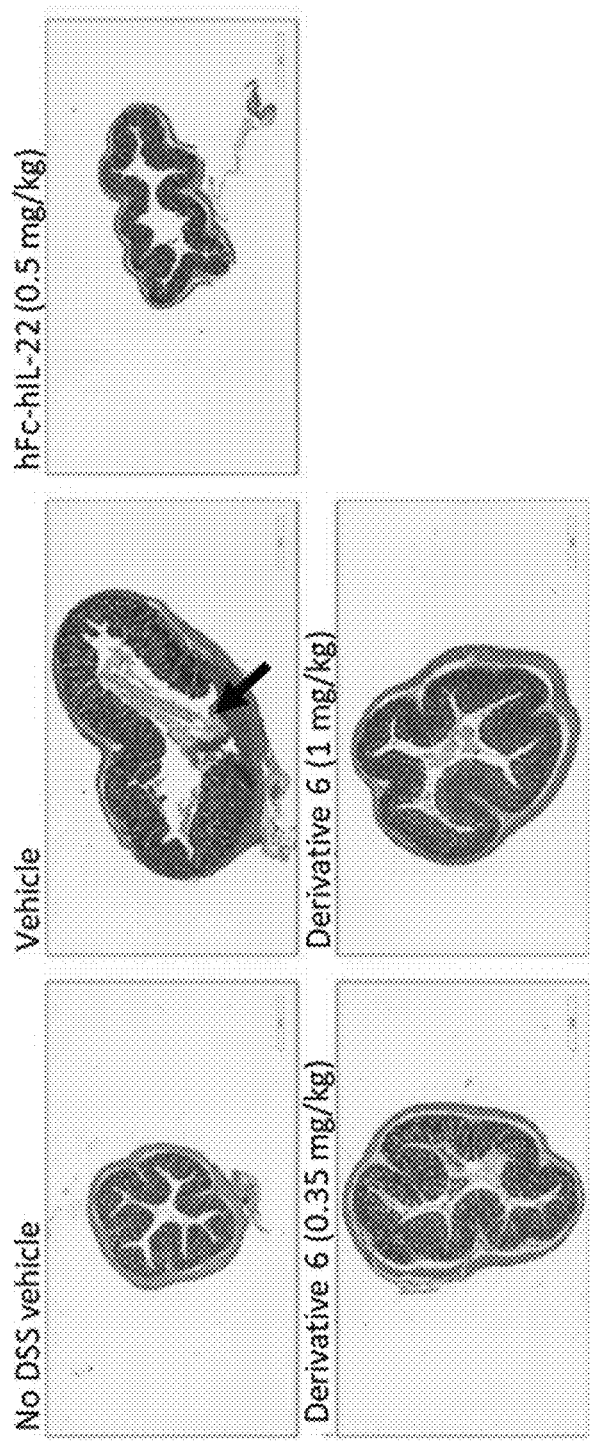
FIG. 13 illustrates the effect of Derivative 6 compared to hFc-hIL-22 in preventing mucosal epithelial wounding in the DSS-induced colitis mouse model. Magnification 4×, scale bar=500 μm.

Representative H&E staining images of colon morphology at termination are shown in FIG. 13. Following DSS treatment, mucosal epithelial wounding can be seen in vehicle-treated animals (marked by black arrow), but not in animals treated with Derivative 6 at either dose or hFc-hIL-22. This demonstrates a protective effect on epithelial tissue.

Figure 14:
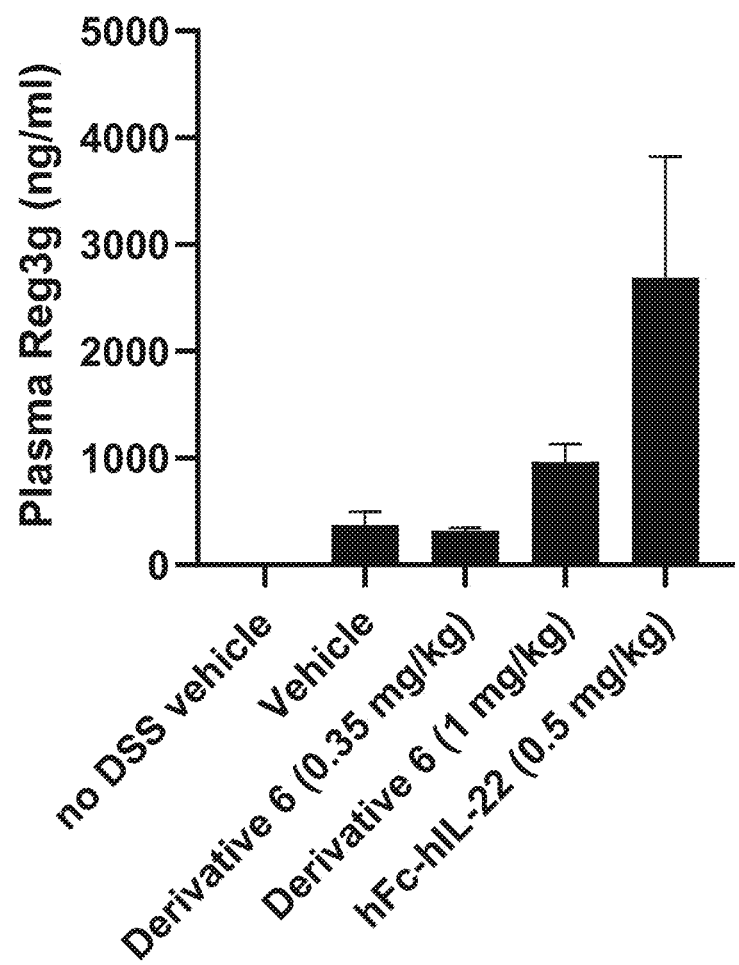
FIG. 14 illustrates plasma Regenerating Islet Derived Protein 3 Gamma (Reg3g) levels in the DSS-induced colitis mouse model, as a measure of target engagement (Reg3g is a target engagement marker of IL-22).

Plasma Reg3g levels are shown in FIG. 14. DSS treatment induced an increase in basal Reg3g levels (compare vehicle to no DSS vehicle). No further increase was detectable in the low dose (0.35 mg/kg) Derivative 6 group, but was seen in the higher dose (1 mg/kg) Derivative 6 group and the hFc-hIL-22 group. The higher Reg3g levels in the hFc-hIL-22 (0.5 mg/kg) group compared to the Derivative 6 (1 mg/kg) group indicated higher target engagement despite the lower dose, which was likely related to the longer half-life in mice of hFc-hIL-22 (T½ of 30 hours for hFc-hIL-22 vs 9.1 hours for Derivative 6).

Conclusion

The data hence show that a derivative of the invention demonstrates good efficacy in protecting against colitis and mucosal epithelial wounding in a mouse model. This indicates that a new and improved treatment for gut diseases, disorders and conditions has been found. In particular, the findings demonstrate the potential to treat disease characterised by mucosal epithelial damage, such as inflammatory bowel disease.

Example 7

In Vivo Efficacy Study in Liver Injury (ii)

This study was designed to investigate the effect of dosing with a derivative of the invention in a second liver injury mouse model (the first being described above in Example 4). The study was done in preventive mode, meaning that liver injury was only induced after dosing had been initiated.

Methods

C57Bl6/6j male mice were divided into five groups (n=8 per group). A test derivative of IL-22 (Derivative 1) was dosed at 1 mg/kg intraperitoneally in two of the five groups at −26 hours and −2 hours relative to ConA treatment. Another two groups received vehicle only at these time points. ConA was given to all four groups as an intravenous bolus over a 30-second period at a dose of 15 mg/kg, to induce liver injury. The fifth group received no ConA (vehicle only, as above), as healthy controls.

8 or 24 hours after ConA injection, the mice were placed under isoflurane anaesthesia and the maximal volume of blood was taken by cardiac puncture (using a polypropylene serum gel tube containing a clot activator). Mice receiving no treatment (Group 5) were sacrificed at the 8-hour time point. The blood was mixed with the clotting activation agent in each tube by inverting the tube several times. The tube was maintained for 15 minutes at room temperature and then centrifuged at 2000 g for 10 minutes at 4° C. ALT and AST were measured in the serum samples using an automated system (Konelab 20) according to manufacturer's instructions.

Results

Figure 15A:
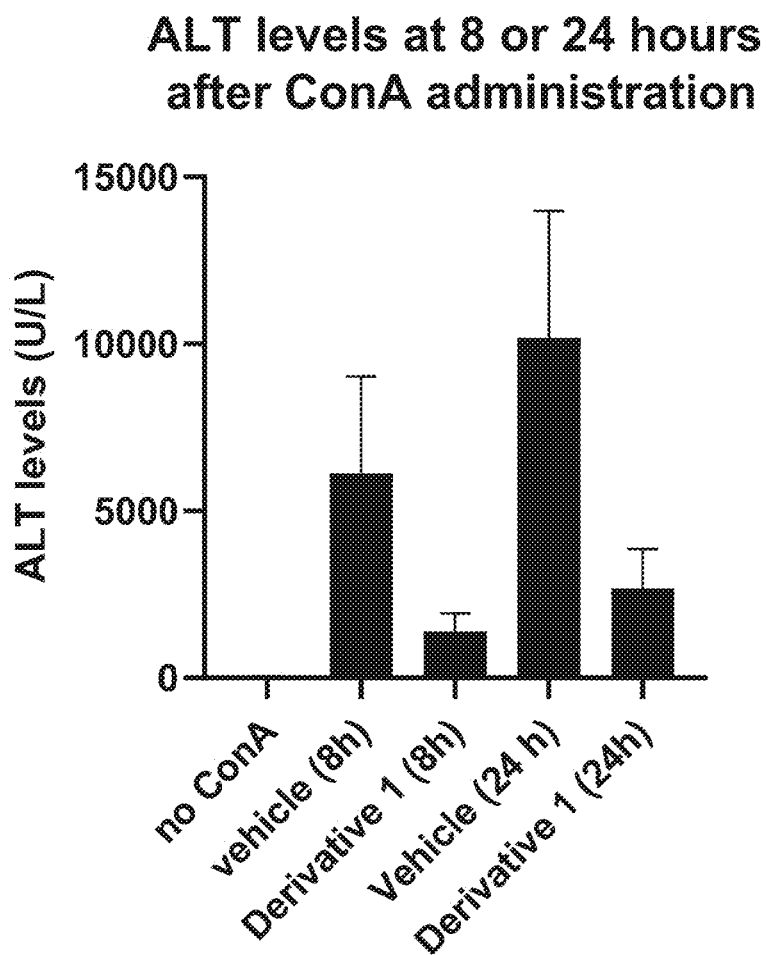
FIGS. 15A-15B illustrate the effect of Derivative 1 in preventing liver injury in a Concanavalin A (ConA)-induced liver injury mouse model, as evidenced by serum levels of two different liver enzymes.
Figure 15B:
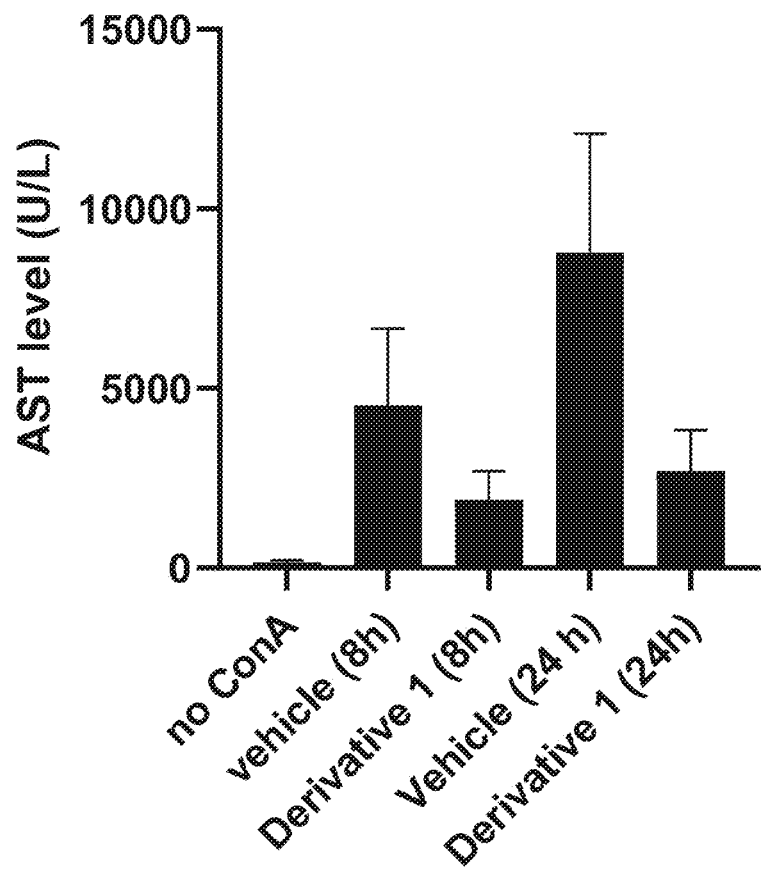

Plasma levels of ALT and AST at the termination of the study are shown in FIGS. 15A and 15B, respectively. The amount of ALT and AST was shown to be reduced in mice treated with Derivative 1 prior to liver injury compared to the vehicle/ConA control, at both time points tested.

Conclusion

ALT and AST are liver enzymes used as indicators of liver damage. Derivative 1 was hence shown to protect the liver against injury induced by ConA, just as it had against injury induced by APAP in Example 4. The particular biomarkers measured in the mice are known to translate to man, hence it is reasonable to predict that the observed protection would translate too.

Example 8

In Vivo Efficacy Study in Obesity and NASH

This study was designed to investigate the effect of dosing with a derivative of the invention in an obese and NASH mouse model. The study was done in treatment (not preventive) mode, meaning that obesity and NASH pathology was developed before dosing was initiated.

Methods

The Diet Induced Obese mouse model was based on male C57BL/6JRj mice, which were fed a high fat diet for at least 30 weeks prior to the experiment. The diet was high in fat (40%), fructose (22%) and cholesterol (2%) (Research Diets D09100310). This resulted in obesity, NAFLD and ultimately NASH.

The animals were single-housed six days prior to the first dose of test derivative (or other) and body weight was monitored daily throughout the experiment. The mice were divided into six groups (n=12 per group). Dosing was initiated at study day 0 (indicated with dotted line in FIG. 16) and administered once daily subcutaneously in the following doses.

Semaglutide, a long acting GLP-1 receptor agonist, was used a positive control in a first group, and also investigated in combination with a test derivative of IL-22 (Derivative 6) in a second group. The dosing of semaglutide was gradually titrated according to the following schedule: 0.6 nmol/kg day 0-1.2 nmol/kg day 1-2.4 nmol/kg day 2-4.8 nmol/kg day 3-12 nmol/kg day 4-30 nmol/kg day 5. In the combination group, semaglutide dosing was initiated at day 0 and Derivative 6 dosing was initiated at day 12 (indicated with dotted line in FIG. 16) after weight loss had plateaued in the semaglutide treated group.

The dosing of Derivative 6 in a third, "high dose" group was gradually titrated according to the following schedule: 0.05 mg/kg day 0—0.1 mg/kg day 1—0.15 mg/kg day 2—0.2 mg/kg day 3—0.25 mg/kg day 4. The dose was switched from 0.25 mg/kg to 0.1 mg/kg at day 14 (indicated with dotted line in FIG. 16). In a fourth, "low dose" group, dosing of Derivative 6 started at 0.05 mg/kg with no further titration.

In a fifth group, the dosing of an IL-22-Fc fusion (hFc-hIL-22) as comparator was gradually titrated according to the following schedule: 0.02 mg/kg day 0-0.04 mg/kg day 1-0.06 mg/kg day 2-0.08 mg/kg day 3-0.1 mg/kg day 4. The dose of hFc-hIL-22 was chosen to match the 0.25 mg/kg Derivative 6 group for target engagement based on the longer half-life and correspondingly higher target engagement compared to Derivative 6 as seen in Example 6 (see FIG. 14).

The sixth group were dosed with vehicle only as negative controls.

initiation. Specifically, tail blood samples were collected for analysis by pressing a tail blood volume at or below 200 µl into an open Microvette (100 µl or 200 µl) tube treated with the appropriate anticoagulant. Blood was placed at 4° C. until it was centrifuged at 3000 g for 10 minutes. The plasma supernatants were transferred to new tubes and immediately frozen on dry ice and stored at −80° C. TG levels were measured using commercial kits (Roche Diagnostics) on the Cobas® c 501 autoanalyzer according to the manufacturer's instructions.

Results

Figure 16:
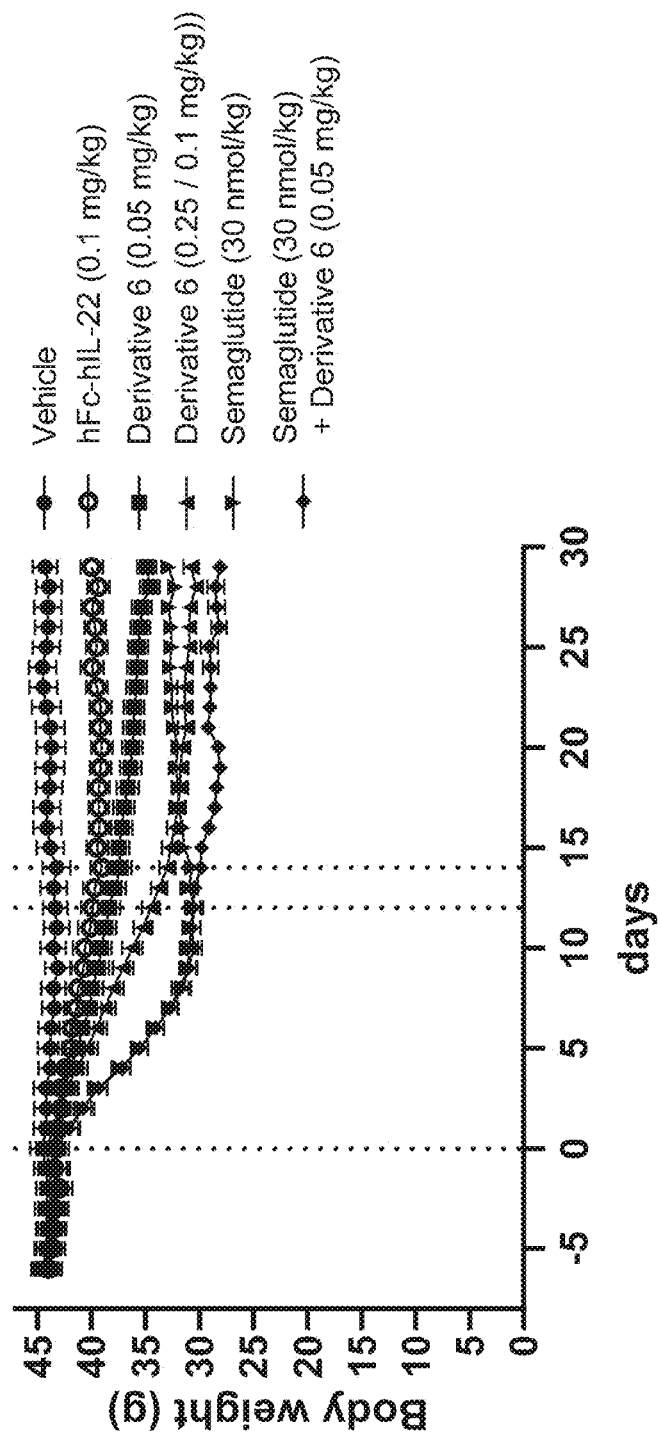
FIG. 16 illustrates the effect of Derivative 6 compared to hFc-hIL-22 and the known fatty acid conjugated GLP-1 derivative, semaglutide, on body weight in Diet Induced Obese mice.

Body weight over the course of the experiment is illustrated in FIG. 16.

The study demonstrated dose-dependent high efficacy of Derivative 6 in lowering body weight in the obese mouse model. Furthermore, it demonstrated additivity to a GLP-1 receptor agonist (semaglutide), which is being investigated in late stage clinical trials for obesity treatment. The data suggested superiority of Derivative 6 compared to hFc-hIL-22 in inducing weight loss. Importantly, hFc-hIL-22 has a longer half-life in mice than Derivative 6, and has demonstrated higher target engagement even when dosed at half the dose of Derivative 6. Thus, the dose of 0.1 mg/kg hFc-hIL-22 used in this study was chosen for similar target engagement as the 0.25 mg/kg Derivative 6 group.

The sensitivity to weight loss induced by Derivative 6, here observed in Diet Induced Obese mice, is not observed in lean mice. For example, in a 10-day DSS-induced colitis study (Example 6) with once daily dosing, body weight at study initiation was 19.0 g in both the DSS/vehicle group and the DSS/Derivative 6 (0.35 mg/kg) group. At the end of the study the body weight was 17.6 gram in the DSS/vehicle group versus 17.4 gram in the DSS/Derivative 6 (0.35 mg/kg) group, which are not different (p=0.82 in unpaired students t-test). By comparison, mice in the vehicle and Derivative 6 (0.25 mg/kg) groups at day 10 in the present study had body weights of 43.5 g and 35.2 g, respectively. Thus, a significant weight loss was observed in the Derivative 6 group compared to the vehicle group (p<0.0001 in unpaired students t-test for body weight at day 10). At study initiation, the body weight was similar in the vehicle group versus the Derivative 6 group (44.3 g and 44.1 g, respectively).

Plasma TG levels, as measured at baseline (day −2), week 2 (day 14) and week 4 (day 28) following dosing initiation, are shown in Table 15.

TABLE 15

Plasma TG levels (nmol/l) in an obese and NASH mouse model

| | Vehicle | | hFc-hIL-22 | | Derivative 6 (0.05 mg/kg) | | Derivative 6 (0.25/0.1 mg/kg) | | Semaglutide (30 nmol/kg) | | Semaglutide (30 nmol/kg) + Derivative 6 (0.05 mg/kg) | |
|---|---|---|---|---|---|---|---|---|---|---|---|---|
| | Mean | SEM | Mean | SEM | Mean | SEM | Mean | SEM | Mean | SEM | Mean | SEM |
| Baseline | 0.75 | 0.033 | 0.85 | 0.036 | 0.83 | 0.045 | 0.77 | 0.035 | 0.81 | 0.036 | 0.86 | 0.046 |
| Week 2 | 1.00 | 0.059 | 0.68 | 0.043 | 0.58 | 0.038 | 0.52 | 0.027 | 0.65 | 0.037 | 0.46 | 0.033 |
| Delta week 2 | +0.24 | 0.071 | −0.18 | 0.047 | −0.25 | 0.050 | −0.25 | 0.050 | −0.15 | 0.046 | −0.41 | 0.066 |
| Week 4 | 0.93 | 0.076 | 0.84 | 0.046 | 0.54 | 0.030 | 0.42 | 0.030 | 0.66 | 0.048 | 0.34 | 0.032 |
| Delta week 4 | +0.17 | 0.079 | −0.02 | 0.059 | −0.30 | 0.034 | −0.35 | 0.052 | −0.14 | 0.066 | −0.53 | 0.042 |

Plasma triglyceride (TG) levels were measured at baseline (day −2), week 2 (day 14) and week 4 (day 28) after dosing Delta refers to the change in TG level (nmol/l) from baseline for the indicated treatment and timepoint. As can be seen from Table 15, the change in level was positive (increased) for the vehicle group, but negative (decreased) for all other groups.

Derivative 6 had higher efficacy in lowering TG levels than semaglutide, also in the low dose, which causes less weight loss than semaglutide (e.g. week 4 delta TG levels (nmol/l) of −0.14±0.066 for semaglutide, −0.30±0.034 for Derivative 6 (0.05 mg/kg) and −0.35±0.052 for Derivative 6 (0.25/0.1 mg/kg)). The results show that Derivative 6 had a high efficacy in TG lowering, which is partially independent of the weight loss effect. Furthermore, there was full additivity of the Derivative 6 effect on top of semaglutide. At week 4, the lowering of TG levels (nmol/1), calculated as delta TG, was −0.30±0.034 for Derivative 6 (0.05 mg/kg), −0.14±0.066 for semaglutide and −0.53±0.042 for semaglutide +Derivative 6 (0.05 mg/kg). The TG lowering results compared to baseline (delta TG) were despite TG levels in the vehicle group increasing over the course of the study.

Conclusion

The study demonstrated that a derivative of the invention (Derivative 6) can induce weight loss in obese mice in a dose-dependent manner at least to a comparable level as seen with semaglutide—a long acting GLP-1 receptor agonist used a positive control. Furthermore, there was an additive effect on weight loss using a combination of semaglutide and Derivative 6. The efficacy of Derivative 6 in inducing weight loss was higher than observed with hFc-IL-h22 at doses chosen to give a similar level of target engagement. The weight loss induced by Derivative 6 in Diet Induced Obese mice was not seen in DSS-treated lean mice, demonstrating that obese mice are more sensitive to Derivative 6-induced weight loss. As body weight loss observed in Diet Induced Obese mice is the same read-out as would be used in man, it is reasonable to predict that the observed weight loss would translate too.

Derivative 6 also showed high efficacy in lowering TG levels. Derivative 6, in both doses tested, showed higher efficacy than semaglutide and full additivity on efficacy in combination dosing was observed. Given that the 0.05 mg/kg dose of Derivative 6 had higher efficacy than semaglutide despite lower weight loss, it can be concluded that the TG lowering effect of Derivative 6 was at least partially independent of weight loss. Furthermore, Derivative 6 was superior to the hFc-hIL-22 comparator at both of the tested doses. As the TG lowering observed in Diet Induced Obese mice was the same read-out as would be used in man, it is reasonable to predict that the observed effect would translate too. The results hence indicate that a new treatment for disorders and conditions characterised by high TG levels has been found.

While certain features of the invention have been illustrated and described herein, many modifications and equivalents will occur to those of ordinary skill in the art. It is, therefore, to be understood that the claims are intended to cover all such modifications and equivalents as fall within the true spirit of the invention.

The invention claimed is:

1. A derivative of IL-22 comprising a fatty acid covalently attached to an IL-22 protein by a linker, wherein:
   (i) the fatty add comprises C18 diacid;
   (ii) the IL-22 protein is a variant of human IL-22 (hIL-22), wherein hIL-22 comprises the amino acid sequence of SEQ ID NO: 1, wherein the variant comprises:
      (a) a Cys substitution at position 1 of hIL-22;
      (b) an N-terminal G-P-G, and
wherein the fatty acid is covalently attached to the Cys substitution at position 1 of hIL-22 by the linker.

2. A pharmaceutical composition comprising a derivative as claimed in claim 1 and a pharmaceutically acceptable vehicle.

3. The pharmaceutical composition of claim 2, wherein the pharmaceutical composition is suitable for administration by inhalation, by injection, topically, orally, or ocularly.

4. The pharmaceutical composition of claim 3, wherein the injection is intraperitoneal, subcutaneous or intravenous.

5. The derivative as claimed in claim 1, wherein the variant comprises one or two more variations within SEQ ID NO: 1, wherein said variations are amino acid substitutions.

6. The derivative as claimed in claim 5, wherein the variant comprises amino acid substitutions at positions 35 and 64 of hIL-22.

7. The derivative as claimed in claim 6, wherein the linker comprises yGlu-OEG-OEG-C2DA-Ac.

8. A pharmaceutical composition comprising a derivative as claimed in claim 7 and a pharmaceutically acceptable vehicle.

9. The pharmaceutical composition of claim 8, wherein the pharmaceutical composition is suitable for administration by inhalation, by injection, topically, orally, or ocularly.

10. The pharmaceutical composition of claim 9, wherein the injection is intraperitoneal, subcutaneous or intravenous.

11. The derivative as claimed in claim 7, wherein the derivative of IL-22 has prolonged circulatory half-life as compared to hIL-22 without the fatty acid.

12. A pharmaceutical composition comprising a derivative as claimed in claim 11 and a pharmaceutically acceptable vehicle.

13. The pharmaceutical composition of claim 12, wherein the pharmaceutical composition is suitable for administration by inhalation, by injection, topically, orally, or ocularly.

14. The pharmaceutical composition of claim 13, wherein the injection is intraperitoneal, subcutaneous or intravenous.

15. The derivative as claimed in claim 6, wherein the derivative of IL-22 has prolonged circulatory half-life as compared to hIL-22 without the fatty acid.

16. A pharmaceutical composition comprising a derivative as claimed in claim 15 and a pharmaceutically acceptable vehicle.

17. The pharmaceutical composition of claim 16, wherein the pharmaceutical composition is suitable for administration by inhalation, by injection, topically, orally, or ocularly.

18. The pharmaceutical composition of claim 17, wherein the injection is intraperitoneal, subcutaneous or intravenous.

19. A pharmaceutical composition comprising a derivative as claimed in claim 6 and a pharmaceutically acceptable vehicle.

20. The pharmaceutical composition of claim 19, wherein the pharmaceutical composition is suitable for administration by inhalation, by injection, topically, orally, or ocularly.

21. The pharmaceutical composition of claim 20, wherein the injection is intraperitoneal, subcutaneous or intravenous.

22. The derivative as claimed in claim 5, wherein the linker comprises γGlu-OEG-OEG-C2DA-Ac.

23. The derivative as claimed in claim 22, wherein the derivative of IL-22 has prolonged circulatory half-life as compared to hIL-22 without the fatty acid.

24. A pharmaceutical composition comprising a derivative as claimed in claim 23 and a pharmaceutically acceptable vehicle.

25. The pharmaceutical composition of claim 24, wherein the pharmaceutical composition is suitable for administration by inhalation, by injection, topically, orally, or ocularly.

26. The pharmaceutical composition of claim 25, wherein the injection is intraperitoneal, subcutaneous or intravenous.

27. A pharmaceutical composition comprising a derivative as claimed in claim 22 and a pharmaceutically acceptable vehicle.

28. The pharmaceutical composition of claim 27, wherein the pharmaceutical composition is suitable for administration by inhalation, by injection, topically, orally, or ocularly.

29. The pharmaceutical composition of claim 28, wherein the injection is intraperitoneal, subcutaneous or intravenous.

30. The derivative as claimed in claim 5, wherein the derivative of IL-22 has prolonged circulatory half-life as compared to hIL-22 without the fatty acid.

31. A pharmaceutical composition comprising a derivative as claimed in claim 30 and a pharmaceutically acceptable vehicle.

32. The pharmaceutical composition of claim 31, wherein the pharmaceutical composition is suitable for administration by inhalation, by injection, topically, orally, or ocularly.

33. The pharmaceutical composition of claim 32, wherein the injection is intraperitoneal, subcutaneous or intravenous.

34. A pharmaceutical composition comprising a derivative as claimed in claim 5 and a pharmaceutically acceptable vehicle.

35. The pharmaceutical composition of claim 34, wherein the pharmaceutical composition is suitable for administration by inhalation, by injection, topically, orally, or ocularly.

36. The pharmaceutical composition of claim 35, wherein the injection is intraperitoneal, subcutaneous or intravenous.

37. The derivative as claimed in claim 1, wherein the variant comprises amino acid substitutions N35Q and N64Q of hIL-22.

38. The derivative as claimed in claim 37, wherein the linker comprises γGlu-OEG-OEG-C2DA-Ac.

39. The derivative as claimed in claim 38, wherein the derivative of IL-22 has prolonged circulatory half-life as compared to hIL-22 without the fatty acid.

40. A pharmaceutical composition comprising a derivative as claimed in claim 39 and a pharmaceutically acceptable vehicle.

41. The pharmaceutical composition of claim 40, wherein the pharmaceutical composition is suitable for administration by inhalation, by injection, topically, orally, or ocularly.

42. The pharmaceutical composition of claim 41, wherein the injection is intraperitoneal, subcutaneous or intravenous.

43. A pharmaceutical composition comprising a derivative as claimed in claim 38 and a pharmaceutically acceptable vehicle.

44. The pharmaceutical composition of claim 43, wherein the pharmaceutical composition is suitable for administration by inhalation, by injection, topically, orally, or ocularly.

45. The pharmaceutical composition of claim 44, wherein the injection is intraperitoneal, subcutaneous or intravenous.

46. The derivative as claimed in claim 37, wherein the derivative of IL-22 has prolonged circulatory half-life as compared to hIL-22 without the fatty acid.

47. A pharmaceutical composition comprising a derivative as claimed in claim 46 and a pharmaceutically acceptable vehicle.

48. The pharmaceutical composition of claim 47, wherein the pharmaceutical composition is suitable for administration by inhalation, by injection, topically, orally, or ocularly.

49. The pharmaceutical composition of claim 48, wherein the injection is intraperitoneal, subcutaneous or intravenous.

50. A pharmaceutical composition comprising a derivative as claimed in claim 37 and a pharmaceutically acceptable vehicle.

51. The pharmaceutical composition of claim 50, wherein the pharmaceutical composition is suitable for administration by inhalation, by injection, topically, orally, or ocularly.

52. The pharmaceutical composition of claim 51, wherein the injection is intraperitoneal, subcutaneous or intravenous.

53. The derivative as claimed in claim 1, wherein the variant comprises the amino acid sequence of SEQ ID NO: 16 or SEQ ID NO: 18.

54. The derivative as claimed in claim 53, wherein the linker comprises γGlu-OEG-OEG-C2DA-Ac.

55. The derivative as claimed in claim 54, wherein the derivative of IL-22 has prolonged circulatory half-life as compared to hIL-22 without the fatty acid.

56. A pharmaceutical composition comprising a derivative as claimed in claim 55 and a pharmaceutically acceptable vehicle.

57. The pharmaceutical composition of claim 56, wherein the pharmaceutical composition is suitable for administration by inhalation, by injection, topically, orally, or ocularly.

58. The pharmaceutical composition of claim 57, wherein the injection is intraperitoneal, subcutaneous or intravenous.

59. A pharmaceutical composition comprising a derivative as claimed in claim 54 and a pharmaceutically acceptable vehicle.

60. The pharmaceutical composition of claim 59, wherein the pharmaceutical composition is suitable for administration by inhalation, by injection, topically, orally, or ocularly.

61. The pharmaceutical composition of claim 60, wherein the injection is intraperitoneal, subcutaneous or intravenous.

62. The derivative as claimed in claim 53, wherein the derivative of IL-22 has prolonged circulatory half-life as compared to hIL-22 without the fatty acid.

63. A pharmaceutical composition comprising a derivative as claimed in claim 62 and a pharmaceutically acceptable vehicle.

64. The pharmaceutical composition of claim 63, wherein the pharmaceutical composition is suitable for administration by inhalation, by injection, topically, orally, or ocularly.

65. The pharmaceutical composition of claim 64, wherein the injection is intraperitoneal, subcutaneous or intravenous.

66. A pharmaceutical composition comprising a derivative as claimed in claim 53 and a pharmaceutically acceptable vehicle.

67. The pharmaceutical composition of claim 66, wherein the pharmaceutical composition is suitable for administration by inhalation, by injection, topically, orally, or ocularly.

68. The pharmaceutical composition of claim 67, wherein the injection is intraperitoneal, subcutaneous or intravenous.

69. The derivative as claimed in claim 1, wherein the linker comprises γGlu-OEG-OEG-C2DA-Ac.

70. The derivative as claimed in claim 69, wherein the derivative of IL-22 has prolonged circulatory half-life as compared to hIL-22 without the fatty acid.

71. A pharmaceutical composition comprising a derivative as claimed in claim 70 and a pharmaceutically acceptable vehicle.

72. The pharmaceutical composition of claim 71, wherein the pharmaceutical composition is suitable for administration by inhalation, by injection, topically, orally, or ocularly.

73. The pharmaceutical composition of claim 72, wherein the injection is intraperitoneal, subcutaneous or intravenous.

74. A pharmaceutical composition comprising a derivative as claimed in claim 69 and a pharmaceutically acceptable vehicle.

75. The pharmaceutical composition of claim 74, wherein the pharmaceutical composition is suitable for administration by inhalation, by injection, topically, orally, or ocularly.

76. The pharmaceutical composition of claim 75, wherein the injection is intraperitoneal, subcutaneous or intravenous.

77. The derivative as claimed in claim 1, wherein the derivative of IL-22 has prolonged circulatory half-life as compared to hIL-22 without the fatty acid.

78. A pharmaceutical composition comprising a derivative as claimed in claim 77 and a pharmaceutically acceptable vehicle.

79. The pharmaceutical composition of claim 78, wherein the pharmaceutical composition is suitable for administration by inhalation, by injection, topically, orally, or ocularly.

80. The pharmaceutical composition of claim 79, wherein the injection is intraperitoneal, subcutaneous or intravenous.

81. A derivative IL-22 comprising a fatty acid covalently attached by a linker to a variant of hIL-22, wherein hIL-22 comprises the amino acid sequence of SEQ ID NO: 1, wherein:
  (a) the fatty acid comprises a C18 diacid;
  (b) the variant comprises the amino acid sequence of SEQ ID NO: 16; and
  (b) the linker comprises γGlu-OEG-OEG-C2DA-Ac; and wherein the linker is covalently attached to the Cys residue at position 4 of SEQ ID NO: 16.

82. The derivative as claimed in claim 81, wherein the derivative of IL-22 has prolonged circulatory half-life as compared to hIL-22 without the fatty acid.

83. A pharmaceutical composition comprising a derivative as claimed in claim 82 and a pharmaceutically acceptable vehicle.

84. The pharmaceutical composition of claim 83, wherein the pharmaceutical composition is suitable for administration by inhalation, by injection, topically, orally, or ocularly.

85. The pharmaceutical composition of claim 84, wherein the injection is intraperitoneal, subcutaneous or intravenous.

86. A pharmaceutical composition comprising a derivative as claimed in claim 81 and a pharmaceutically acceptable vehicle.

87. The pharmaceutical composition of claim 86, wherein the pharmaceutical composition is suitable for administration by inhalation, by injection, topically, orally, or ocularly.

88. The pharmaceutical composition of claim 87, wherein the injection is intraperitoneal, subcutaneous or intravenous.

89. A derivative of IL-22 comprising a fatty acid covalently attached by a linker to a variant of hIL-22, wherein hIL-22 comprises the amino acid sequence of SEQ ID NO: 1, wherein:
  (a) the fatty acid comprises a C18 diacid;
  (b) the variant comprises the amino acid sequence of SEQ ID NO: 18; and
  (c) the linker comprises γGlu-OEG-OEG-C2DA-Ac; and wherein the linker is covalently attached to the Cys residue at position 4 of SEQ ID NO: 18.

90. The derivative as claimed in claim 89, wherein the derivative of IL-22 has prolonged circulatory half-life as compared to hIL-22 without the fatty acid.

91. A pharmaceutical composition comprising a derivative as claimed in claim 90 and a pharmaceutically acceptable vehicle.

92. The pharmaceutical composition of claim 91, wherein the pharmaceutical composition is suitable for administration by inhalation, by injection, topically, orally, or ocularly.

93. The pharmaceutical composition of claim 92, wherein the injection is intraperitoneal, subcutaneous or intravenous.

94. A pharmaceutical composition comprising a derivative as claimed in claim 89 and a pharmaceutically acceptable vehicle.

95. The pharmaceutical composition of claim 94, wherein the pharmaceutical composition is suitable for administration by inhalation, by injection, topically, orally, or ocularly.

96. The pharmaceutical composition of claim 95, wherein the injection is intraperitoneal, subcutaneous or intravenous.

* * * * *